US012736525B2

(12) United States Patent
Barran et al.

(10) Patent No.: US 12,736,525 B2
(45) **Date of Patent: *Sep. 15, 2026**

(54) METHOD FOR DETECTING AND TREATING PARKINSON'S DISEASE COMPRISING SEBUM BIOMARKERS

(71) Applicant: The University of Manchester, Manchester (GB)

(72) Inventors: Perdita Barran, Manchester (GB); Depanjan Sarkar, Manchester (GB); Drupad Trivedi, Manchester (GB); Eleanor Sinclair, Manchester (GB); Monty Silverdale, Manchester (GB); Joy Milne, Manchester (GB)

(73) Assignee: The University of Manchester, Manchester (GB)

( * ) Notice: Subject to any disclaimer, the term of this patent is extended or adjusted under 35 U.S.C. 154(b) by 887 days.

This patent is subject to a terminal disclaimer.

(21) Appl. No.: 17/760,274

(22) PCT Filed: Feb. 5, 2021

(86) PCT No.: PCT/GB2021/050269

§ 371 (c)(1),
(2) Date: Aug. 5, 2022

(87) PCT Pub. No.: WO2021/156637

PCT Pub. Date: Aug. 12, 2021

(65) Prior Publication Data

US 2023/0080918 A1 Mar. 16, 2023

(30) Foreign Application Priority Data

Feb. 5, 2020 (GB) ..................................... 2001570

(51) Int. Cl.

| | |
|---|---|
| ***G01N 33/50*** | (2006.01) |
| ***G01N 27/623*** | (2021.01) |
| ***G01N 30/72*** | (2006.01) |
| ***G01N 33/92*** | (2006.01) |

(52) U.S. Cl.
CPC ....... *G01N 33/5038* (2013.01); *G01N 27/623* (2021.01); *G01N 30/72* (2013.01); *G01N 33/92* (2013.01); *G01N 2800/2835* (2013.01)

(58) Field of Classification Search
CPC .. G01N 33/5038; G01N 27/623; G01N 30/72; G01N 33/92; G01N 2800/2835; G01N 2333/70596; G01N 33/532; G01N 33/58; C07K 16/2809; C07K 2317/24; C07K 2317/31; C07K 2317/565; C07K 2317/56; C07K 2317/73; C07K 2317/92; C07K 2317/94; C07K 16/28; C07K 16/2875; C07K 16/32; A61P 35/00; C12N 15/63; A61K 2039/505; A61K 47/6803
See application file for complete search history.

(56) References Cited

U.S. PATENT DOCUMENTS

| | | | |
|---|---|---|---|
| 11,139,156 | B2 | 10/2021 | Balog et al. |
| 12,087,566 | B2 | 9/2024 | Eberlin et al. |
| 12,354,864 | B2 | 7/2025 | Barran et al. |
| 2013/0178383 | A1 | 7/2013 | Spetzler et al. |
| 2016/0220557 | A1 | 8/2016 | Esler et al. |
| 2016/0334381 | A1 | 11/2016 | King-Smith et al. |
| 2017/0125228 | A1 | 5/2017 | Bango et al. |
| 2018/0049643 | A1 | 2/2018 | Balog et al. |
| 2018/0059127 | A1 | 3/2018 | Indra et al. |
| 2018/0103935 | A1 | 4/2018 | Pringle et al. |
| 2018/0158661 | A1 | 6/2018 | Eberlin et al. |
| 2021/0287894 | A1 | 9/2021 | Barran et al. |
| 2023/0077659 | A1 | 3/2023 | Barran et al. |

FOREIGN PATENT DOCUMENTS

| | | | |
|---|---|---|---|
| CN | 107922962 | A | 4/2018 |
| EP | 1901064 | A2 | 3/2008 |
| JP | 2015055620 | A1 | 3/2015 |
| JP | 2016-206188 | A | 12/2016 |
| JP | 2018-517120 | A | 6/2018 |
| JP | 2019-534724 | A | 12/2019 |
| WO | WO 2006092689 | A1 | 9/2006 |
| WO | 2012/024543 | A1 | 2/2012 |
| WO | 2016/125120 | A1 | 8/2016 |
| WO | WO 2016130646 | A1 | 8/2016 |
| WO | 2016/164795 | A1 | 10/2016 |
| WO | 2018/132746 | A1 | 7/2018 |
| WO | 2018/183448 | A1 | 10/2018 |
| WO | 2020/025967 | A1 | 2/2020 |
| WO | 2021156638 | A1 | 8/2021 |
| WO | WO 2021156637 | A1 | 8/2021 |
| WO | 2011/154261 | A9 | 1/2025 |

OTHER PUBLICATIONS

Esler et al., Science Translational Medicine, 11:eaau8465, May 15, 2019.*
Stewart et al., Biochimica et Biophysica Acta, 529:380-386, (Year: 1978).*
Sigma product information sheet for 1,2-diacyl-sn-glycero-3-phosphocholine, May 2003.*
Kolter, Ganglioside Biochemistry, International Scholarly Research Network, ISRN Biochemistry, Article ID 506160, 1-36, 2012.
Schnaar et al., Glycosphingolipids, Essentials of Glycobiology [Internet]. 4th edition, Chapter 11, Varki A, Cummings RD, Esko JD, et al., editors. Cold Spring Harbor (NY): Cold Spring Harbor Laboratory Press; 2022), 1-12.
Abedi, G., et al., "The survey of analytical methods for sample preparation and analysis of fragrances in cosmetics and personal care products," TrAC Trends in Analytical Chemistry, Feb. 2018.
Abu-Farha M, et al., "The role of lipid metabolism in COVID-19 virus infection and as a drug target," Int J Mol Sci 2020; 21.

(Continued)

*Primary Examiner* — Stacey N MacFarlane
(74) *Attorney, Agent, or Firm* — Hamilton, Brook, Smith & Reynolds, P.C.

(57) ABSTRACT

The present invention relates to methods for detecting the presence or absence of Parkinson's disease (PD).

15 Claims, 43 Drawing Sheets

(56) References Cited

OTHER PUBLICATIONS

Camera, et al., "Use of lipidomics to investigate sebum dysfunction in juvenile acne," Journal of Lipid Research, vol. 57, No. 6, Jun. 1, 2016 (Jun. 1, 2016), pp. 1051-1058.
Chang, J.-E., et al., "Analysis of volatile organic compounds in exhaled breath for lung cancer diagnosis using a sensor system," Sensors and Actuators B: Chemical, 255: p. 800-807, Jul. 2017.
Cheng, H.- C., et al., "Clinical Progression in Parkinson's Disease and the Neurobiology of Axons," Annals of neurology, 67(6): p. 715-725, Jun. 2010.
Cody, R. B., et al., "Versatile new ion source for the analysis of materials in open air under ambient conditions," Anal. Chem. 2005, 77 (8), 2297-2302.
Cooks, R. G.; Ouyang, Z.; Takats, Z.; Wiseman, J. M., "Ambient Mass Spectrometry," Science (Washington, DC, U.S.) 2006, 311 (5767), 1566-1570.
Demaagd, G. and A. Philip, "Parkinson's Disease and Its Management: Part 1: Disease Entity, Risk Factors, Pathophysiology, Clinical Presentation, and Diagnosis," Pharmacy and Therapeutics, 40(8): p. 504-532, Aug. 2015.
De Silva IW, ct al., "Paper spray mass spectrometry utilizing Teslin® substrate for rapid detection of lipid metabolite changes during COVID-19 infection," Analyst 2020; 145.
Destaillats et al., "Identification of 116-monounsaturated fatty acids in human hair and nail samples by gas-chromatography-mass-spectrometry using ionic-liquid coated capillary column," Journal of Chromatography A, vol. 1218(2011):9394-9389, Nov. 2011.
Donadio, V., et al., "Skin nerve alpha-synuclein deposits: a biomarker for idiopathic Parkinson disease," Neurology, 82(15): p. 1362-9, Mar. 2014.
Dunn, W.B., ct al., "Systems level studies of mammalian metabolomes: the roles of mass spectrometry and nuclear magnetic resonance spectroscopy," Chem Soc Rev, 40(1): p. 387-426, Feb. 2011.
Esler WP, et al., "Human sebum requires de novo lipogenesis, which is increased in acne vulgaris and suppressed by acetyl-CoA carboxylase inhibition," Sci Transl Med 2019; 11: 1-14.
Eyre MT, et al., "Impact of baseline cases of cough and fever on Uk COVID-19 diagnostic testing rates: estimates from the Bug Watch community cohort study," medRxiv 2020; : 2020.09.03.20187377.
Fall F, et al., "A split-range acquisition method for the non-targeted metabolomic profiling of human plasma with hydrophilic interaction chromatography—high-resolution mass spectrometry," J Chromatogr B Anal Technol Biomed Life Sci 2019; 1128: 121780.
Fenn, J. B.; Mann, M.; Meng, C. K.; Wong, S. F.; Whitehouse, C. M., "Electrospray ionization for mass spectrometry of large biomolecules," Science (Washington, D. C., 1883-) 1989, 246(4926), 64-71.
Gabelica, V., et al., "Recommendations for reporting ion mobility Mass Spectrometry measurements," Mass Spectrom. Rev. 2019, 38 (3), 291-320.
Gatzias, I., et al., "Characterization and differentiation of sheep's milk from Greek breeds based on physicochemical parameters, fatty acid composition and volatile profile," Journal of the Science of Food and Agriculture, Aug. 2018.
Gerhardt, N., et al., "Volatile Compound Fingerprinting by Headspace Gas Chromatography-Ion Mobility Spectrometry (HS-GC-IMS) for the Authenticity Assessment of Honey as Benchtop Alternative to 1 H-NMR Profiling," Analytical chemistry, Jan. 2018.
Goodacre, R., et al., "Proposed minimum reporting standards for data analysis in metabolomics," Metabolomics, 3(3): p. 231-241, Aug. 2007.
Herrington, J.S. and C. Myers, "Electronic cigarette solutions and resultant acrosol profiles," Journal of chromatography A, 1418: p. 192-199, Sep. 2015.
Hillenkamp, F.; Karas, M.; Beavis, R. C.; Chait, B. T., "Matrix-assisted laser desorption/ionization mass spectrometry of biopolymers," Anal. Chem. 1991, 63 (24), 1193A-1203A.
Y-C Huang, et al., "Predicting Breast Cancer by Paper Spray Ion Mobility Spectrometry Mass Spectrometry and Machine Learning," Analytical Chemistry, vol. 92, No. 2, Dec. 6, 2019 (Dec. 6, 2019), pp. 1653-1657.
Ishibc, A., ct al., "Detection of gas components as a novel diagnostic method for colorectal cancer," Annals of Gastroenterological Surgery, 2018.
Jackson, A. T., et al., "Microstructural and conformational studies of polyether copolymers," Int. J. Mass Spectrom. 2004, 238 (3), 287-297.
Jendrny P, et al., "Scent dog identification of samples from COVID-19 patients—A pilot study," BMC Infect Dis 2020; 20: 1-7.
Kendall, et al., "Lipidomics for translational skin research: A primer for the uninitiated," Experimental Dermatology, vol. 27, No. 7, May 7, 2018 (May 7, 2018), pp. 721-728.
Kobayashi T, Voisin B, Kim DY, et al., "Homeostatic Control of Sebaceous Glands by Innate Lymphoid Cells Regulates Commensal Bacteria Equilibrium," Cell 2019; 176: 982-997.e16.
Knight SR, et al., "Risk stratification of patients admitted to hospital with covid-19 using the Isaric Who Clinical Characterisation Protocol: development and validation of the 4C Mortality Score," BMJ 2020; 370: m3339.
Krechmer, Jordan, et al., "Real Time Lipidomic Profiling Using Desorption Ionization with Ion Mobility MS," Metabolomics and Lipidomics Applications, Feb. 1, 2016 (Feb. 1, 2016), pp. 275-281.
Krestin, D., "The Seborrhoeic Facies as a Manifestation of Post-Encephalitic Parkinsonism and Allied Disorders," QJM: An International Journal of Medicine, os-21(81): p. 177-186, Jul. 1927.
Lawal, O., et al., "Headspace volatile organic compounds from bacteria implicated in ventilator- associated pneumonia analysed by TD-GCIMS," Journal of breath research, 2(2): p. 026002, Jan. 2018.
Liu et al., "An Electronic Nose Based Beverage Identification using an Improved Fisher Discriminate Analysis Method," International Journal of Simulation Systems, Science & Technolo, vol. 18 2 :9.1-9.6, Jun. 2017.
Manicke, N. E.; Belford, M., "Separation of Opiate Isomers Using Electrospray Ionization and Paper Spray Coupled to High-Field Asymmetric Waveform Ion Mobility Spectrometry," J. Am. Soc. Mass Spectrom. 2015, 26 (5), 701-705.
Myung, S., et al., "Coupling Desorption Electrospray Ionization with Ion Mobility/Mass Spectrometry for Analysis of Protein Structure: Evidence for Desorption of Folded and Denatured States," J. Phys. Chem. B 2006, 110 (10), 5045-5051.
Overmycr KA, Shishkova E, Miller IJ, et al., "Large-scale Multi-omic Analysis of COVID-19 Severity," Cell Syst 2020; 12:23-40.
Pizzini, A., et al., "Analysis of volatile organic compounds in the breath of patients with stable or acute exacerbation of chronic obstructive pulmonary disease," Journal of breath research, Mar. 2018.
Ranninger C, et al., "Improving global feature detectabilities through scan range splitting for untargeted metabolomics by high-performance liquid chromatography-Orbitrap mass spectrometry," Anal Chim Acta 2016; 930: 13-22.
Rattray, N.J.W., et al., "Taking your breath away: metabolomics breathes life in to personalized medicine," Trends in Biotechnology, 32(10): p. 538-548, Oct. 2014.
Rohart F, et al., "mixOmics: An R package for 'omics feature selection and multiple data integration," PLoS Comput Biol 2017; 13. 001: 10.1371/journal.pcbi.1005752.
Rosier, E., et al., "Development and validation of a new TD-GCIMS method and its applicability in the search for human and animal decomposition products," Analytical and bioanalytical chemistry, 2014. 406(15): p. 3611-3619.
Ruszkiewicz OM, Sanders D, O'Brien R, et al., "Diagnosis of COVID-19 by analysis of breath with gas chromatography-ion mobility spectrometry—a feasibility study," EClinicalMedicine 2020.
Sariol, H.C., et al., "Characterization of the exhaustion profile of activated carbon in industrial rum "filters" based on TGA, TD-GCIMS, colorimetry and NMR relaxometry," Materials Today Communications, 11: p. 1-10, Feb. 2017.
Shetage SS, et al., "Application of sebomics for the analysis of residual skin surface components to detect potential biomarkers of type-1 diabetes mellitus," Sci Rep 2017; 7: 1-8.

(56) References Cited

OTHER PUBLICATIONS

Shirasu, M. and K. Touhara, "The scent of disease: volatile organic compounds of the human body related to disease and disorder," The Journal of Biochemistry, 2011. 150(3): p. 257-266, Jul. 2011.
Song JW, Lam SM, Fan X, et al., "Omics-Driven Systems Interrogation of Metabolic Dysregulation in COVID-19 Pathogenesis," Cell Metab 2020; 32: 188-202.e5.
Struwe W, et al., "The COVID-19 Ms Coalition-accelerating diagnostics, prognostics, and treatment," Lancet 2020; 395: 1761-2.
Takats, Z., et al.., "Mass Spectrometry Sampling Under Ambient Conditions with Desorption Electrospray Ionization," Science (Washington, DC, U. S.) 2004, 306 (5695), 471-473.
Wagner J., ct al., "Absolute lymphocyte count is a prognostic marker in Covid-19: A retrospective cohort review," Int J Lab Hematol 2020; n/a. 001:10.1111/ijlh.13288.
Wenham C., et al., "COVID-19: the gendered impacts of the outbreak," Lancet 2020; 395: 846-8.
Wei X, et al., "Hypolipidemia is associated with the severity of COVID-19," J Clin Lipidol 2020; 14: 297-304.
Wikoff, W.R., et al., "Metabolomics analysis reveals large effects of gut microflora on mammalian blood metabolites," Proceedings of the National Academy of Sciences, 106(10): p. 3698-3703, Mar. 2009.
Who. "Who advice for international travel and trade in relation to the outbreak of pneumonia caused by a new coronavirus in China," 2019. https://www.who.int/news-room/articles-detail/who-advice-for-international-travel-and-trade-in-relation-to-the-outbreak-of-pneumonia-caused-by-a-new-coronavirus-in-china (accessed Jul. 27, 2020).
WHO. Novel Coronavirus—China. 2020. https://www.who.int/csr/don/12-january-2020-novel-coronavirus-china/en/ (accessed Jul. 27, 2020).
WHO. "Simulation of the effects of COVID-19 testing rates on hospitalizations," https://www.who.int/bulletin/volumes/98/5/20-258186/en/ (accessed Sep. 29, 2020).
Wood-Kaczmar, A., S. Gandhi, and N. Wood, "Understanding the molecular causes of Parkinson's disease," Trends in molecular medicine, 12(11): p. 521-528, Oct. 2006.
Wu D, Shu T, Yang X, et al., "Plasma metabolomic and lipidomic alterations associated with COVID-19," Natl Sci Rev 2020; 7: 1157-68.
Xie, J., et al., "Analysis of changes in volatile constituents and expression of genes involved in terpenoid metabolism in oleocellosis peel," Food chemistry, 243: p. 269-276, Sep. 2018.
Yap BW, et al., "Comparisons of various types of normality tests," J Stat Comput Simul 2011; 81: 2141-55.
Zhang et al., "Development of a Paper Spray Mass Spectrometry Cartridge with Integrated Solid Phase Extraction for Bioanalysis," Analytical Chemistry, vol. 87:6212-6219, May 2015.
International Search Report and Written Opinion for International Application No. PCT/GB2021/050269, entitled Biomarkers and Uses Thereof, consisting of 16 pages. Date Mailed May 12, 2021.
Trivedi, D. K., "Discovery of Volatile Biomarkers of Parkinson's Disease from Sebum," ACS Cent. Sci. 2019, 5, pp. 599-606 (2019).
Sarkar, D., et al., "Rapid Diagnosis of Parkinson's Disease from Sebum using Paper Spray Ionisation flon Mobility Mass Spectrometry," pp. 1-16, [Retrieved from the Internet: URL:http://itempdf74155353254prod.s3.amazonaws.com/12517385/Rapid Diagnosis of Parkinson's Disease from Sebum using Paper Spray Ionisation Ion Mobility-Mass Spectrometry-vl.pdf] [retrieved on Apr. 29, 2021] (2020).
Sinclair, E., et al., "Sebum: a window into dysregulation of mitochondrial metabolism in Parkinson's disease," pp. 1-20 [Retrieved from the Internet: URL:https://chemrxiv.org/articles/preprint /Sebum A Window into Dysregulation of Mito chondrTaT Metabolism-in Parkinson s DTseas e/11603613/1] [retrieved on Apr. 29, 2021] Preprint (2020).
Sinclair, E., et al., "Sebum: a window into dysregulation of mitochondrial metabolism in Parkinson's disease," pp. 1-32 ChemRxiv, [Retrieved from the Internet: URL:https://chemrxiv.org/articles/preprint /Sebum A Window into Dysregulation of Mito chondrTaT Metabolism-in Parkinson s DTseas e/11603613/1] [retrieved on Apr. 29, 2021] (2020).
Morgan, J., "Joy of super smeller: sebum clues for PD diagnostics", Lancet Neurology, Lancet Publishing Group, London, GB, vol. 15, No. 2, pp. 138-139, (2016).
Ohene, A., "Paws for thought: dogs sniff out Parkinson's disease with 90% hit rate," Parkinson's Life, Retrieved from the Internet: URL:https://parkinsonslife.eu/paws-for-thought-dogs-sniff-out-parkinsons-disease-with-90-hit-rate/ [retrieved on Oct. 25, 2018] (2016).
Calvano, et al., "Searching for Potential Lipid Biomarkers of Parkinson's Disease in Parkin-Mutant Human Skin Fibroblasts by HILIC-ESI-MS/MS: Preliminary Findings," Int. J. Mol. Sci. 2019, 20, 3341.
Leaptrot, et al., "lon mobility conformational lipid atlas for high confidence lipidomics," Nature Communications, (2019) 10:985.
SPETZLER2: AU-2011291599-A1 (Year: 2013).
Camera, et al., "Comprehensive analysis of the major lipid classes in sebum by rapid resolution high-performance liquid chromatography and electrospray mass spectrometry," Journal of Lipid Research, vol. 51, 2010, pp. 3377-3388.

* cited by examiner

| Correct classification rate 85% | Observed Control | Observed PD |
|---|---|---|
| Predicted Control | 0.67 | 0.33 |
| Predicted PD | 0.10 | 0.90 |

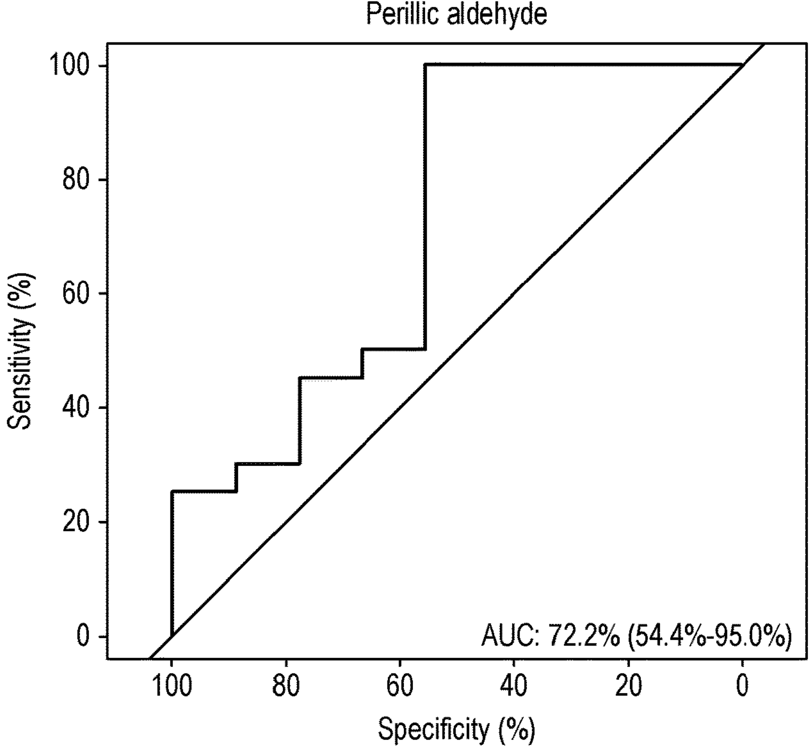
FIG. 2A(i)
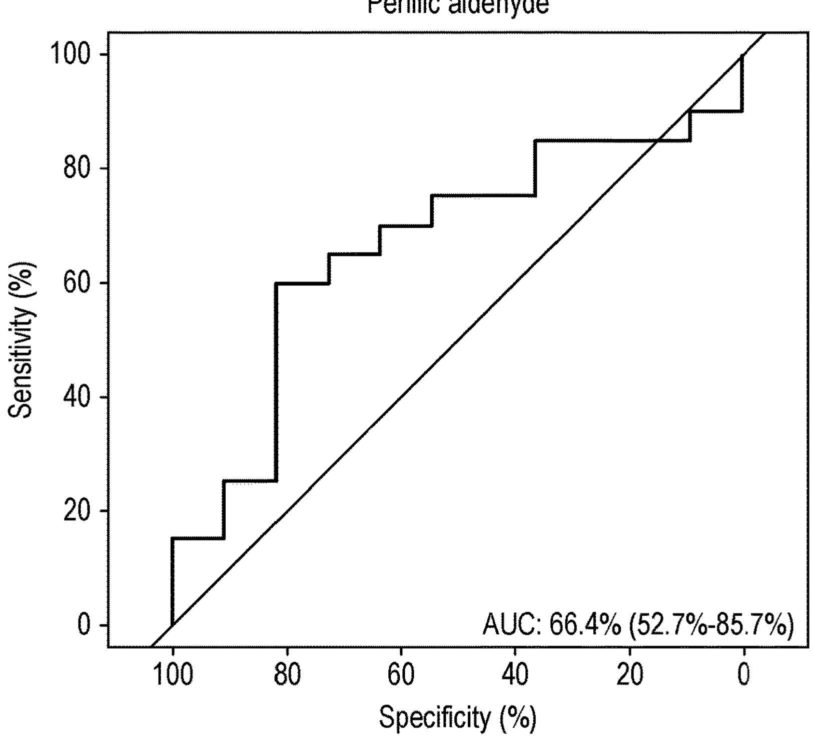
FIG. 2A(ii)

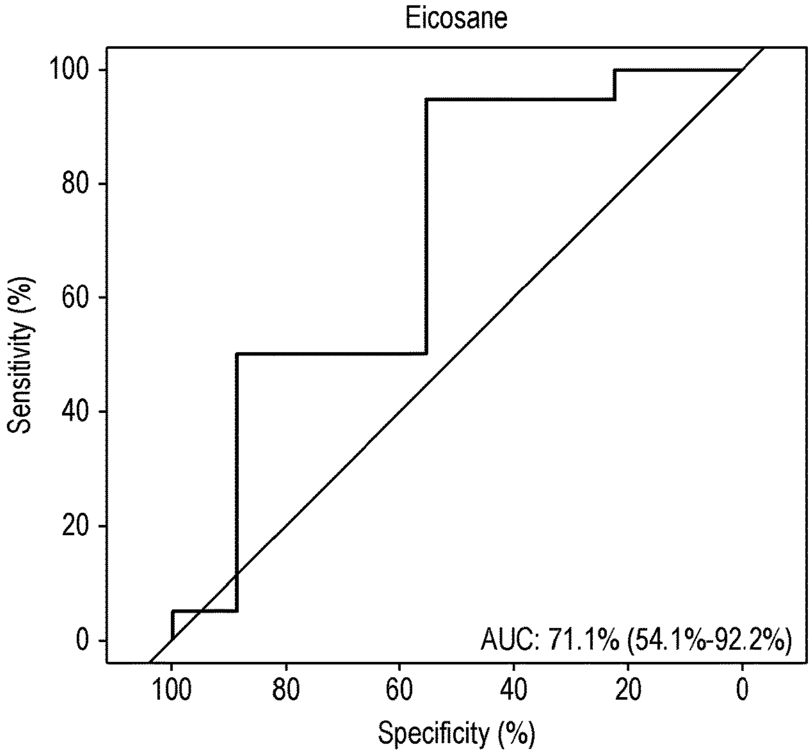
FIG. 2A(iii)
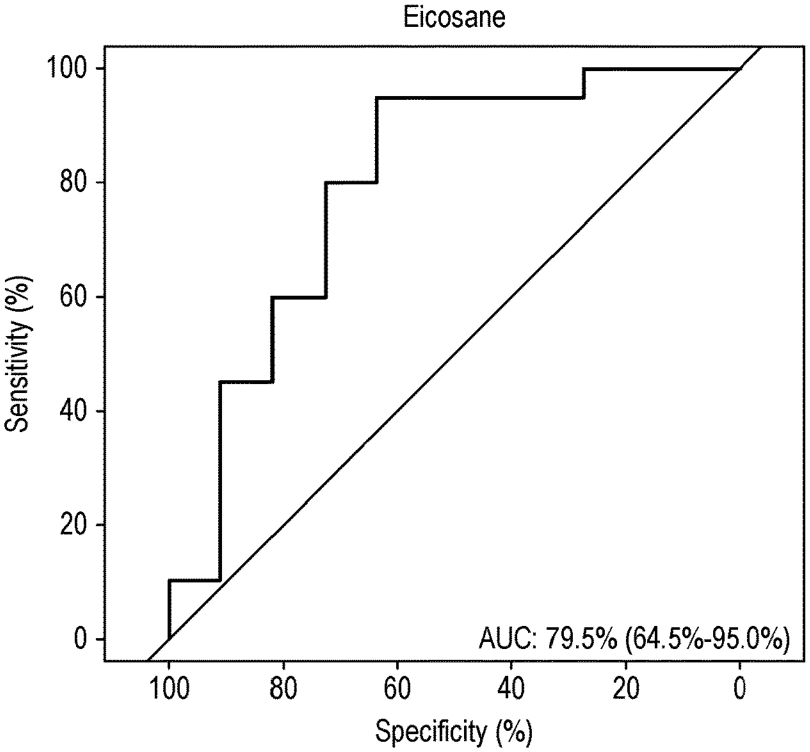
FIG. 2A(iv)

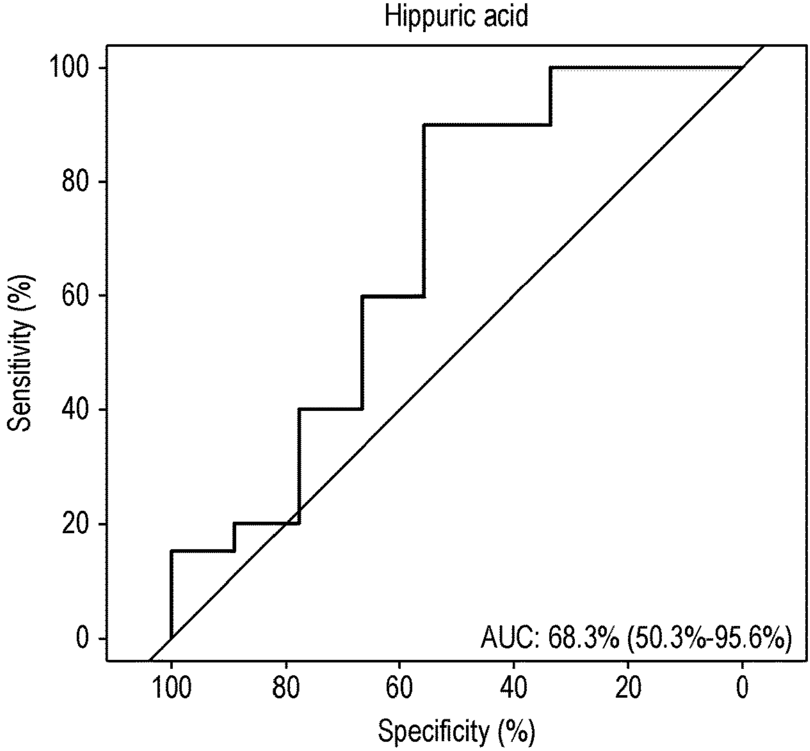
FIG. 2A(v)
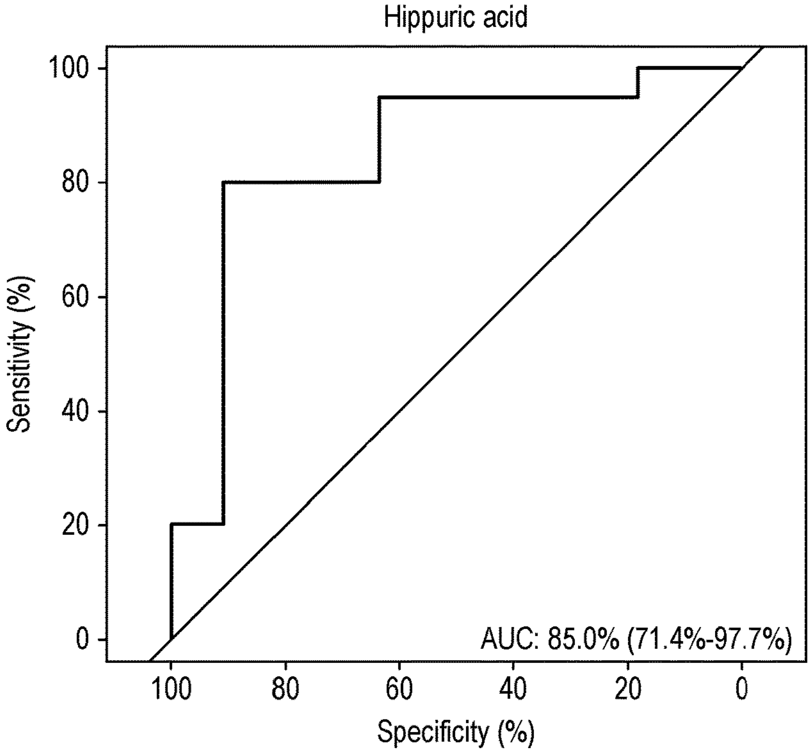
FIG. 2A(vi)

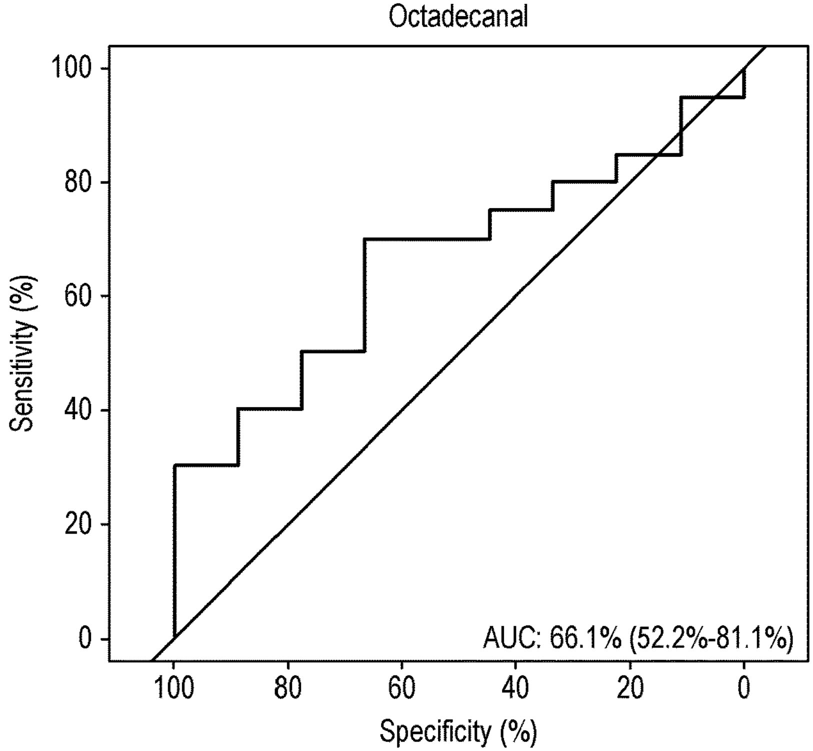
FIG. 2A(vii)
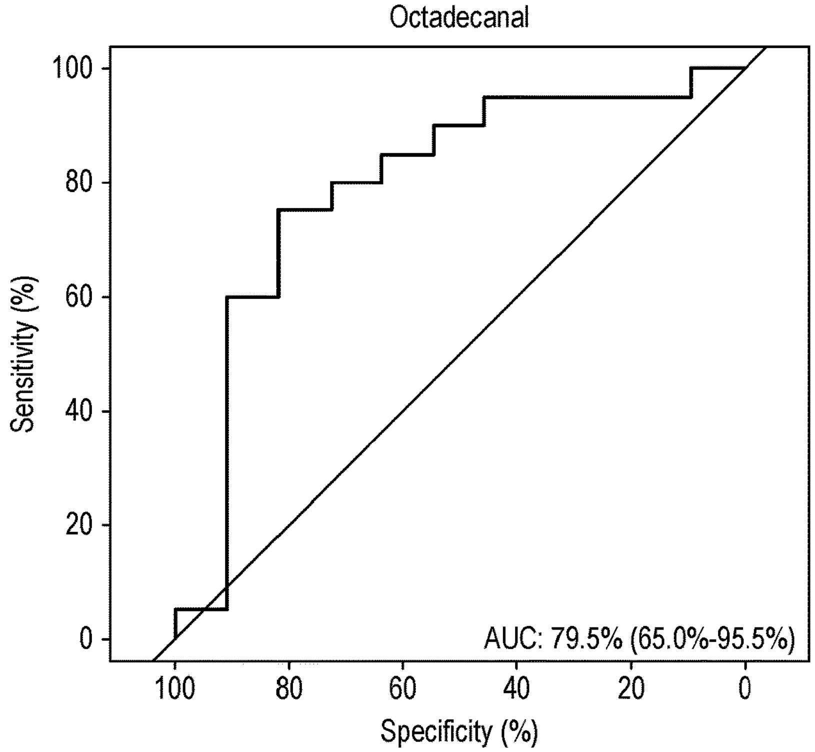
FIG. 2A(viii)

Intensity
m/z
1592.38

Intensity
m/z
365.29

Intensity
m/z
1503.28

Intensity
m/z
1618.49

METHOD FOR DETECTING AND TREATING PARKINSON'S DISEASE COMPRISING SEBUM BIOMARKERS

This application is the U.S. National Stage of International Application No. PCT/GB2021/050269, filed Feb. 5, 2021, which designates the U.S., published in English, and claims priority under 35 U.S.C. § 119 or 365 (c) to Great Britain Application No. 2001570.7, filed Feb. 5, 2020. The entire teachings of the above applications are incorporated herein by reference.

TECHNICAL FIELD OF THE INVENTION

The present invention relates to methods for detecting the presence or absence of Parkinson's Disease (PD).

BACKGROUND TO THE INVENTION

Parkinson's disease (PD) is a progressive, neurodegenerative disease, the diagnosis of which, at present, is informed by observation and measurement of clinical symptoms. The most important clinical symptom of PD is a reduction in the speed and amplitude of movement. Other symptoms including stiffness and tremor are also common [1]. There is an exigent need to detect PD before manifestation of such clinical symptoms as these are predominantly observable only once the disease has progressed to a stage when more than 60% of the dopaminergic neurons in the *Substantia nigra* are lost [2].

More than 1 in 40 people will develop Parkinson's disease (PD) at some point in their life. The symptoms of PD worsen as the disease progresses, and since the majority of these symptoms are only detected once the neurodegenerative process is already well advanced, there is little opportunity for early interventions. This is also attributable to a limited understanding of the causation of PD at the molecular level coupled with clinical variations in signs and symptoms that occur in the early stages of PD [4].

Early pilot studies with a 'Super Smeller' have indicated that a distinct musky odour was associated with the sebum from PD subjects [3]. This Super Smeller has demonstrated a unique ability to detect PD by odor [2]. They have an extremely sensitive sense of smell, and this enables them to detect and discriminate odors not normally detected by those of average olfactory ability. Preliminary tests with t-shirts and medical gauze indicated the odor was present in areas of high sebum production, namely the upper back and forehead, and not present in armpits, that are more commonly associated with human odor [2]. Over-production of sebum, seborrhoea, is a known non-motor symptom of PD [5], and Parkinson's skin has recently been shown to contain phosphorylated α-synuclein, a molecular hallmark of PD [6]. Identification and quantification of the metabolites that are associated with this distinctive PD odor could enable rapid, early screening of PD as well as provide insights into molecular changes that occur at disease onset and enable stratification of the disease in future.

Volatile organic compounds (VOCs) generally are associated with characteristic odors, although some volatiles may also be odorless [7]. Volatilome (volatile metabolites) analysis using mass spectrometry has been used for medical diagnostics [8-12] as well as for analysis of the quality of food such as oils and honey [13-15], beverages [16] and in the health and beauty industry [17]. TD-GC-MS has been used as a volatilome analysis platform for the detection of bacteria implicated in ventilator associated pneumonia [11], for differentiation between human and animal decomposition [18], for characterisation of exhaustion profile of activated carbon [19] as well as aerosol detection from e-cigarettes [20].

It is an object of the present invention to address one or more problems associated with identification of PD. It is also an object of the present invention to provide a new method of diagnosing and/or identifying those individuals who may be suffering from, or have an early onset of, PD. It would be preferred if a method of diagnosis could be provided, which is non-invasive and which can be performed by a range of healthcare professionals or carers.

SUMMARY OF INVENTION

In accordance with a first aspect of the present invention, there is provided a method for detecting the presence or absence of Parkinson's disease (PD) in a subject, the method comprising:

(a) providing a sebum sample from the subject;
(b) determining the level of one or more biomarker compounds in the subject's sebum sample;
(c) comparing the level of the one or more biomarker compounds in the subject's sebum sample to a control sebum level of the biomarker compounds; and
(d) detecting the presence or absence of PD in the subject based on the difference between the level of the one or more biomarker compounds in the subject's sample and the control level.

The method will preferably be used for detecting the presence or absence of prodromal symptoms of PD and/or presence or absence of early onset PD.

There is a general prejudice in the art against using sebum as a biofluid for diagnostics due to the non-sterile environment of the skin and potential contaminants (such as soaps) which may be present and affect test results. However, the inventors have advantageously and unexpectedly found that molecules present on skin surface can be used to distinguish individuals having Parkinson's Disease from a Control subject. The inventors have further been able to identify molecules which indicate prodromal symptoms of PD and/or presence or absence of early onset PD. Using a sebum sample to assess the Parkinson's Disease status of an individual is advantageous for a number of reasons. Firstly, collecting sebum is a non-invasive method. Secondly, it should be possible to directly sample, and analyse sebum without preparation and extraction of metabolites from sebum and therefore provide opportunities to develop a rapid screening/diagnostic test for Parkinson's Disease. Such tests could be utilised as a companion diagnostic alongside the treatment with neuroprotective agents so as to delay the onset of Parkinson's Disease or attenuate its progression in an individual. Parkinson's Disease affects an ageing population globally and a diagnostic test that is non-invasive would be well received by numerous public and private healthcare providers across the globe.

In certain preferred embodiments, the method comprises the identification that one or more of the volatile compounds are elevated or reduced with reference to a control sebum value. It will be apparent to the skilled addressee that the control sebum value would typically be the value in a healthy individual or an individual who is deemed not to be suffering from Parkinson's Disease. Alternatively, the control sebum value could be the value of the individual when they are responding to a therapy as often individuals initially respond well to treatment, but then need to have their doses increased or their therapies switched to a different therapeutic over time as the disease progresses.

The one or more differentiated compounds present in sebum may comprise at least one or more lipids, cardiolipins, phosopholipids, glycerophospholipids glycolipids, sphingolipids, ceramides, sphingomyelin, fatty acids, waxy esters.

The one or more volatile compounds may comprise one or more selected from the following: dodecane, eicosane, octacosane, hippuric acid, octadecanal, artemisinic acid, perillic aldehyde (also known as Perillaldehyde, or perilla aldehyde), diglycerol, hexyl acetate, 3-hydroxytetradecanoic acid and/or octanal.

In certain preferred embodiments the method comprises the identification that one or more of the following as occurred: perillic aldehyde is reduced; hippuric acid is elevated; eicosane is elevated; and/or octadecanal is elevated.

The one or more biomarker compounds preferably comprise lipids. The lipids may have a molecular mass of ≥ about 700 Da.

The lipids may comprise cardiolipins and/or phosphatidylcholines. The method may comprise the identification that the level of the one or more cardiolipins and/or phosphatidylcholines are elevated relative to the control level.

The term, "volatile compound" is intended to mean a compound which easily becomes a vapor or gas when isolated and/or subjected to mass spectrometry.

The method may be used for assessing whether an individual has early onset Parkinson's Disease (PD) which is often very difficult to assess. The method may also be used for assessing (or continually assessing) individuals who have a hereditary and/or environmental risk of developing Parkinson's Disease.

Unexpectedly, the inventors have found that not all typical solvents are suitable in the extraction of volatile compounds from sebum. It has been identified that the volatile compounds in the sebum are best extracted using methanol.

It will be apparent to the skilled addressee that a number of methods for identifying and/or quantifying the sebum based compounds may be employed.

Generally, mass spectrometry (MS) may be used to detect, identify and/or quantify analytes (such as volatile compounds) in complex matrices, such as biological samples, usually as part of a hyphenated technique, for example liquid chromatography (LC)-MS or gas chromatography (GC)-MS. As such, conventional MS ionization sources such as electrospray (ES) and chemical ionization (CI), respectively, are suitable. Other ionization sources are known.

Preferably, the method comprises thermal desorption-gas chromatography mass spectrometry.

If MS is used for identifying and/or quantifying the sebum based compounds, preferably, it is used to identify compounds in the significantly higher molecular mass region of ≥800 m/z, ≥1000 m/z, or ≥1200 m/z. Typically, biofluids (such as blood and urine) assess compounds in the lower molecular mass region of ≥1000 m/z. The present inventors have surprisingly for the first time, shown that sebum can be used as a sampling biofluid for PSI-MS and that it enables the detection of skin surface molecules with a significantly higher molecular mass of ≥800 m/z. Ion mobility-mass spectrometry (IM-MS) was also employed by the inventors to further evaluate these high molecular weight metabolites and the mass spectra of human sebum surprisingly showed the presence of four envelopes at the higher mass region (m/z 800-2500) consisting of singly charged peaks.

For routine clinical laboratories and point of care applications, for example, there is a desire to reduce sample pre-treatment and/or simplify analysis and/or data interpretation. Hence, ambient ionization sources may be preferred, for example desorption electrospray ionization (DESI), direct analysis in real time (DART), atmospheric solids analysis probe (ASAP) and paper spray (PS).

Paper spray is a direct sampling ionization method for mass spectrometry, including of complex mixtures. A sample, for example 0.4 μL, is loaded onto a triangular piece of paper and wetted with a solvent, for example 10 μL of methanol:water. Ions from the sample are generated by applying a high voltage, for example 3-5 kV DC or 4 to 6 kV DC, to the paper. By directing the ions generated at the apex of the paper towards an inlet of a mass spectrometer, mass spectrometry thereof may be performed.

In one example, the mass spectrometry is performed using a mass spectrometer comprising an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) an Atmospheric Solids Analysis Probe ("ASAP") ion source; (xxviii) a Laser Ablation Electrospray Ionisation ("LAESI") ion source; (xxix) a Desorption atmospheric pressure photoionization ("DAPPI") ion source; (xxx) paper spray ("PS"). Paper spray is preferred.

The present inventors have advantageously demonstrated the versatility of thermal desorption-gas chromatography mass spectrometry (TD-GC-MS) as a tool for studying volatile compounds, and its applicability to identifying the metabolites that cause the distinct scent of PD in sebum.

The sebum may be collected and stored in a number of ways. For example, the sebum may be collected by swabbing the back of an individual with a medical gauze, absorbent paper or cotton wool. Alternatively, the sebum may be scraped off the back of an individual using a rigid implement such as a spatula and then deposited in a collection tube or other device. Generally speaking, the sebum is relatively stable at ambient temperatures so no further treatment of the sebum is necessary before the extraction of the volatile compounds. However, if desired, the sebum may be mixed with a suitable preserver or buffer before extraction.

In certain embodiments, there is provided a smart paper envelope that can be used to collect sebum sample, non-invasively and posted back to a laboratory which can then directly analyse sample off the paper using very small amount of extraction solvents and provide the results shortly thereafter.

The method may further comprise drying the mixture. The mixture may be dried by means of a vacuum concentrator such as a SpeedVac Concentrator.

The sebum may be on any number of different substrates, such as any textile cellulose medium or fabric or artificial surface. Preferably, the sebum may be on a cotton swab, gauze, wood or cellulose based paper.

The target analytes may comprise one or more volatile compounds, such as one or more selected from the following: dodecane, eicosane, octacosane, hippuric acid, octadecanal or dodecane, artemisinic acid, perillic aldehyde or diglycerol, hexyl acetate or dodecane, and 3-hydroxytetradecanoic acid or octanal. Or of the class of compounds found in sebum comprising one or more selected from lipids, cardiolipins, phosopholipids, glycerophospholipids glycolipids, sphingolipids, ceramides, sphingomyelin, fatty acids, waxy esters or phosphatidylcholines.

In accordance with another aspect of the present invention, there is provided a method for detecting the presence of and treating Parkinson's disease (PD) in a subject, the method comprising:

(a) providing a sebum sample from the subject;
(b) determining the level of one or more biomarker compounds in the subject's sebum sample;
(c) comparing the level of the one or more biomarker compounds in the subject's sebum sample to a control sebum level of the biomarker compounds;
(d) detecting the presence of PD in the subject based on the difference between the level of the one or more biomarker compounds in the subject's sample and the control level; and
(e) administering a therapeutically effective amount of a neuroprotective agent to the subject.

In accordance with yet a further aspect of the present invention, there is provided a method for detecting the presence of and treating Parkinson's disease (PD) in a subject, the method comprising:

(a) providing a sebum sample from the subject;
(b) determining the level of one or more biomarker compounds in the subject's sebum sample;
(c) comparing the level of the one or more biomarker compounds in the subject's sebum sample to a control sebum level of the biomarker compounds;
(d) detecting the presence of PD in the subject based on the difference between the level of the one or more biomarker compounds in the subject's sample and the control level; and
(e) administering a therapeutically effective amount of a neuroprotective agent to the subject.

In a yet further aspect of the present invention, there is provided a device for detecting the presence or absence of Parkinson's disease (PD) in a subject, the device comprising:

(a) means for receiving a sebum sample from the subject;
(b) means for determining the level of one or more biomarker compounds in the subject's sebum sample;
(c) means for comparing the level of the one or more biomarker compounds in the subject's sebum sample to a control sebum level of the biomarker compounds; and
(d) means for producing an output informing a user of the presence or absence of PD in the subject based on the difference between the level of the one or more biomarker compounds in the subject's sample and the control level.

Preferably, the means for determining the level of the one or more biomarker compounds in the subject's sebum sample comprises means for performing thermal desorption-gas chromatography mass spectrometry or paper spray ionization-ion mobility mass spectrometry.

In yet a further aspect of the present invention, there is provided a kit for detecting the presence or absence of Parkinson's disease (PD) in a subject, the kit comprising:

(a) means for obtaining a sebum sample from a subject;
(b) means for determining the level of one or more biomarker compounds in the subject's sebum sample;
(c) means for comparing the level of the one or more biomarker compounds in the subject's sebum sample to a control level of the biomarker compounds; and
(d) means for producing an output informing a user of the presence or absence of PD in the subject based on the difference between the level of the one or more biomarker compounds in the subject's sample and the control level.

The means in the kit for obtaining a sebum sample from a subject comprises medical gauze, absorbent paper, cotton wool or a rigid implement.

Features, integers, characteristics, compounds, methods, assays and devices described in conjunction with a particular aspect, embodiment or example of the invention are to be understood to be applicable to any other aspect, embodiment or example described herein unless incompatible therewith. All of the features disclosed in this specification (including any accompanying claims, abstract and figures), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

DETAILED DESCRIPTION OF THE INVENTION

Aspects and embodiments of the present invention will now be illustrated, by way of example, with reference to the accompanying figures. Further aspects and embodiments will be apparent to those skilled in the art. All documents mentioned in this text are incorporated herein by reference.

FIG. 1 shows the PLS-DA classification model (A.) PLS-DA predictions showing 90% correct prediction of Parkinson's sample classifications with validation using 5-fold cross validation. (B.) PLS-DA modelling was further tested using permutation tests (where the output classification was randomised; n=26) and results are plotted as a histogram which shows frequency distribution of correct classification rate (CCR) which yielded CCRs ranging between 0.4 to 0.9 for permutated models. The observed model was significantly better than most of the permuted models ($p<0.1$); shown by arrow;

FIG. 2 shows ROC curves, box plots and AUC comparison for analytes of interest (A.) ROC curves for both discovery ((i), (iii), (v) and (vii)) and validation ((ii), (iv), (vi) and (viii)) cohort for four analytes common to both experiments. Numbers in parenthesis are confidence intervals calculated computed with 2000 stratified bootstrap replicates and grey line represents random guess. (B.) Box plot for both discovery and validation cohort for four analytes in common, comparing the means on log scaled peak areas of these analytes. (C.) AUC comparison between analytes;

FIG. 3 shows olfactograms from control and PD gauzes GC-MS chromatogram from three drug naïve Parkinson's subjects and a blank gauze overlaid by red shaded area shows overlap between real time GC-MS analysis and smell using odor port. Figure shows retention time between 10 and 21 min where the Super-Smeller had described odors linked to various peaks. The highlighted area between 19.2 and 21 minutes (enlarged on right) is of particular interest as 3 out of 4 compounds overlap with odor port results, where the Super-Smeller described the scent of PD to be very strong. The peaks are not seen in a blank gauze at the same time window as shown by normalised relative peak intensities to the highest peak in each chromatogram;

FIG. 4 shows ROC plots. (A.) ROC plot generated using combined samples from both cohorts and all five metabolites that were common and differential between control and PD. The shaded area indicates 95% confidence intervals calculated by Monte Carlo Cross Validation (MCCV) using balanced sub-sampling with multiple repeats. (B.) ROC plots generated using all nine metabolites that were common between the two cohorts (but not necessarily differential using Student's t-test or expressed in the same direction between cohorts). Each model was built using PLS-DA to rank all variables and top two important variables were selected to start with. Then in each subsequent model additional variables by rank were added to generate ROC curve. Confidence intervals were calculated by Monte Carlo Cross Validation (MCCV) using balanced sub-sampling with multiple repeats.

Figure 15A:
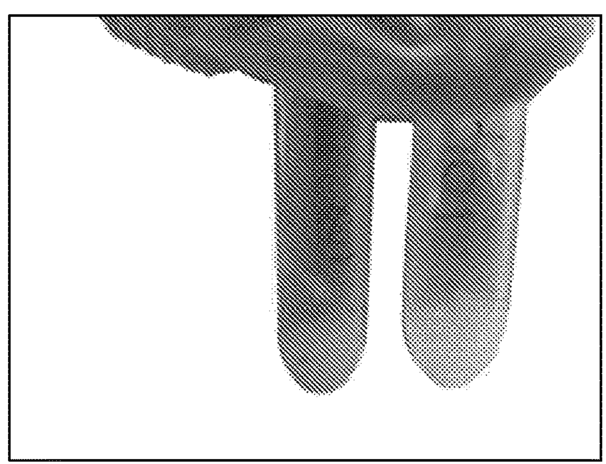
Figure 15B:
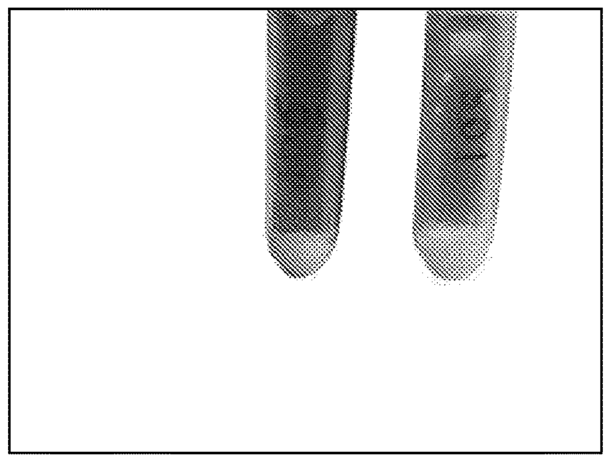
Figure 15C:
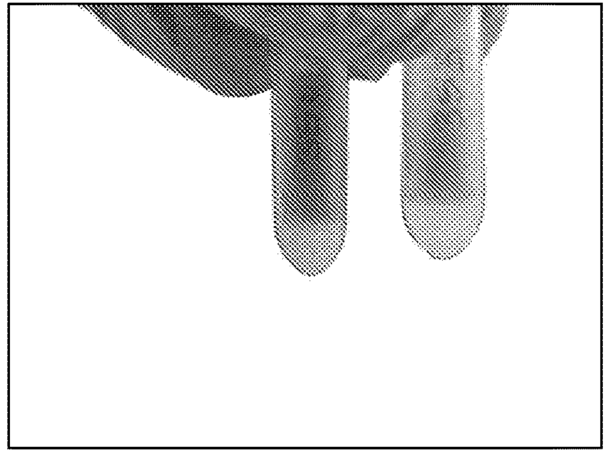
Figure 16:
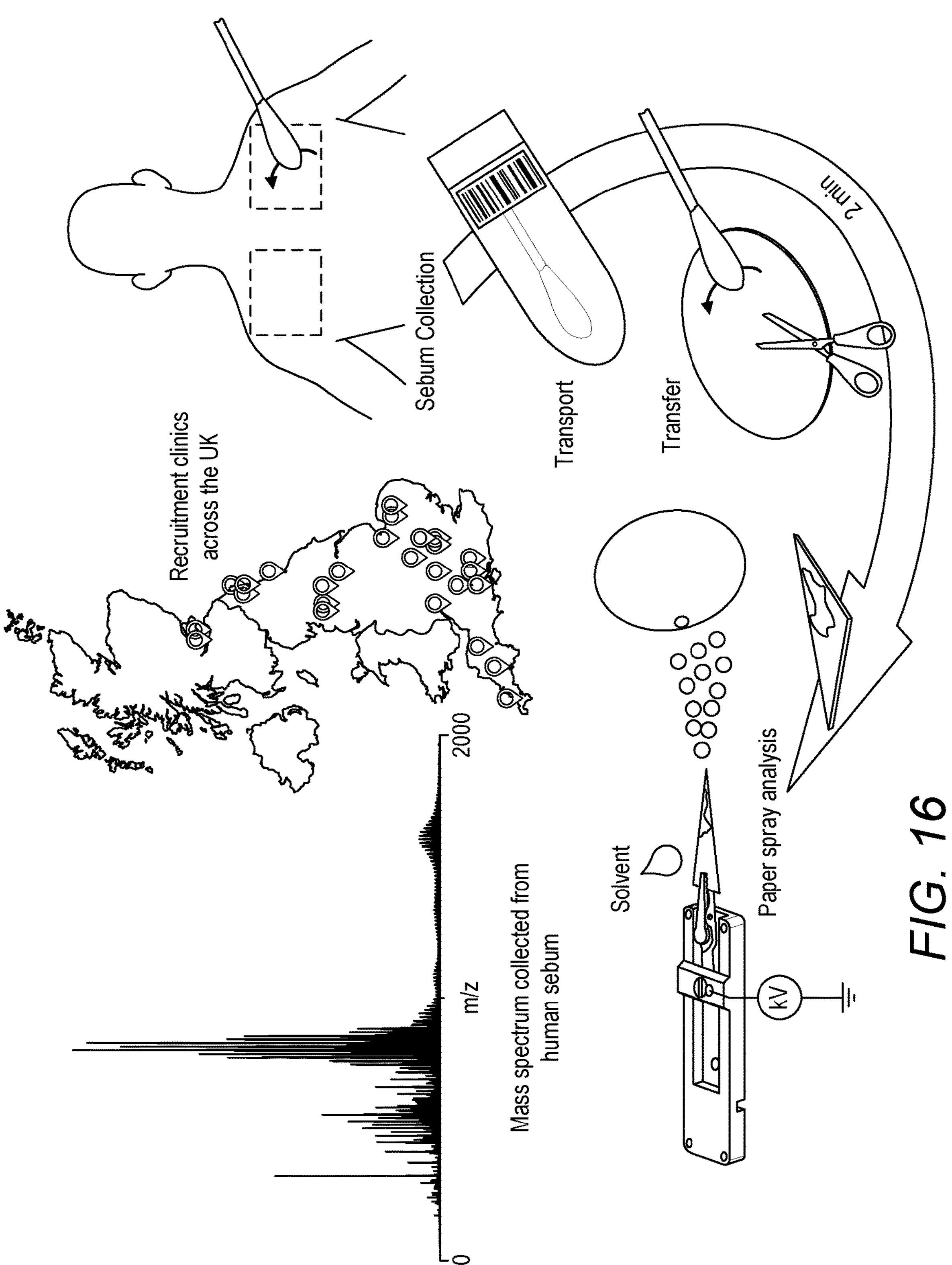
Figure 17B:
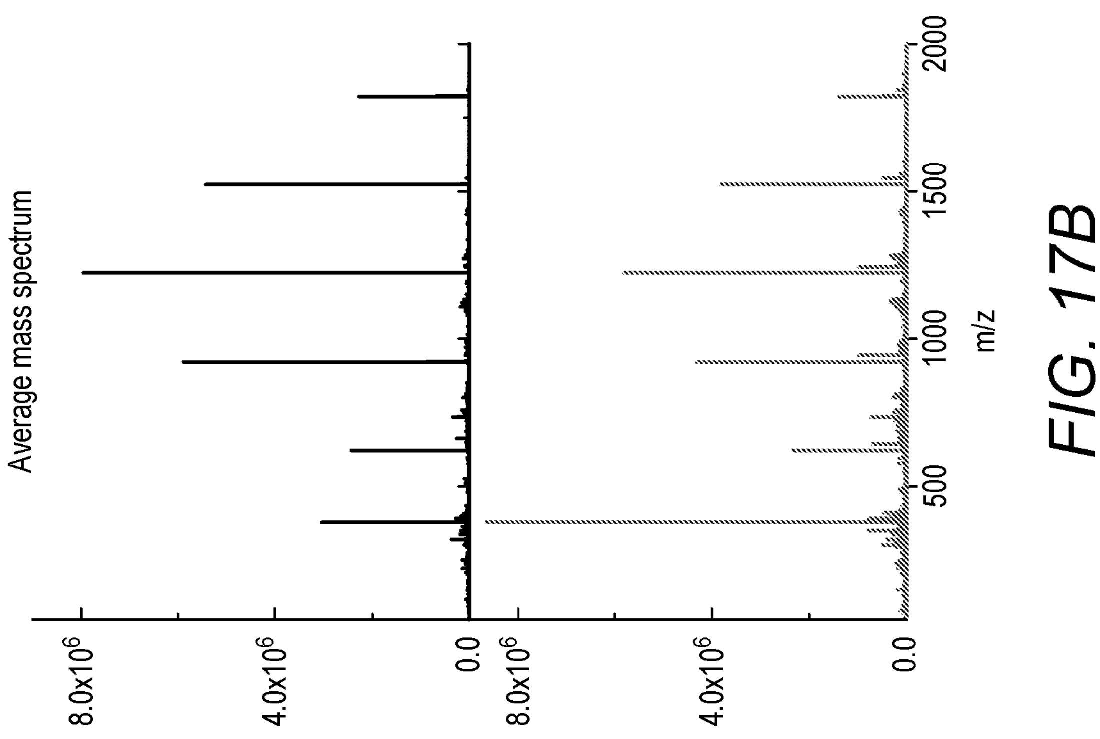
Figure 17A:
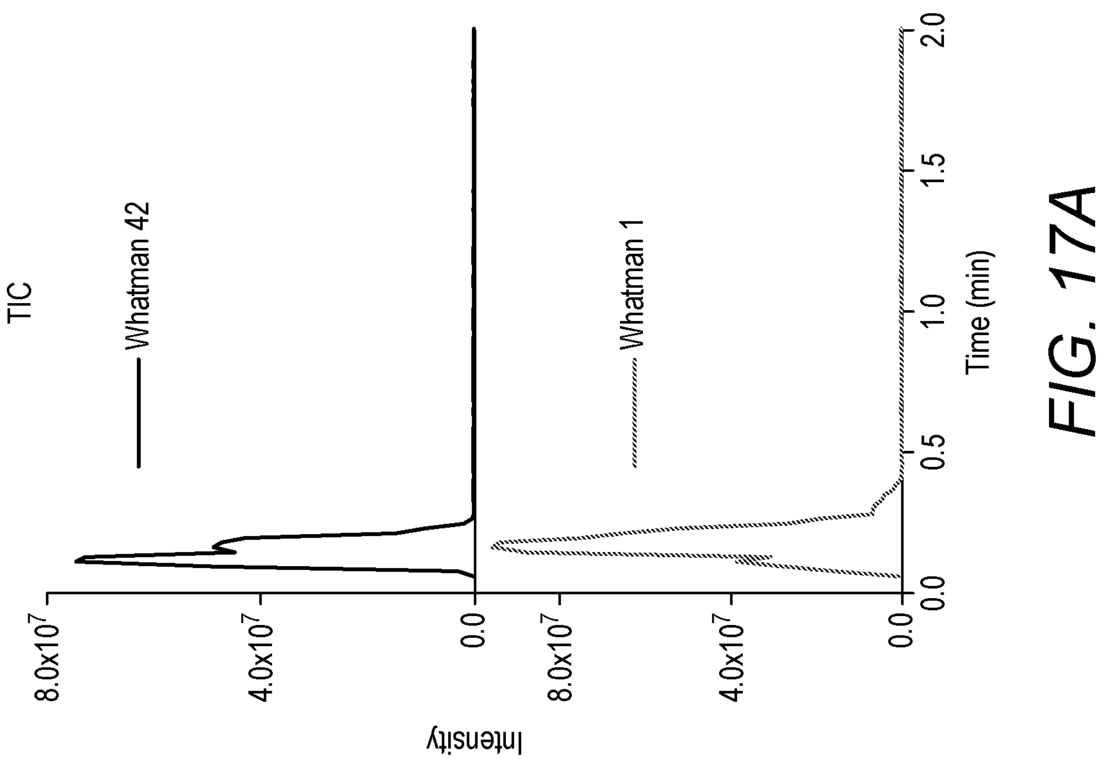
Figure 19:
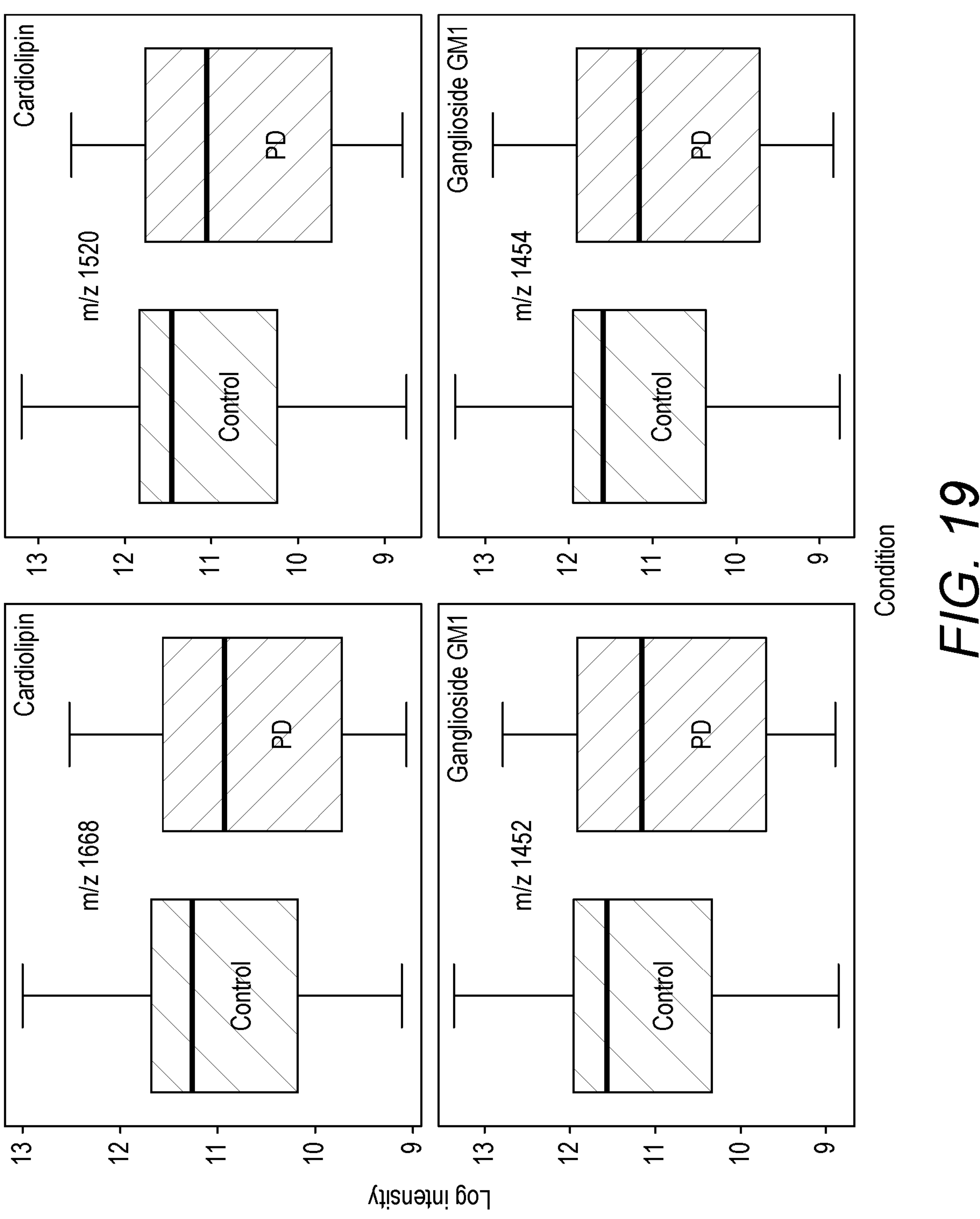
Figure 20:
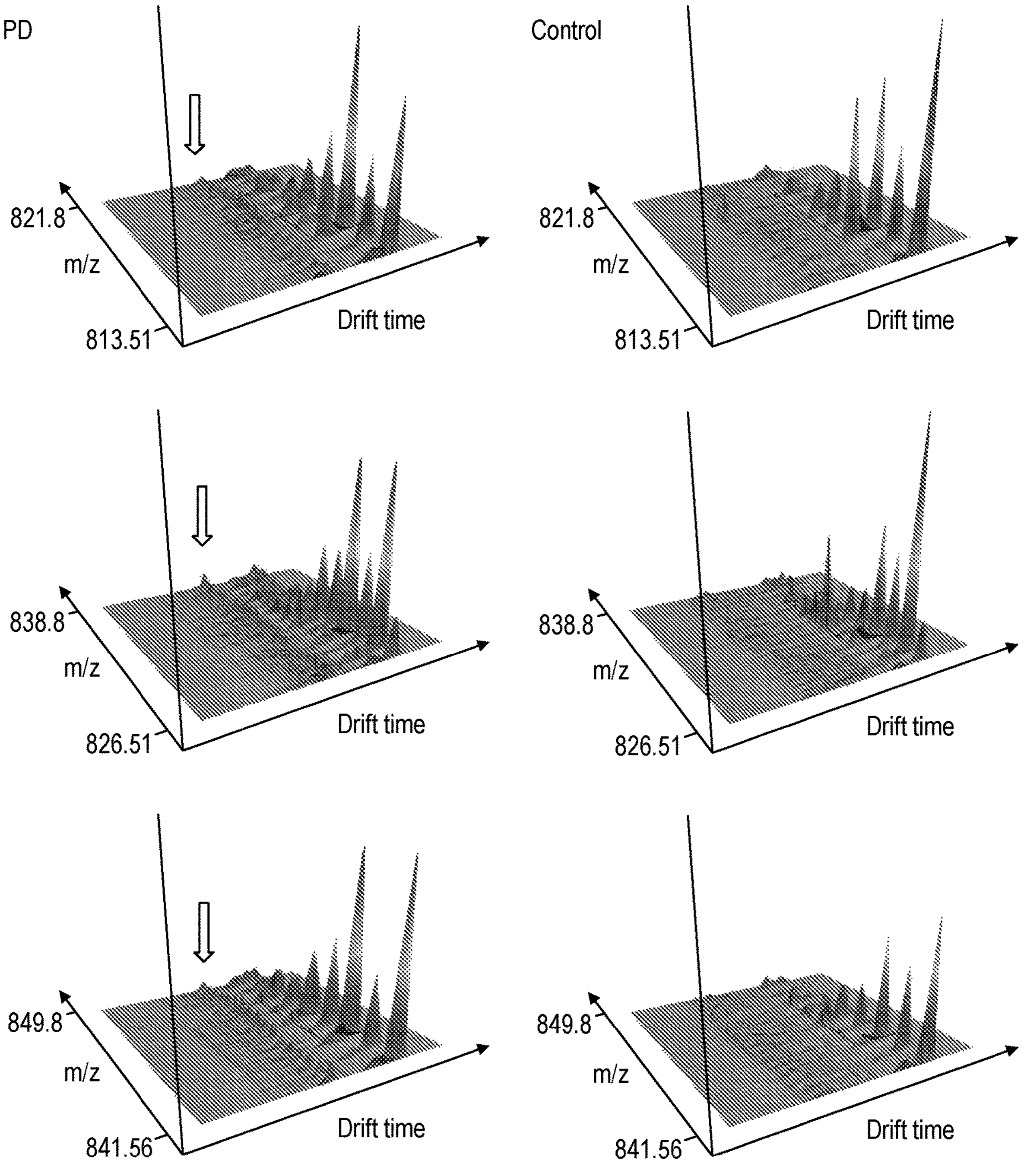
Figure 20:
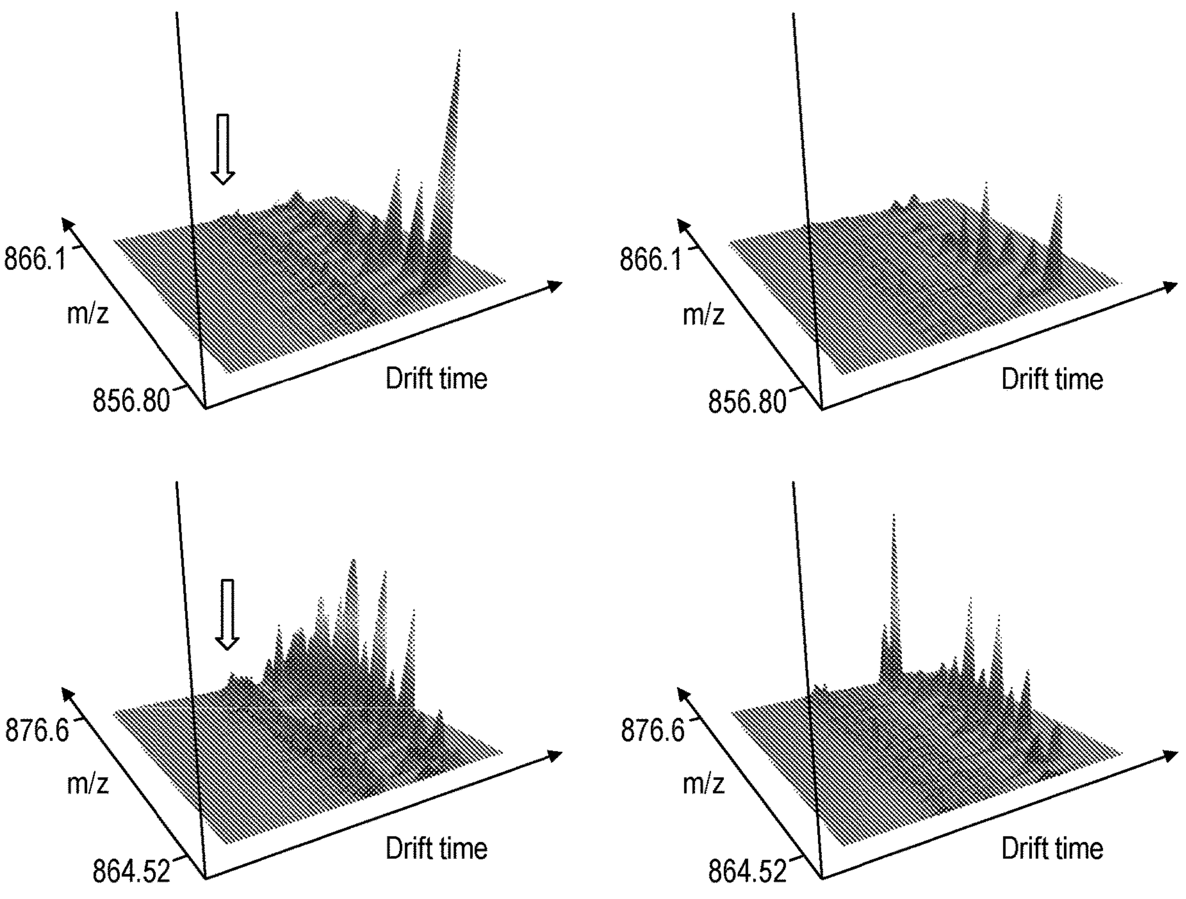
Figure 21:
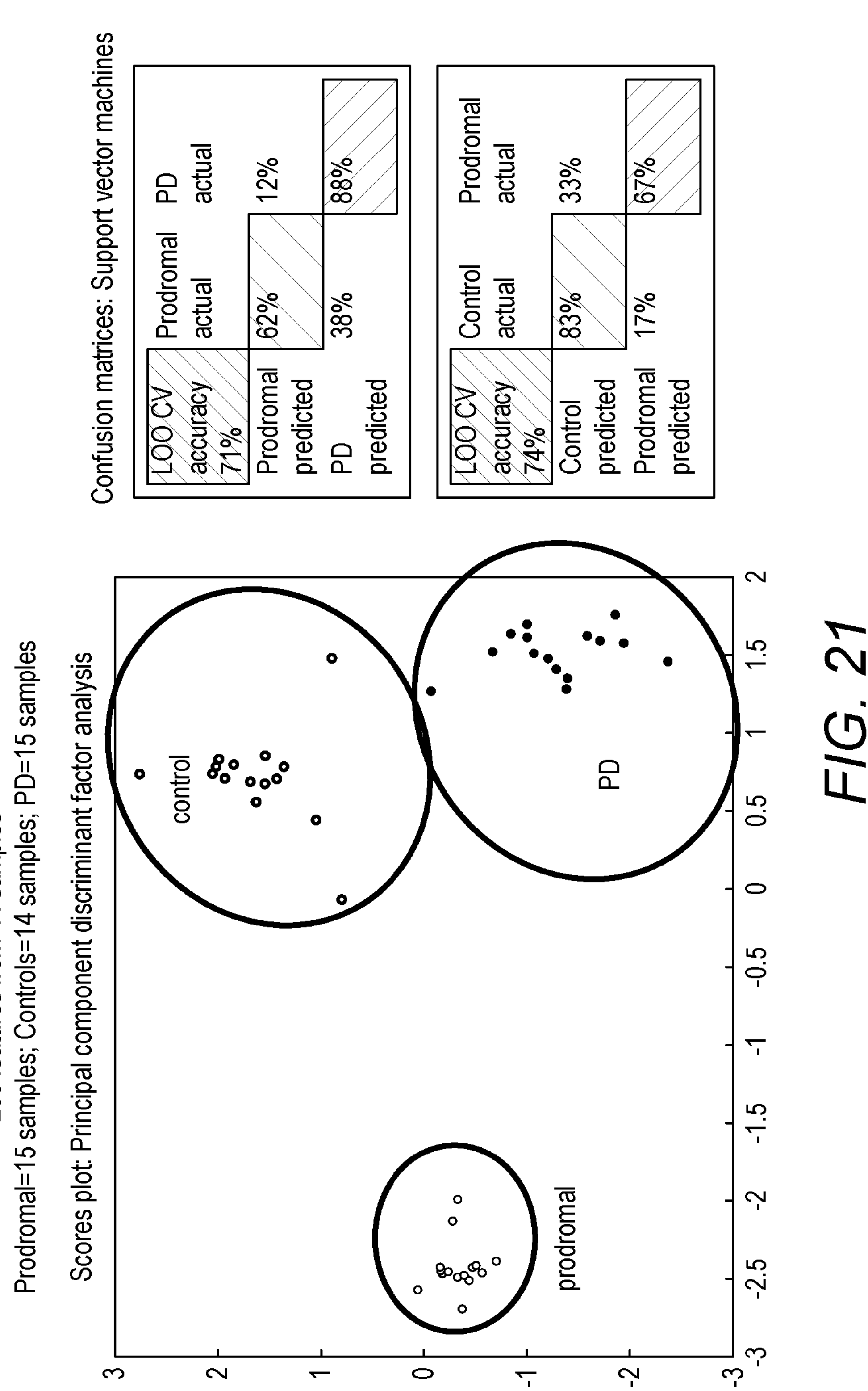
Figure 23:
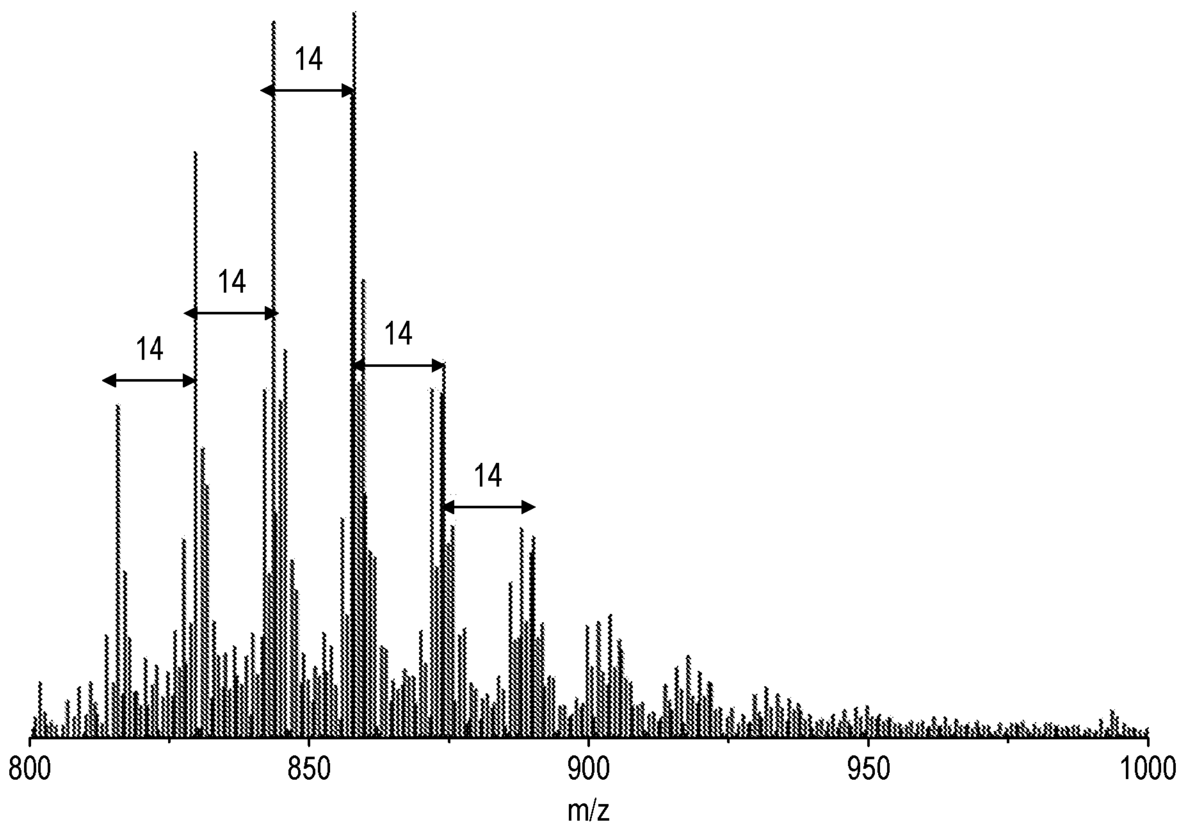
Figure 24:
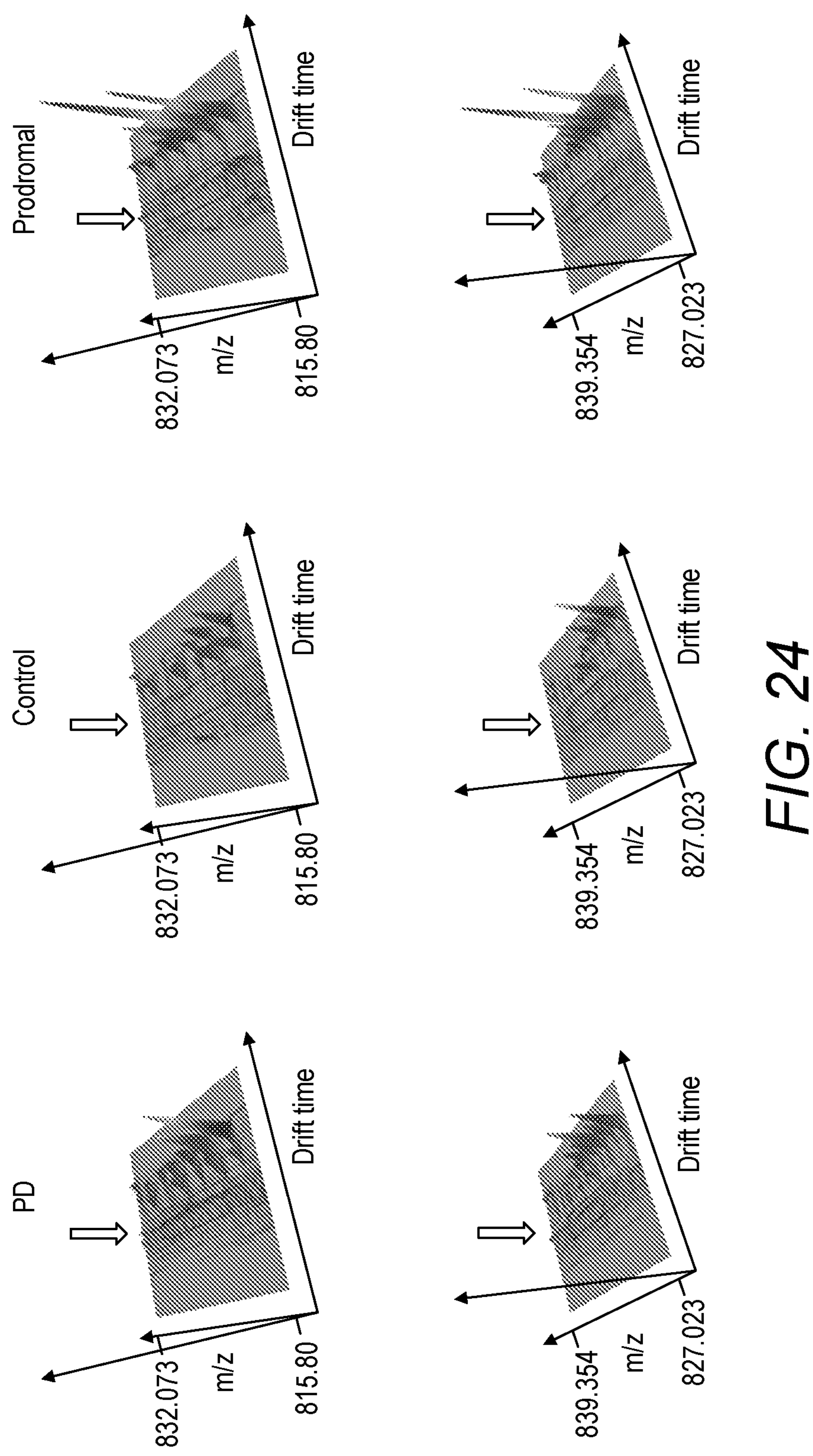
Figure 24:
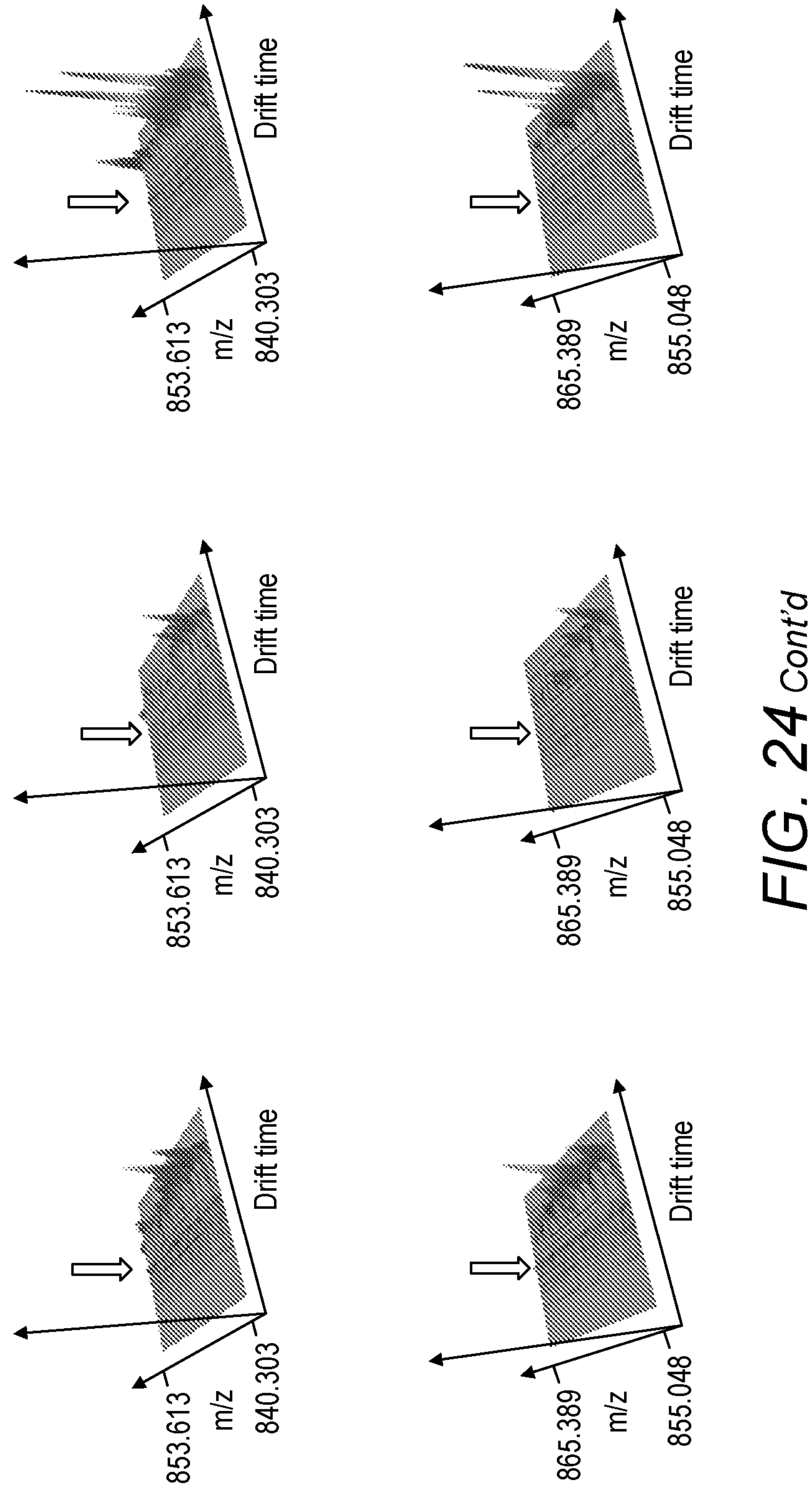
Figures 27A, 27B, 27C, 27D:
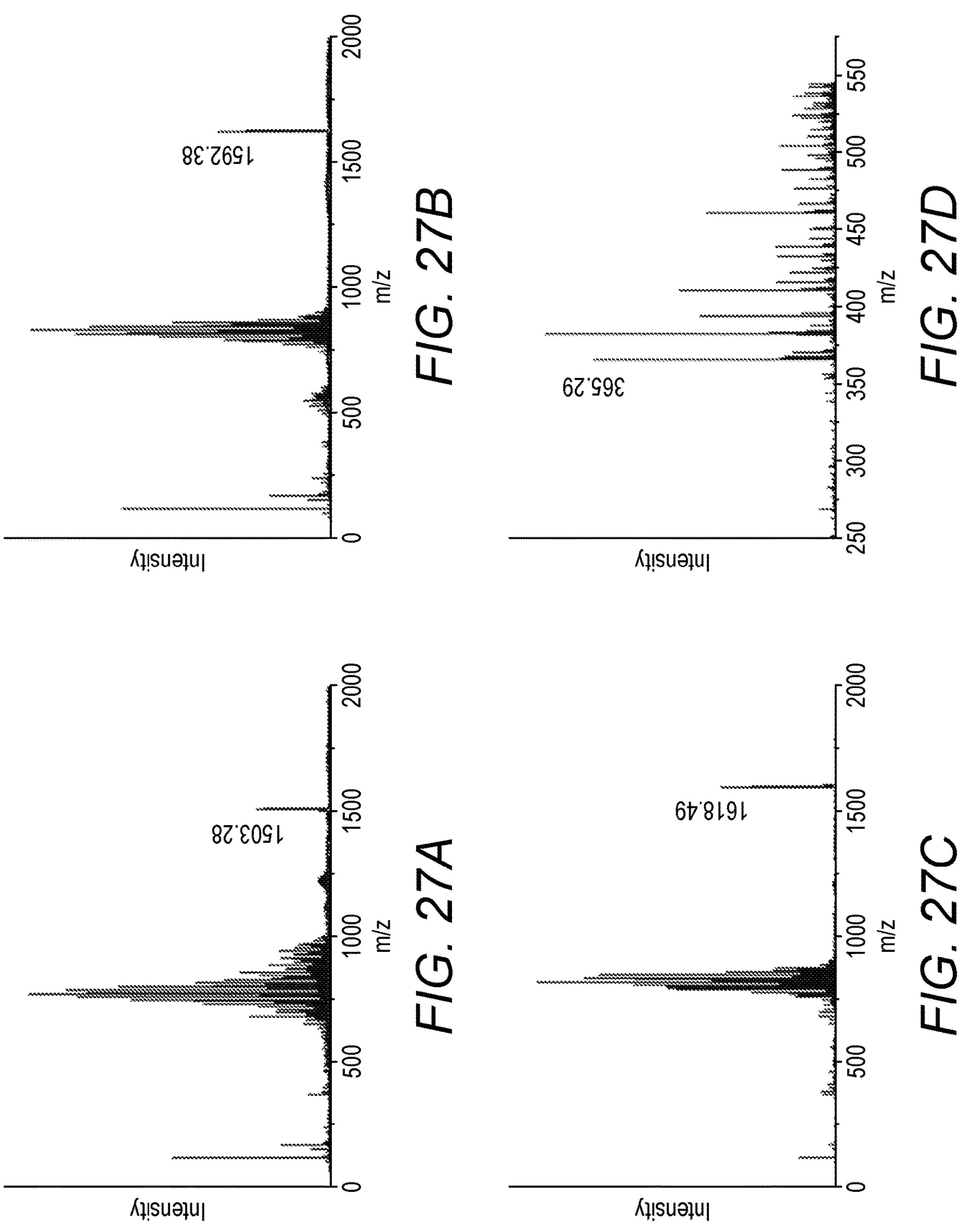
Figure 28A:
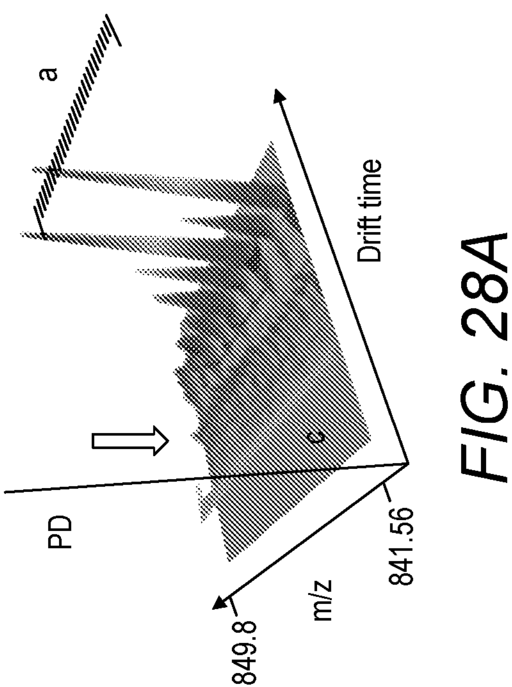
Figure 28B:
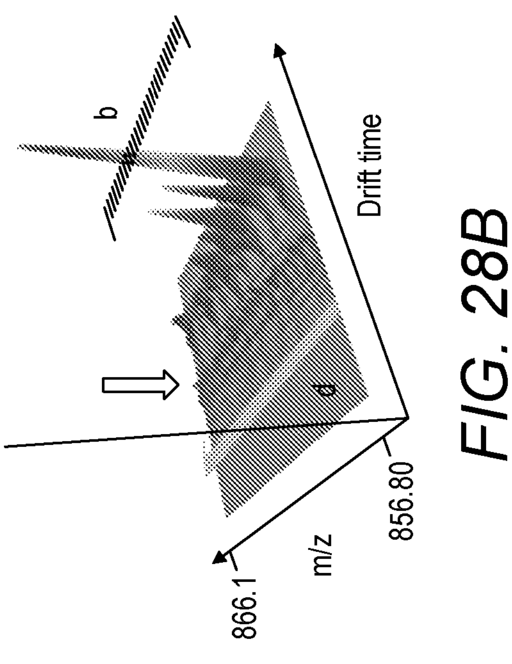
Figure 28C:
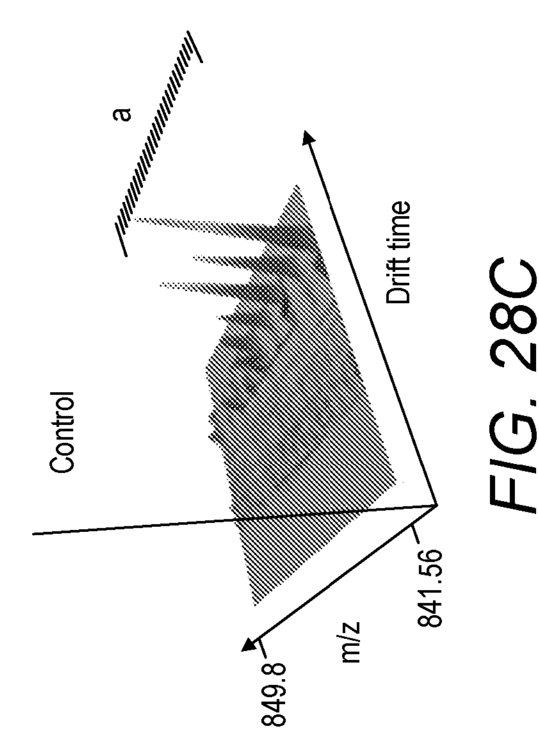
Figure 28D:
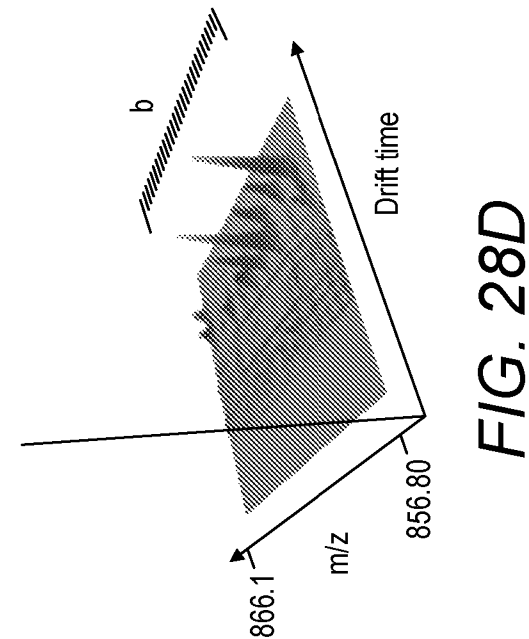
Figure 28E:
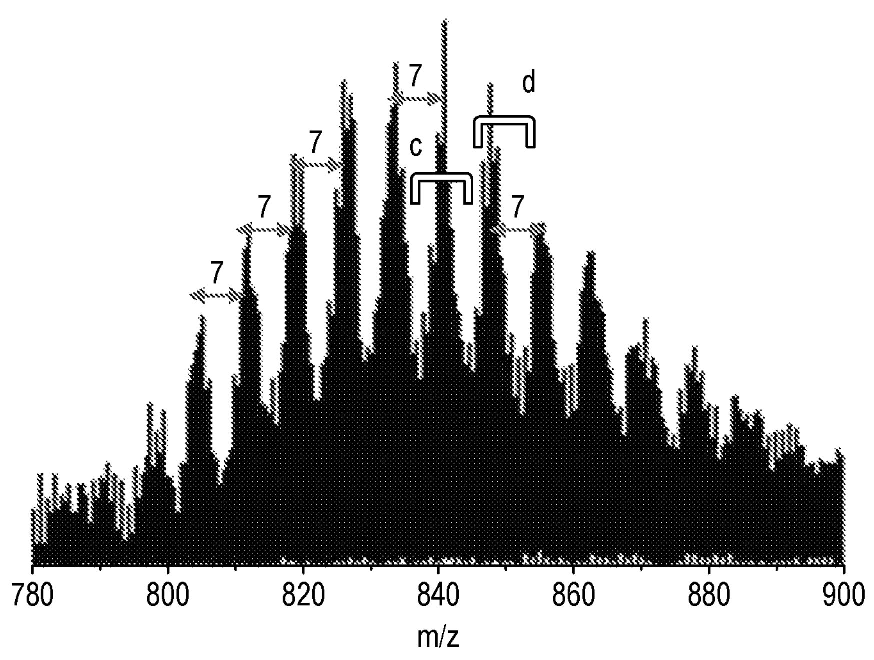
Figure 28F:
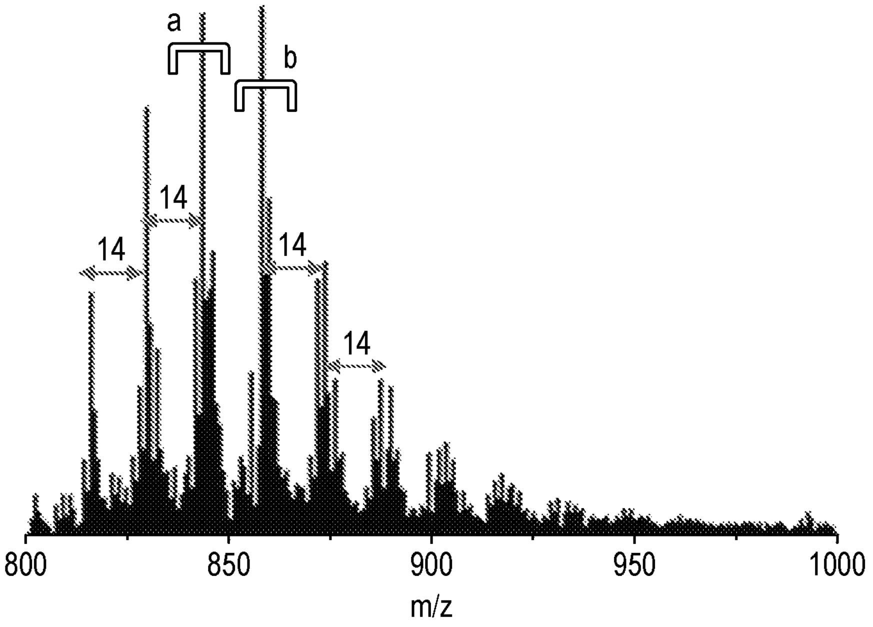

FIG. 15 shows photographs of vials demonstrating the results of the extraction protocol optimisation in Example 3. (A). Gauze extraction using Toluene paired to a Toluene: Methanol (20:80) reconstitution shows the formation of a solid residue—the addition of chloroform followed by centrifugation (x2 steps) allowed a clear supernatant to be obtained. (B.) Toluene gauze extraction followed by a Toluene:Methanol (50:50) reconstitution shows a solid substance has formed. (C.) Folch extraction (Methanol:Water:Chloroform) of the gauze swab and subsequent reconstitution of the separated chloroform layer shows a cloudy solution has formed which did not reconstitute back in Water:Methanol (80:20)—stages of chloroform addition followed by sonication and centrifugation improved reconstitution results however too much sample was lost in the process;

FIG. 16 shows a schematic representation of PSI-MS analysis of human sebum and a mass spectrum recorded from it;

FIG. 17 shows a comparison of PSI-MS data recorded from Whatman 42 and 1 (A) as a total ion chromatogram and (B) as an average mass spectrum;

FIG. 18 shows (A) a total ion chromatogram recorded from human sebum showing arrival time distribution of different diagnostic ions, (B) arrival time distribution of a single ion indicating the presence of isomeric structures and (C) a drift time vs m/z plot. The red dots represent equal m/z values. The zoomed image inset indicates the presence of a species with the same mass but with a different drift time;

FIG. 19 shows box plots for four m/z values that are statistically important with a p-value of $<0.1$;

FIG. 20 shows m/z vs drift time plots for the m/z values presented in Table 7 showing the separation of these ions on a drift time scale in PD samples. No separation was observed in the control samples;

FIG. 21: X-axis=DF1, Y-axis=DF2. Principal component discriminant factor analysis (PC-DFA) scores plot shows three distinct clusters based on m/z values detected using TD-GC-MS. Prodromal participants are a distinct cluster across DF1 whereas small differences appear between PD and control across DF2. Support Vector Machines were used to perform machine learning from these data and generate classification by leave one out approach. The model was tested on out of bag samples;

FIG. 22 shows mass spectra collected from sebum using A) touch and roll transfer and B) quick extraction in 100% EtOH, clearly indicating the presence of higher mass molecules (in between m/z 1200-2000) in case of touch and roll transfer;

FIG. 23 shows zoomed (m/z 800-1000) mass spectrum collected from sebum using paper spray ionization showing an envelope of peaks with 14 Da difference;

FIG. 24 shows three-dimensional DT vs. m/z plots for PD, control, and prodromal samples showing a significant difference in the molecular composition of sebum produced by people of each class. The red arrow indicates a particular drift time at which certain molecular species were observed in the case of PD and prodromal samples which were absent in the case of control participants;

FIG. 25: A) Extracted arrival time distribution for a selected ion (m/z 843.7074), B and C) corresponding average mass spectra from the drift time peaks at 10.43 and 6.67 ms. D) Zoomed mass spectra showing the doubly charged peaks correspond to a dimeric species;

FIG. 26 shows tandem mass spectrometry data for standard lipids A) L-α-phosphatidylcholine, B) L-α-phosphatidylserine (sodium salt), and C) 18:1 cardiolipin showing fragmentation of the head group as their fingerprint for identification. D-F) Show MSMS of selected m/z values (760.00, 839.75, 865.77, respectively) from sebum samples. All these selected ions fragment to m/z 202.23. G) Shows a MSMS spectrum for sebum in which the source parameters were set such as to get in-source fragmentation to create m/z 202.23 fragment from its parent ions followed by isolation of the daughter ion for further fragmentation. Inset of D shows a zoomed mass spectrum collected from sebum showing an accurate mass match with a phosphatidylcholine with the chemical formula $C_{42}O_8H_{83}PN$;

FIG. 27 shows $MS^2$ spectra for selected ions in the m/z 1500-1700 region; and FIG. 28 shows three-dimensional DT vs. m/z plots for PD (A and B) and control (C and D) samples showing a significant difference in the molecular composition of sebum produced by people with Parkinson's disease. The red arrow indicates a particular drift time at which certain molecular species were observed in the case of PD samples which were absent in the controls. E), and F) Mass spectra corresponding to the low and high drift time peaks, respectively. The peaks in the envelope are 14 Da (in F) and 7 Da (in E, being doubly charged). The labels a, b, c, and d represent respective series of peaks in the envelope.

FIG. 29: A) Collision cross section (CCS) vs m/z plot for a mixture of lipid standards in mass range 500-900 Da. Data points numbered 1-13 show CCS values for different classes of lipids. Triplicate measurements were acquired under identical conditions (Δ□◇ symbols represent each measurement). B) CCS vs m/z plot for sebum. The inset in B shows the mass spectrum of sebum in the m/z 700-950 region showing an envelope of singly charged peaks with 14 Da difference. C) MSMS spectrum of triolein (TG 18:1) which is one of the components in the standard lipid mixture. As can be noted the predominant fragments are m/z 603.55, 339.29, and 265.26. D) An MSMS spectrum of m/z 867.71 from sebum showing similar fragmentation compared with the TG 18:1 lipid standard (X.C). All data presented in this figure were collected using PSI IM MS using a travelling wave instrument (Waters Cyclic IMS).

Figure 30:
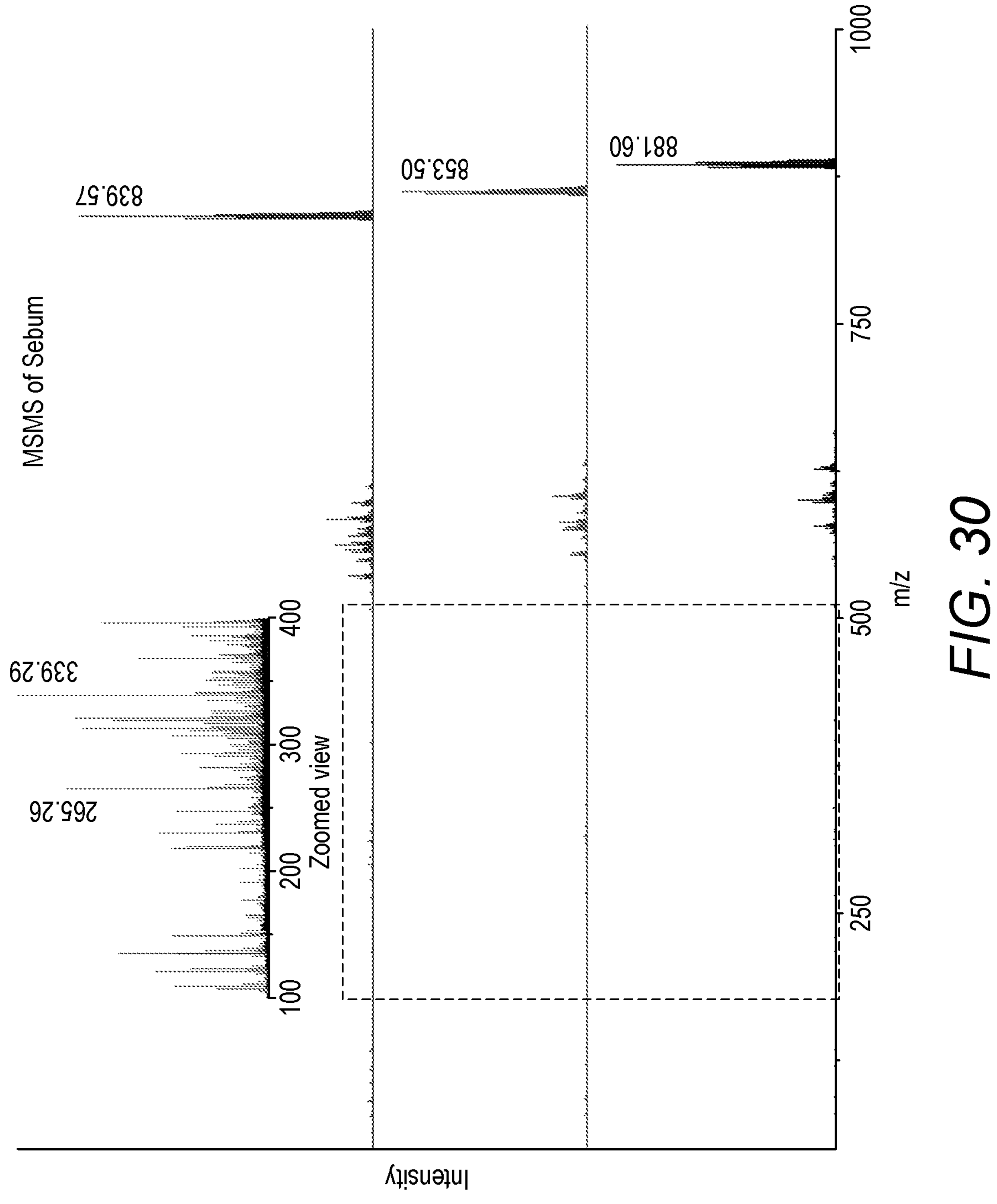

FIG. 30 shows MSMS spectra of different peaks (appearing at 14 Da apart on the lower mass range) present in sebum. The inset shows the zoomed view of the spectrum in the range of m/z 100-400. Fragment peaks at m/z 339.29, and 265.26. Da is common in all of these spectra. This indicates that two of the fatty acid chains in the TG class of lipid are common and the chain length varies on the third fatty acid.

Figure 31:
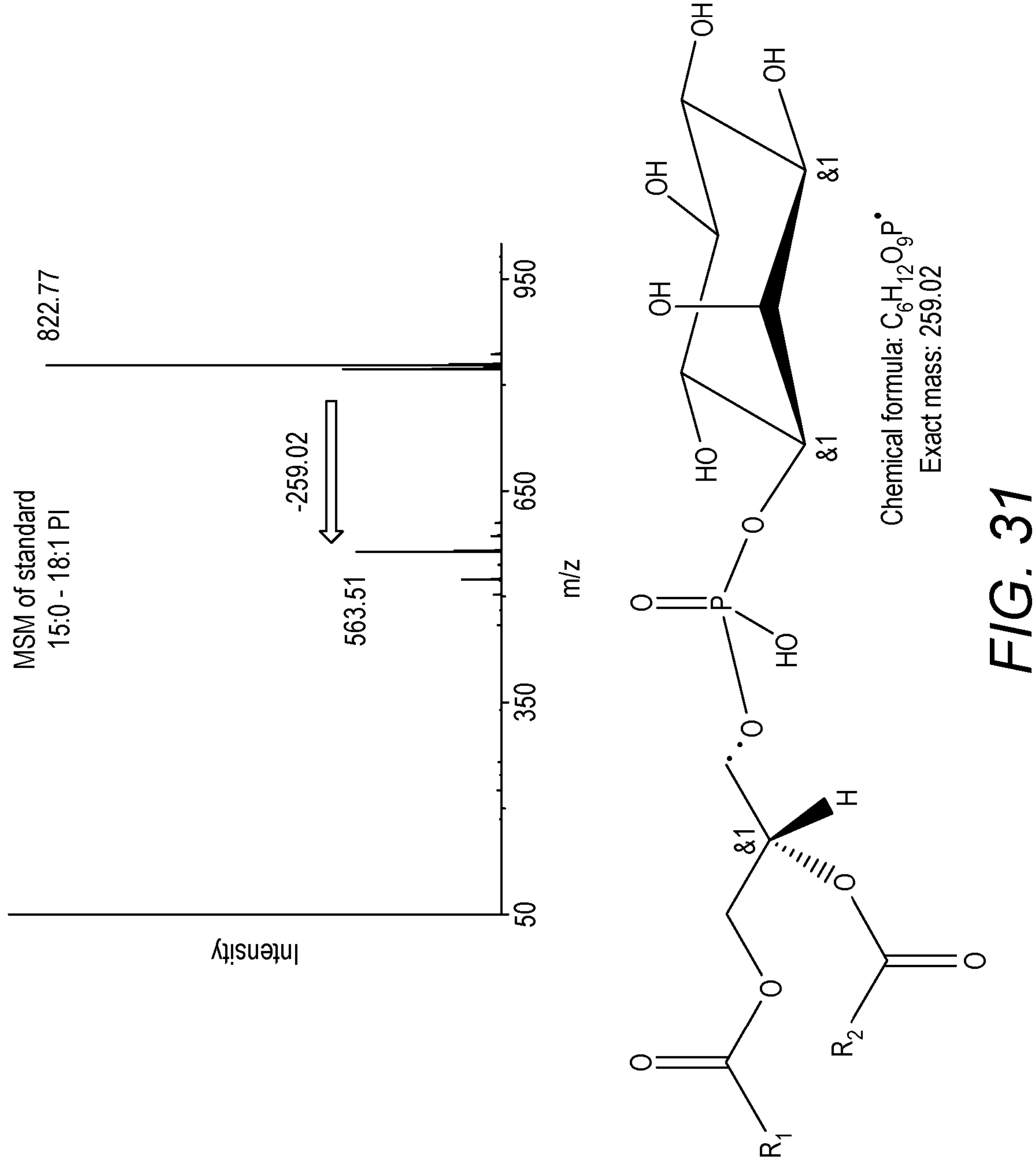

FIG. 31 shows MSMS of 15:0-18:1 PI showing a characteristic loss of 259 Da of the polar head group of the PI lipid class.

EXAMPLE 1—EXPERIMENTS TO ASSESS SEBUM FOR THE PRESENCE OF VOLATILE BIOMARKERS FOR PARKINSON'S DISEASE

Study Participants

The participants for the study were part of a nationwide recruitment process taking place at 25 different NHS clinics. The participants were selected at random from these sites. The study was performed in three stages. The first two stages (discovery and validation) consisted of 30 samples (a mixture of control, PD participants on medication and drug naïve PD subjects as shown in Table 1 below).

TABLE 1

Details of the collecting sites in the UK.

| | SITE |
|---|---|
| 1 | Addenbrooks (Cambridge) |
| 2 | Bournemouth |
| 3 | Cornwall/Truro |
| 4 | Lothian-Western General Edinburgh |
| 5 | Edinburgh-MRC/Regenerative Med (Royal Infirmary of Edinburgh) |
| 6 | Edinburgh-Primary Care NHS Lothian (Seb Derm) |
| 7 | Hampshire |
| 8 | Nottingham |
| 9 | Pennine |
| 10 | Salford |
| 11 | Salisbury |
| 12 | Sheffield |
| 13 | South Tees |
| 14 | Southern Health |
| 15 | Luton & Dunstable |
| 16 | Portsmouth |
| 17 | Northumbria |
| 18 | London North West |
| 19 | Bath |
| 20 | Gateshead |
| 21 | Sunderland |
| 22 | Plymouth |
| 23 | Newcastle Upon Tyne Hospitals NHS Foundation Trust (Newcastle University) |
| 24 | Royal Devon and Exeter NHS Foundation Trust |
| 25 | Imperial College Healthcare NHS Trust |

The first cohort was used for volatilome discovery, and the second cohort was used to validate the significant features discovered in first cohort. A third cohort consisting of three drug naïve PD participants was used for smell analysis from the Super Smeller. The metadata analysis for these participants is shown in Table 2 below.

TABLE 2

Participant numbers and metadata per wave. (* indicates significant difference between controls, drug naive and PD with medication groups)

| Wave 1 (untargeted profiling) | | | | |
|---|---|---|---|---|
| | Control (n = 10) | Drug Naïve PD (n = 10) | PD on medication (n = 10) | p-value |
| Age (years) | 64.8 ± 3.06 | 72.82 ± 8.42 | 64.67 ± 2.55 | 0.01* |
| BMI | 27.10 ± 3.50 | 26.94 ± 4.08 | 25.33 ± 3.44 | 0.64 |
| Gender (M/F ratio) | 0.84 | 1.20 | 0.80 | 0.88 |
| Alcohol intake (yes/no ratio) | 4.5 | 0.37 | 2 | 0.03* |
| Smoker | 1 | 0 | 0 | 0.39 |
| **Wave 2 (targeted discovery)** | | | | |
| | Control (n = 11) | Drug Naïve PD (n = 11) | PD on medication (n = 9) | p-value |
| Age (years) | 55.78 ± 18.87 | 75.40 ± 6.85 | 68.90 ± 11.76 | 0.02* |
| BMI | 28.96 ± 11.01 | 25.74 ± 3.83 | 24.98 ± 3.54 | 1.00 |

TABLE 2-continued

| Participant numbers and metadata per wave. (* indicates significant difference between controls, drug naive and PD with medication groups) | | | | |
|---|---|---|---|---|
| Gender (M/F ratio) | 0.26 | 1.50 | 1 | 0.10 |
| Alcohol intake (yes/no ratio) | 0.8 | 9 | 1.5 | 0.10 |
| Smoker | 0 | 0 | 1 | 0.24 |
| Wave 3 (odour port validation, drug naive PD subjects only, n = 3) | | | | |
| Age (years) | 65.66 ± 3.30 | | | |
| BMI | 23.46 ± 1.80 | | | |
| Gender (M/F ratio) | 2 | | | |
| Alcohol intake (yes/no ratio) | 2 | | | |
| Smoker | 0 | | | |

Figure 4A:
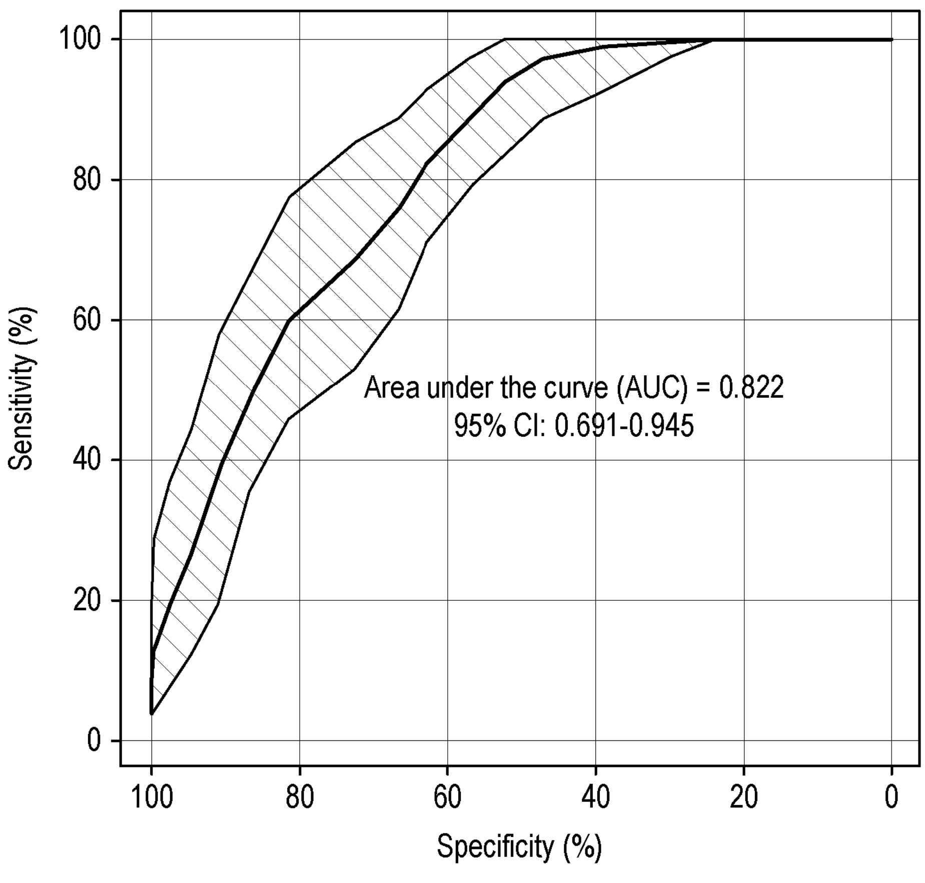
Figure 4B:
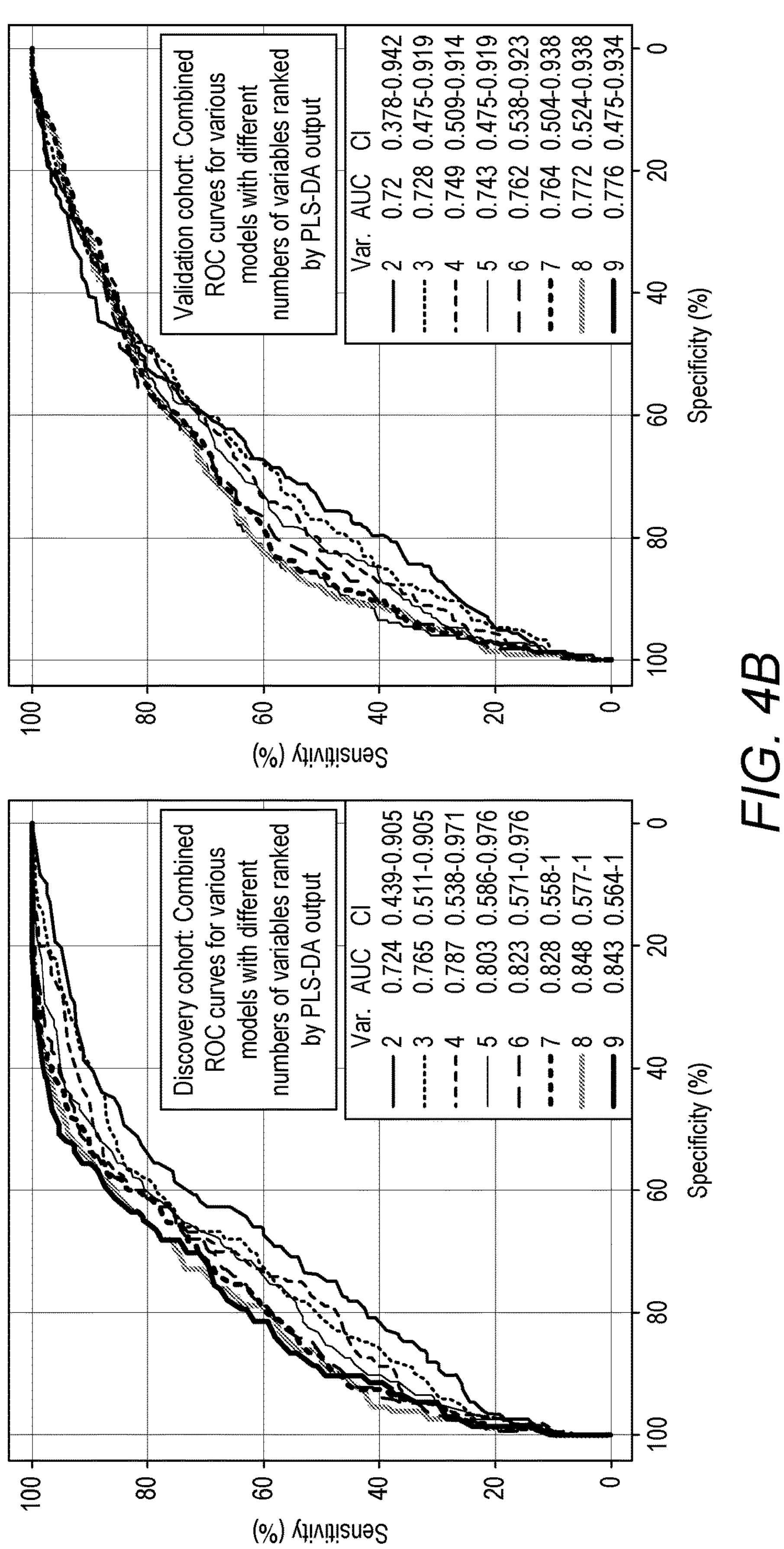
Figure 5:
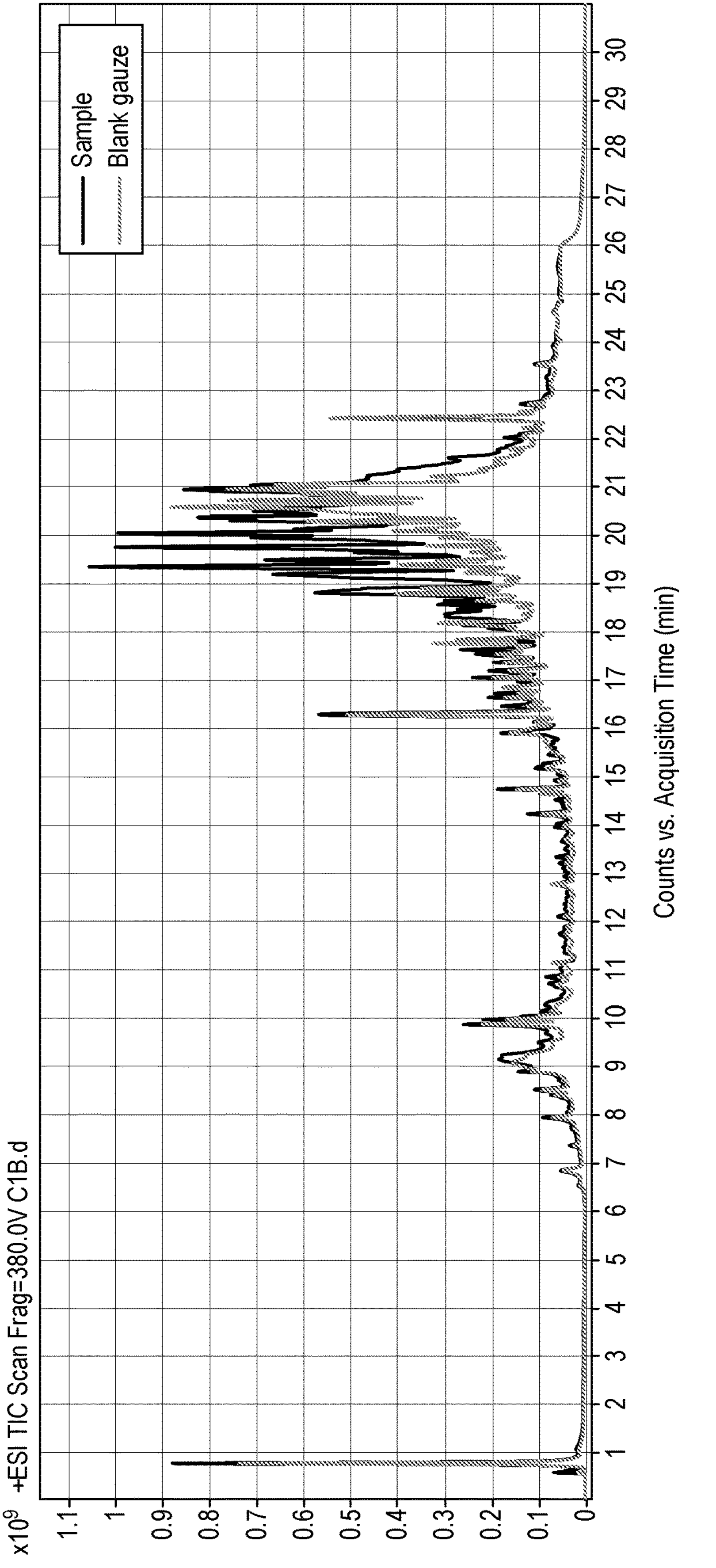
FIG. 5 shows a plot of blank gauze vs sample reconstituted in $H_2O$:ACN (50:50)
Figure 6:
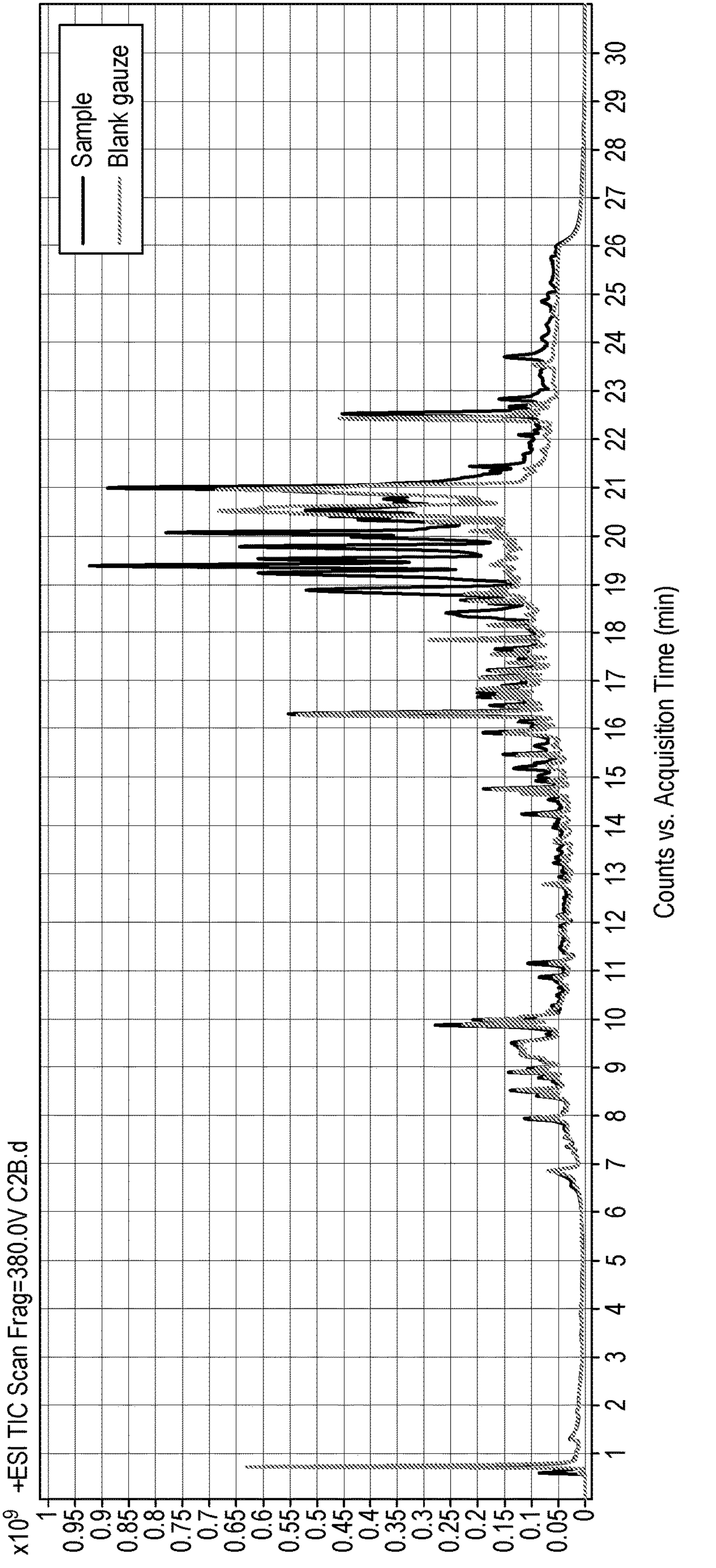
FIG. 6 shows a plot of blank gauze vs sample reconstituted in $H_2O$:MeOH (50:50)
Figure 7:
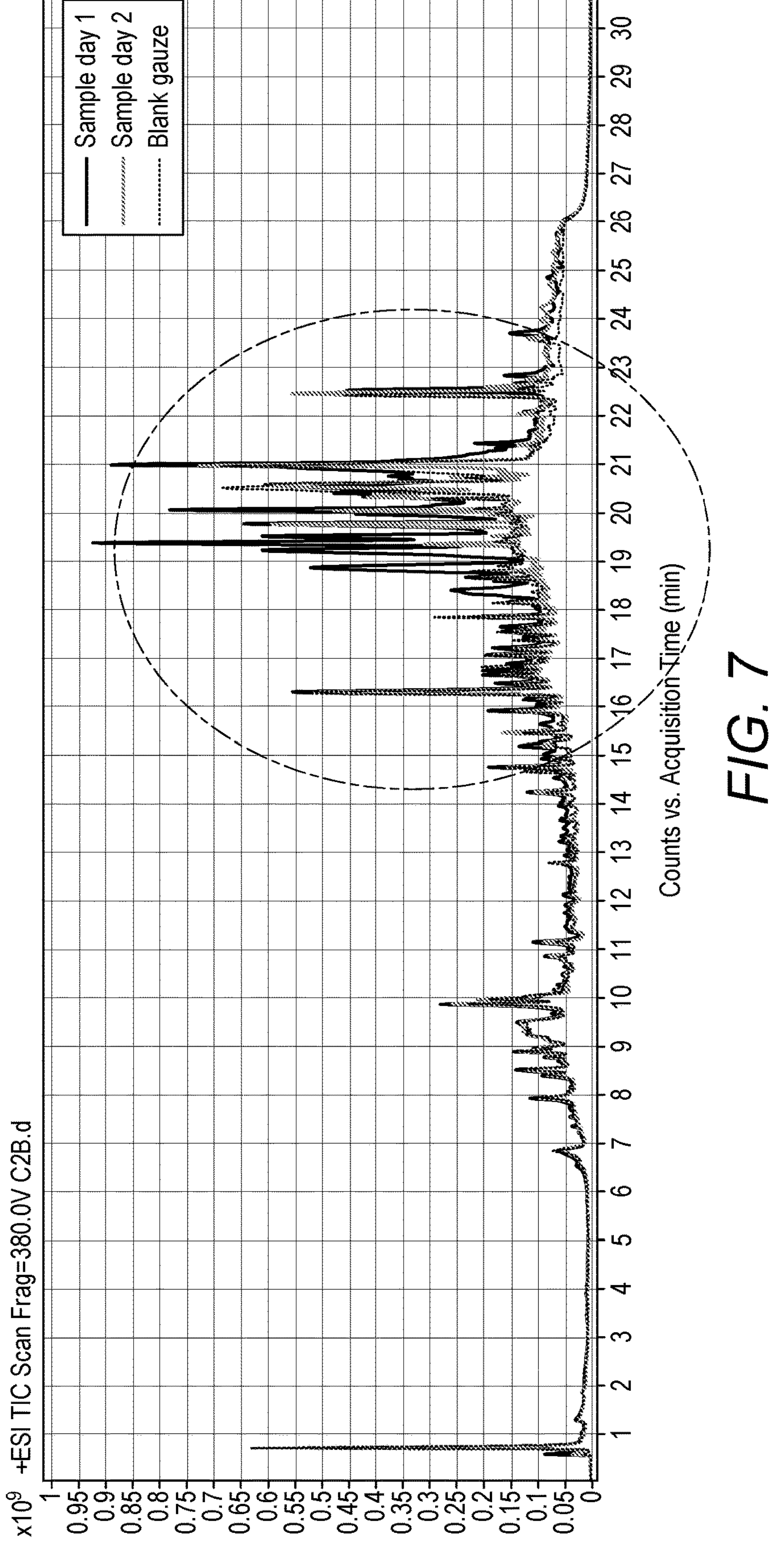
FIG. 7 shows a plot of blank gauze vs day 1 sample vs day 2 sample (same subject) reconstituted in $H_2O$:MeOH (50:50)
Figure 8:
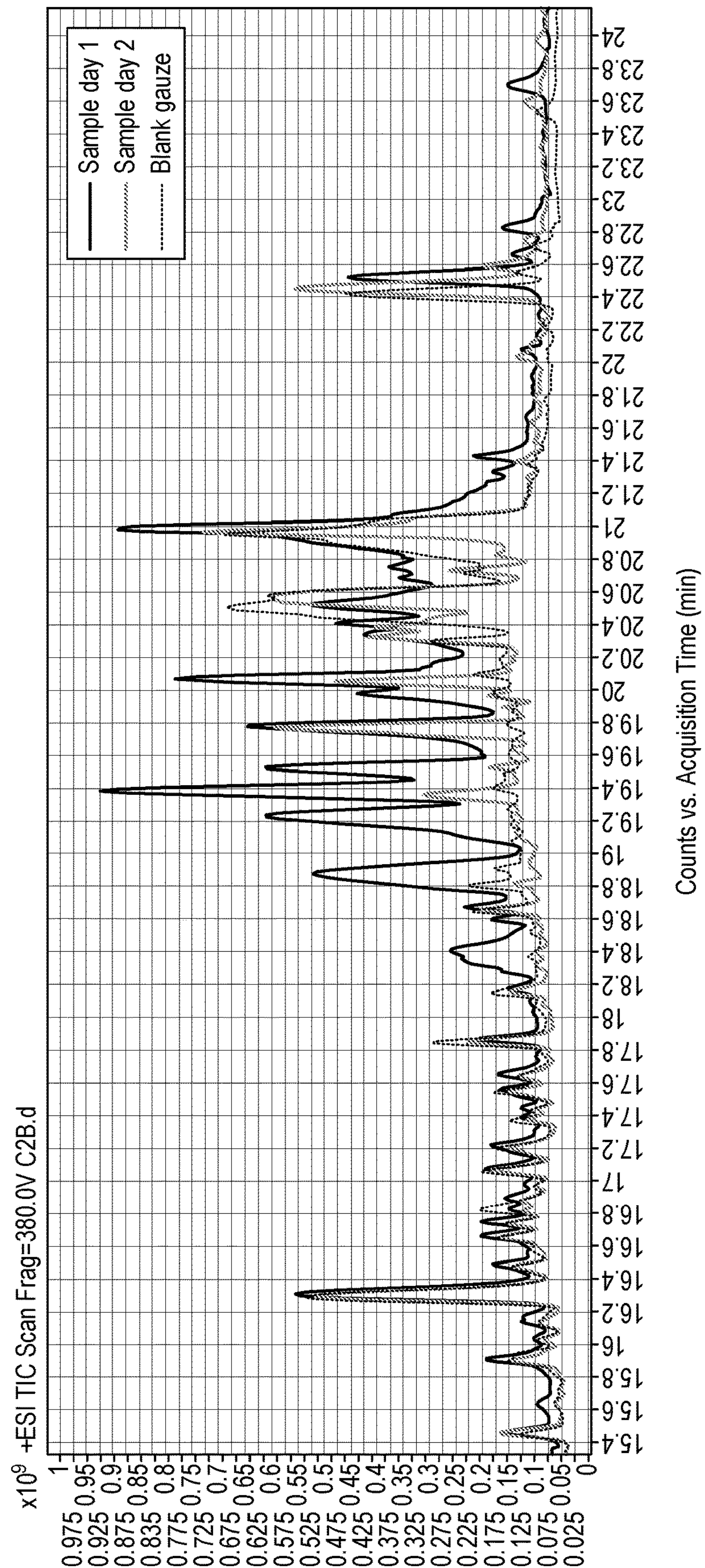
FIG. 8 shows a zoomed in region of the plot of FIG. 7 (15 min-24 min)
Figure 9:
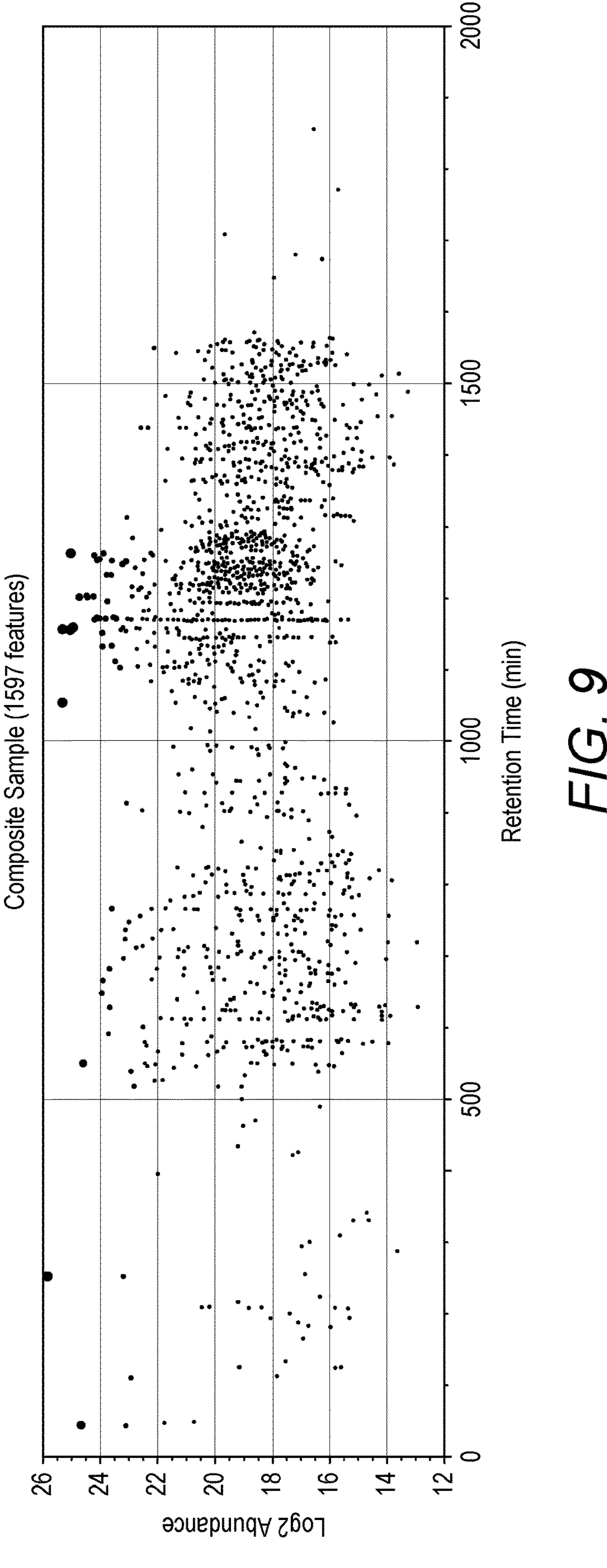
FIG. 9 shows a plot of XCMS based deconvolution.
Figure 10:
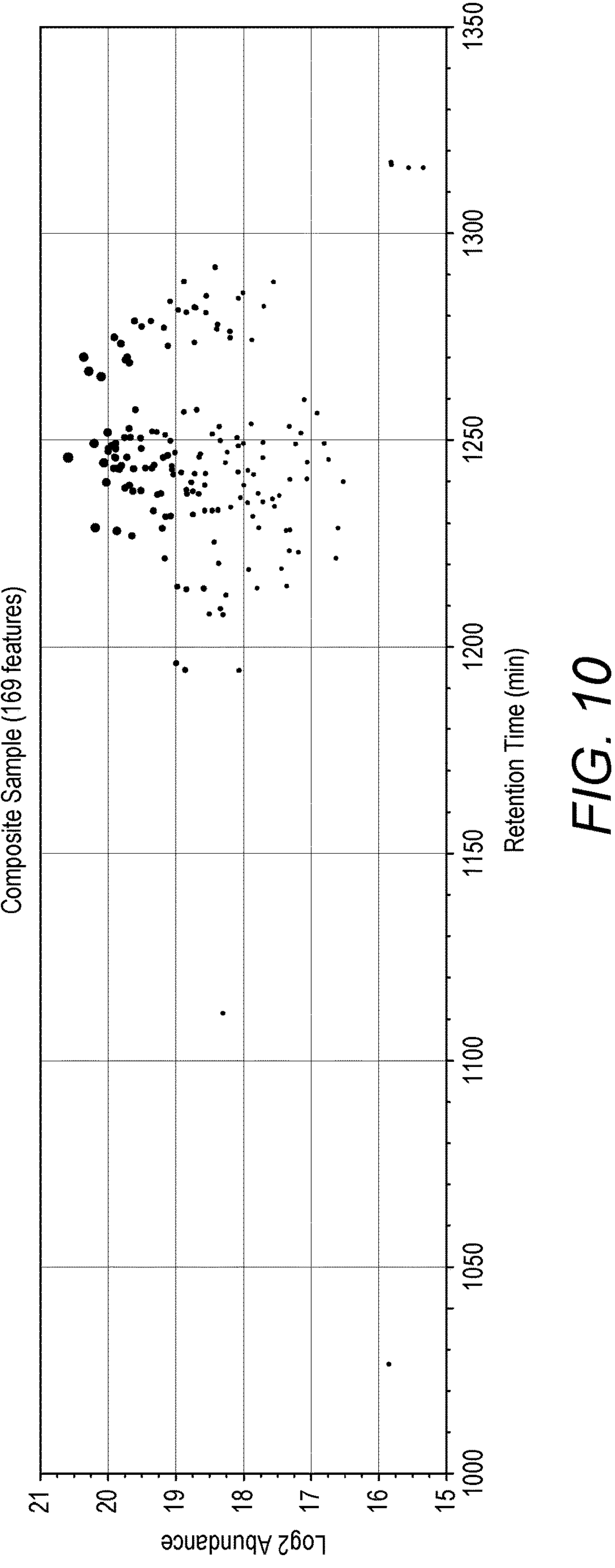
FIG. 10 shows a plot of features unique to samples only.
Figure 11:
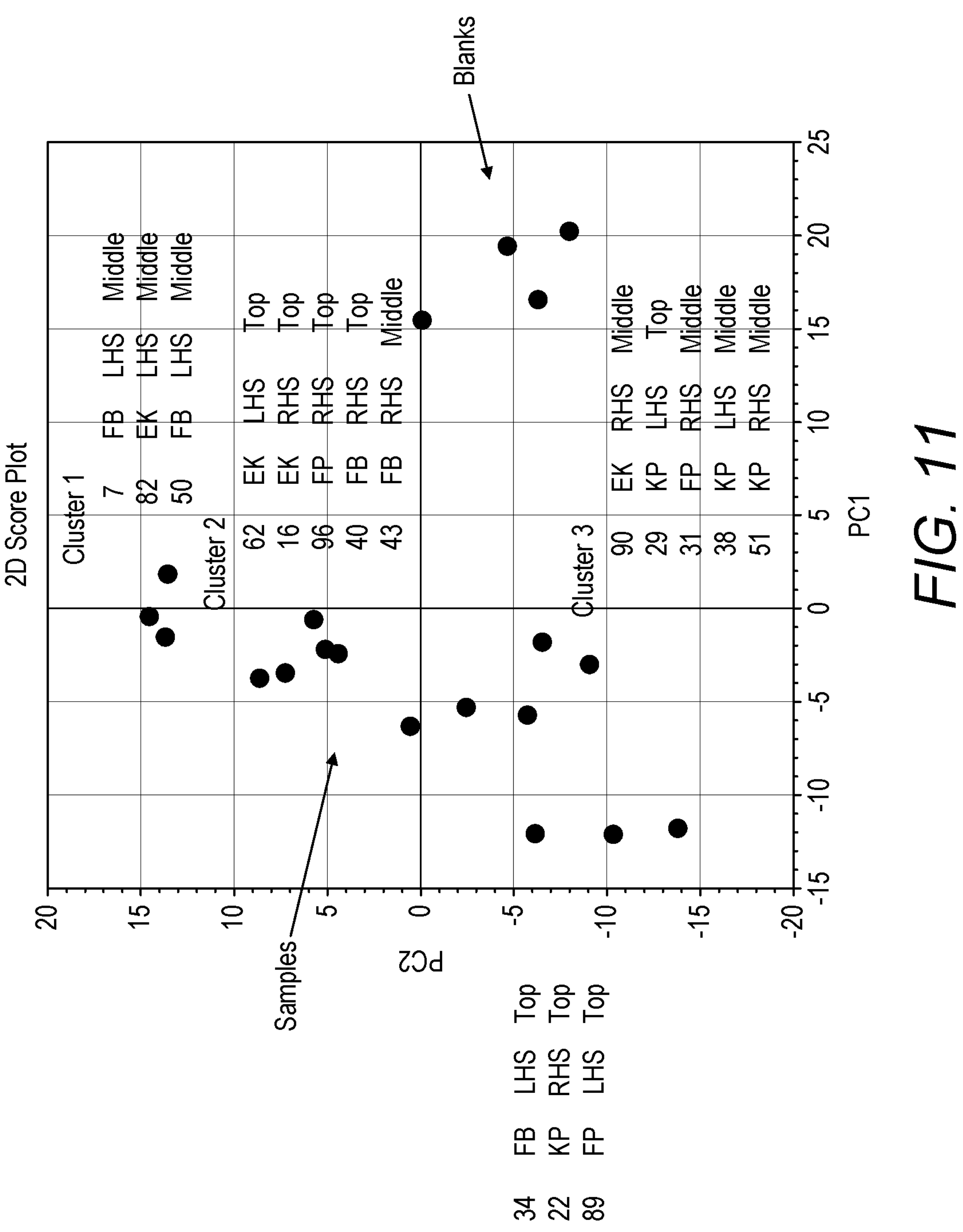
FIG. 11 shows a plot of methanol 9 mL data.
Figure 12:
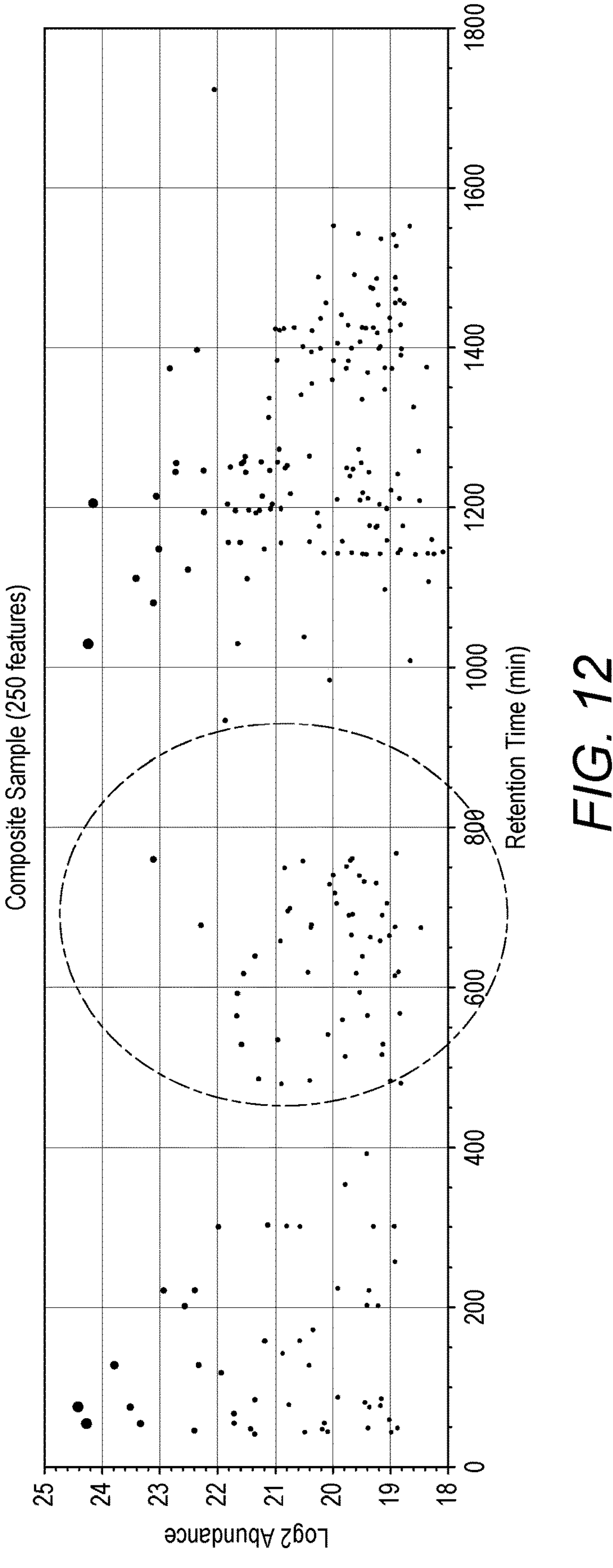
FIG. 12 shows a plot of potential PEG area.

The study design is also outlined in FIG. 4.

Sample Collection

The sampling involved each subject being swabbed on the upper back with a medical gauze. The gauze with sebum sample from participant's upper back was sealed in background-inert plastic bags and transported to the central facility, where they were stored at −80° C. until the date of analysis.

TD-GC-MS Analysis

Description of the Technique

A Dynamic Headspace (DHS) GC-MS method was developed for the analysis of gauzes used to swipe skin of PD affected individuals. DHS is a sample preparation capability for subsequent GC application using the GERSTEL Multi-Purpose Sampler (MPS). DHS extracts and concentrates VOCs from liquid or solid samples. The sample is incubated while the headspace is purged with a controlled flow of inert gas through an adsorbent tube. Once extraction and pre-concentration is completed, the adsorbent tube is automatically desorbed using the GERSTEL Thermal Desorption Unit (TDU). Analytes are then cryo-focused on the GERSTEL Cool Injection System (CIS) PTV injector before being transferred to the GC for analysis.

In order to correlate the PD molecular signature to the PD smell, the same setup was used in combination with the GERSTEL Olfactory Detection Port (ODP). The ODP allows detection of odorous compounds as they elute from the GC by smell. In fact, the gas flow is split as it leaves the column between the detector of choice (in our case MS) and the ODP to allow simultaneous detection on the two analytical tools. The additional smell profile information can then be acquired. Voice recognition software and intensity registration allow direct annotation of the chromatogram.

Method Details

Gauzes were transferred into 20 mL headspace vials and then analysed by DHS-TDU-GC-MS. For the DHS pre-concentration step, samples were incubated for 5 min at 60° C. before proceeding with the trapping step. Trapping was performed purging 500 mL of the sample headspace at 50 $mL \cdot min^{-1}$ through a Tenax® TA adsorbent tube kept at 40° C. (GERSTEL, Germany). Nitrogen was used as purge gas. To release the analytes, the adsorbent trap was desorbed in the TDU in splitless mode. The TDU was kept at 30° C. for 1 min then ramped at 720° $C. \cdot min^{-1}$ to 250° C. held for 5 min. Desorbed analytes were cryofocused in the CIS injector. The CIS was operated in solvent vent mode, using a vent flow of 80 $mL \cdot min^{-1}$ and applying a split ratio of 10. The initial temperature was kept at 10° C. for 2 min, then ramped at 12° $C. \cdot s^{-1}$ to 250° C. held for 10 min. The GC analysis was performed on an Agilent GC 7890B coupled to an Agilent MSD 5977B equipped with high efficiency source (HES) operating in EI mode. Separation was done an Agilent HP-5MS Ultra inert 30 m×0.25 mm×0.25 μm column. The column flow was kept at 1 $mL \cdot min^{-1}$. The oven ramp was programmed as following: 40° C. held for 5 min, 10° $C. \cdot min^{-1}$ to 170° C., 8° $C. \cdot min^{-1}$ to 250° C., 10° $C. \cdot min^{-1}$ to 260° C. held for 2 min for a total run time of 31 min. The transfer line to the MS was kept at 300° C. The HES source was kept at 230° C. and the Quadrupole at 150° C. The MSD was operated in scan mode for mass range between 30 and 800 m/z. For the olfactometry approach, the chromatographic flow was split between the mass spectrometer and the GERSTEL Olfactory Detection Port (ODP3) using Agilent Technologies Capillary Flow Technology (three-way splitter plate equipped with make-up gas). The ODP3 transfer line was kept at 100° C. and humidity of the nose cone was maintained constant.

Data Pre-Processing and Deconvolution

TD-GC-MS data were converted to open source mzXML format using ProteoWizard. Each cohort data was deconvolved separately using in-house XCMS script written in R. The deconvolved analytes were assigned putative identifications by matching fragment spectra with compound spectra present in Golm database, NIST library and Fiehn GCMS library. The resulting matrices for each cohort consisted of variables and their respective area under the peak for each sample. All data were normalised for age and total ion count to account for confounding variables (see Table 2). The data was log-scaled and Pareto scaled prior to Wilcoxon-Mann-Whitney analysis, PLS-DA and the production of ROC curves as described.

Results

In the current study, VOCs from the sample headspace were measured in two cohorts:—a 'discovery' cohort and a 'validation' cohort, as suggested for biomarker discovery using metabolomics [21], each consisting of 30 subjects (for demographics see Table 2). A third cohort consisting of three drug naïve PD participants was used for mass spectrometry analysis in conjunction with a human Super Smeller via an odor port. This proof of principal study provides the first description of the skin volatilome in Parkinson's disease.

Figures 1A, 1B:
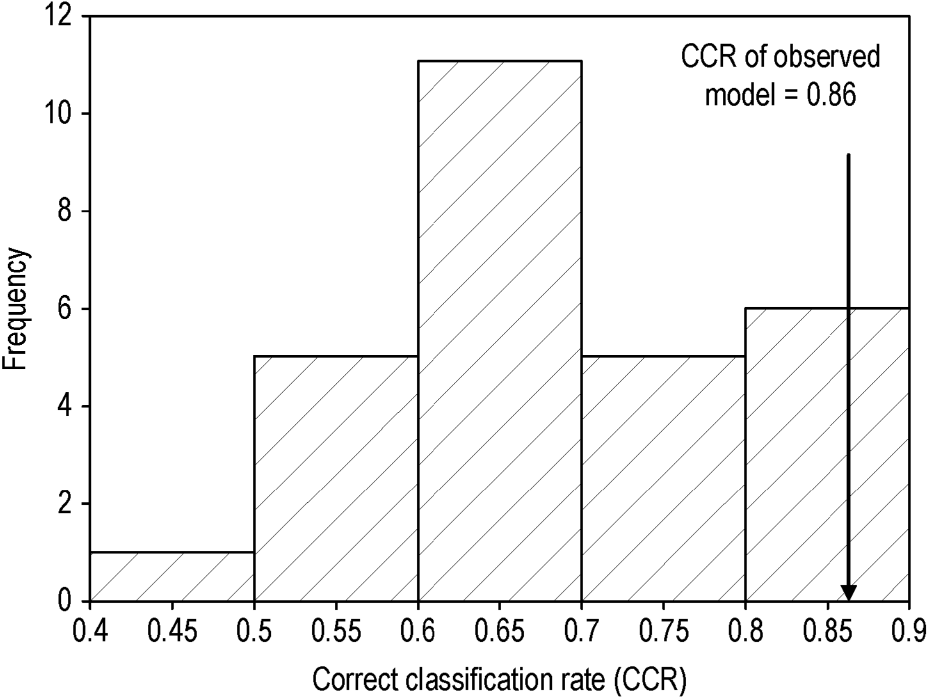

The mass spectrometry data were collected, deconvolved and pre-processed as described. Partial least squares discriminant analysis (PLS-DA) models were built using the discovery cohort data (FIG. 1). This modeling was validated with 5-fold cross validation (averaged correct classification rate (CCR) of 86%) as well as 26 permutation tests (averaged permutated CCR of 68%, averaged CCR of 83%, p-value<0.1). The variables contributing to classification (n=17) were selected using variable importance in projections (VIP) scores where VIP>1. The measured volatilome in the validation cohort data (from a different population than the discovery phase) was targeted for the presence or absence of these discovered biomarkers. Nine out of 17 metabolites were also found in the validation cohort data (Table 3 below).

TABLE 3

List of candidate volatiles putatively identified (MSI level 2) and matched across two different cohorts. Nine of out 17 metabolites were selected for further analysis since they had acceptable retention time drift between the two sets of experiments.

Figure 2B:
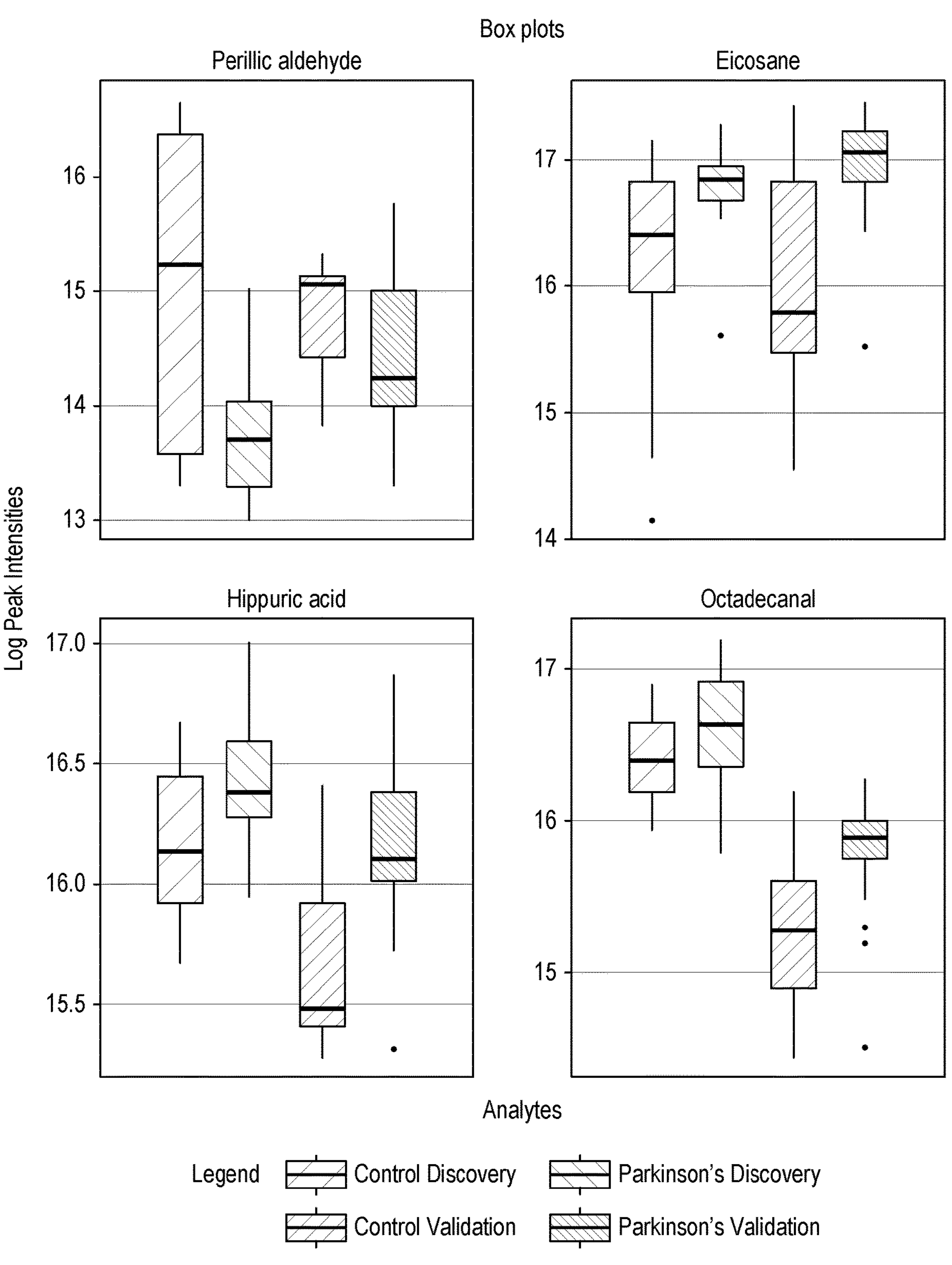

| Putative identification | Mass | Retention time (discovery) | Retention time (validation) | Retention time difference | Comments |
|---|---|---|---|---|---|
| dodecane | 170.34 | 13.20 | 13.27 | 0 | Included |
| eicosane | 282.56 | 20.65 | 20.62 | 0 | Included |
| octacosane | 394.77 | 17.49 | 17.46 | 0 | Included |
| hippuric acid | 179.17 | 20.61 | 20.52 | 0 | Included |
| octadecanal or dodecane | 170.34 | 20.87 | 20.75 | 0 | Included |
| artemisinic acid | 234.34 | 12.97 | 12.83 | 0 | Included |
| perillic aldehyde or diglycerol | 150.22 | 11.82 | 11.66 | 0 | Included |
| hexyl acetate or dodecane | 170.34 | 11.70 | 11.53 | 0 | Included |
| 3-hydroxytetradecanoic acid or octanal | 244.38 | 11.58 | 11.32 | 0 | Included |
| gallic acid ethyl ester | 198.17 | 11.40 | 10.99 | 0 | Excluded |
| cyclohexasiloxane, dodecamethyl | 357.57 | 16.47 | 16.06 | 0 | Excluded |
| proline | 115.13 | 14.27 | 13.77 | 1 | Excluded |
| glutamine[—$H_2O$] | 128.09 | 21.73 | 21.09 | 1 | Excluded |
| cyclohexylcyclohexane | 357.57 | 15.36 | 14.71 | 1 | Excluded |
| tetracosane | 338.65 | 18.17 | Not found | n/a | Not found |
| 3,4-dihydroxy mandelic acid | 184.15 | 20.87 | Not found | n/a | Not found |
| neoabietic acid | 302.46 | 21.66 | Not found | n/a | Not found |

at MSI level two [22]. Perillic aldehyde and eicosane were significantly different between PD and control in both the cohorts (p-value<0.05): perillic aldehyde was observed to be lower in PD samples whereas eicosane was observed at significantly higher levels. Although hippuric acid and octadecanal were not significantly different (p>0.05), the AUC (FIG. 2*a*) and box plots (FIG. 2*b*) between the two cohorts were comparable, showing similar trends.

Figure 2C:
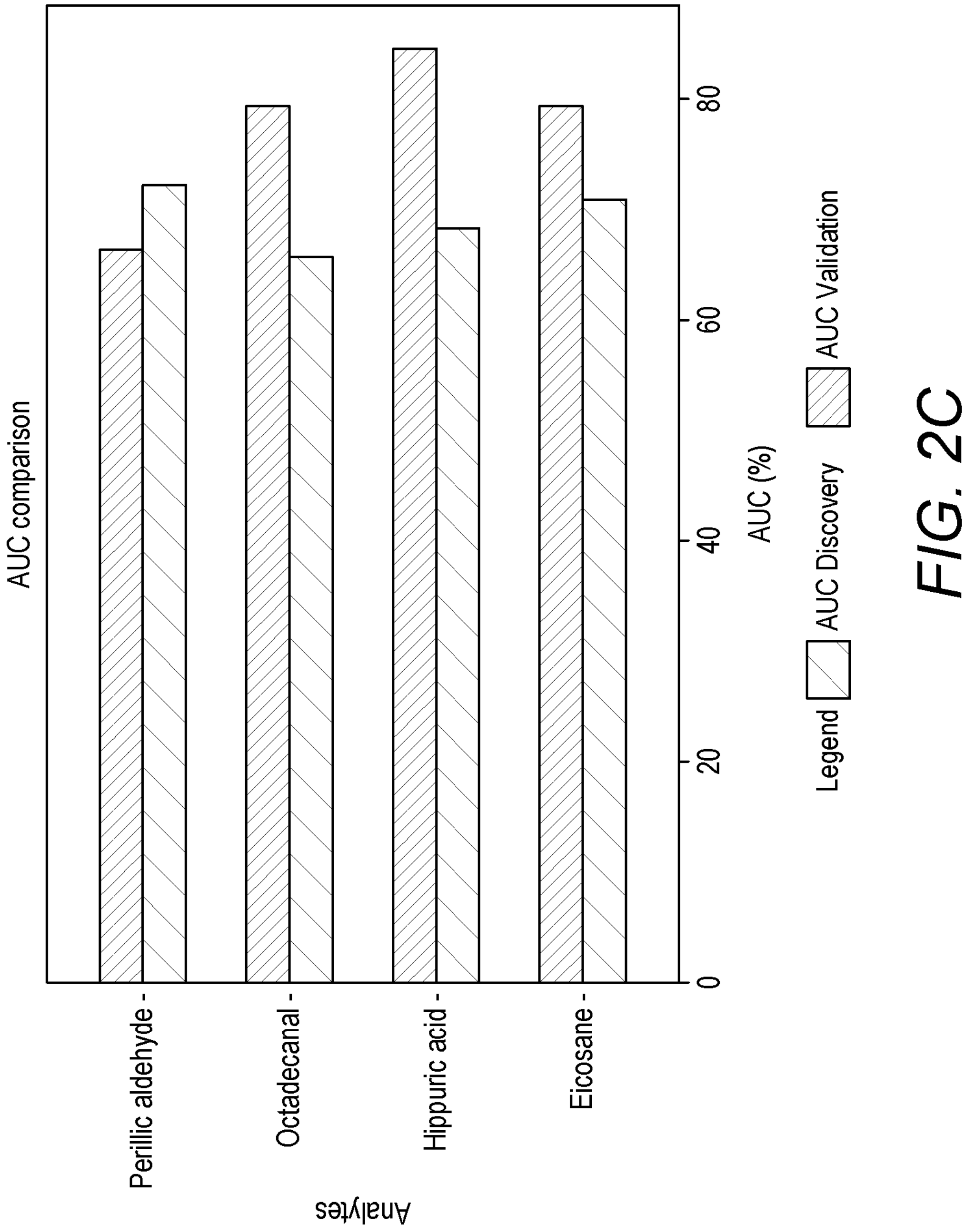
Figure 3:
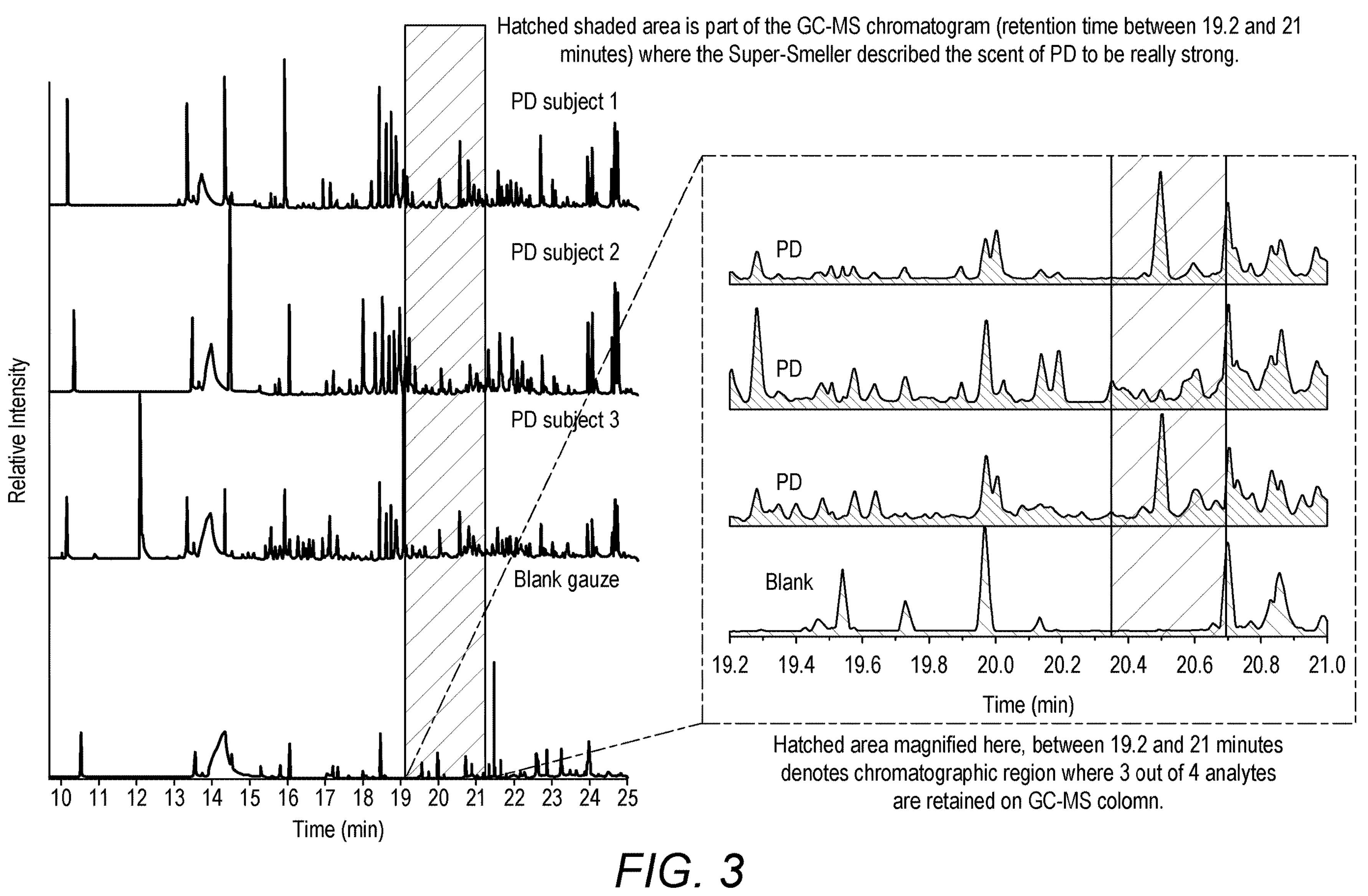

The samples from both cohorts were combined, thus increasing sample size and providing better statistical power while evaluating the performance of this panel of biomarkers. ROC curves were generated by Monte-Carlo cross validations (MCCV) using balanced sub-sampling. In each of the MCCV, two thirds of the samples were used to evaluate the feature importance. The top two, three, five, seven and nine important features were then used to build classification models, which were validated using the remaining one third of the samples. The process was repeated 500 times to calculate the average performance and confidence interval of each model. Classification and feature ranking was performed using a PLS-DA algorithm using two latent variables (FIG. 4). The results from the combined data indicate increased confidence in the data (p-values in Table 1 and confidence intervals in FIG. 1). When Olfactograms obtained from the odour port were overlaid on the total ion chromatograms (FIG. 3), many regions of interest (ROI) were identified. Due to individual variations between the These nine common biomarkers were selected for further analysis and statistical testing. To evaluate the performance of these common biomarkers from our discovery and validation cohort data, receiver operating characteristic (ROC) analysis was conducted with data from both the discovery cohort and the validation cohort. ROC curves and Wilcoxon-Mann-Whitney test as well as fold-change calculations on individual metabolites shows four out of these nine common metabolites had similar expression in PD between discovery and validation cohort and their performance was also similar as measured by AUC between discovery and validation cohort (see Table 4 below and FIG. 2).

TABLE 4

Panel of four volatile metabolites that were found to be differential between Parkinson's and control samples, with similar trends observed in expression and AUC curves measured by ROC analyses. Perillic aldehyde and Eicosane were significantly down-regulated and up-regulated in PD, respectively (FDR corrected p < 0.05).

| Putative | Parent | ΔRT | FDR corrected p-value (Mann-Whitney test) | | | Expression (PD/Control) | |
|---|---|---|---|---|---|---|---|
| identification | Mass | (min) | Discovery | Validation | Combined | Discovery | Validation |
| Perillic aldehyde | 150.22 | 0.15 | 0.0279 | 0.0403 | <0.0001 | Down | Down |
| Hippuric acid | 179.17 | 0.09 | 0.1908 | 0.0403 | 0.1833 | Up | Up |
| Eicosane | 282.56 | 0.03 | 0.0279 | 0.0403 | 0.0013 | Up | Up |
| Octadecanal | 170.34 | 0.12 | 0.2605 | 0.0604 | 0.3040 | Up | Up |

MSI (Metabolomics Standards Initiative) guidelines for data analysis were adhered to and for assignment of identity to features of interest [22]. All of our identified features were subjects, both in their exosome and endosomes, the perceived smell is expected to have variations between participants. However, several ROIs were consistently similar between the samples further indicating a similarity between PD individuals. The ROI between 19 and 21 min of the chromatographic run is of particular interest since the smell associated with the mixture of analytes between that retention window was described as "very strong" and "musky"—the scent of PD. This is the same region where three out of four common volatiles between the two cohorts have been detected viz. hippuric acid, eicosane and octadecanal. It should also be noted here that all three of these volatiles were up regulated in PD subjects. This may indicate that the presence of one or more of these compounds could be associated with the scent of PD.

From these results obtained from three independent sets of data, from different people with one underlying factor (i.e. PD) separating them, it was clear that several volatile features were found to be significantly different between control and PD participants. There were no significant differences observed between PD participants on medication and drug naïve PD participants, indicating that the majority of the analysed volatilome may not contain drug metabolites or sebum may be devoid of high concentrations of drug metabolites that can be associated with PD medication. Perillic aldehyde and octadecanal are ordinarily observed as plant metabolites or food additives. It can be hypothesised that with irregular sebum secretion these lipid-like hydrophobic metabolites may be altered on the skin of PD subjects. Such effects could be attributed to a direct change in metabolism resulting in dysregulated excretion of dietary metabolites such as eicosane in sebum or could be attributed to a metabolic change in PD skin, that may affect the skin microflora causing changes in the production of metabolites such as hippuric acid [23]. These observed effects may also be an indirect or secondary observation to the physiological manifestation of PD. This study highlights the potential of comprehensive analysis of sebum from PD patients and raises the possibility that individuals can be screened non-invasively based on their scent.

EXAMPLE 2—GAUZE—OPTIMIZATION OF EXTRACTION PROTOCOL FOR METABOLOMICS

Experiments were conducted to optimize and assess extraction protocol for gauze impregnated samples.

Extraction Procedure

For the extraction, 9 mL Toluene was added, falcon tube shaken for 1 hr, gauze hooked over metal wire and centrifuged for 10 mins (1500 rpm), dry gauze removed. For each extraction the solvent was split into 2× eppendorfs (1×LC, 1×GC) and dried down using a speedvac.

Comparison

The following comparisons were assessed:

- Blank gauze vs sample reconstituted in $H_2O$:ACN (50:50)
- Blank gauze vs sample reconstituted in $H_2O$:MeOH (50:50)
- Blank gauze vs day 1 sample vs day 2 sample (same subject)
- Blanks vs Sample (irrespective of resuspension method)

In total, 4 samples and 2 blanks were tested. The details of the extraction comparison experiments are shown in Table 5 below.

TABLE 5

| ID | Location | Day Taken | Samples Run | Reconstitution (200 uL) |
|---|---|---|---|---|
| 501 | Top RHS | 1 | 501 | $H_2O$:MeOH (50:50) |
| 505 | Top RHS | 1 | 505 | $H_2O$:ACN (50:50) |
| 503 | Top RHS | 2 | 503 | $H_2O$:MeOH (50:50) |
| 504 | Top RHS | 2 | 504 | $H_2O$:MeOH (80:20) |
| C1B | — | — | C1B | $H_2O$:ACN (50:50) |
| C2B | — | — | C2B | $H_2O$:MeOH (50:50) |

Figure 13:
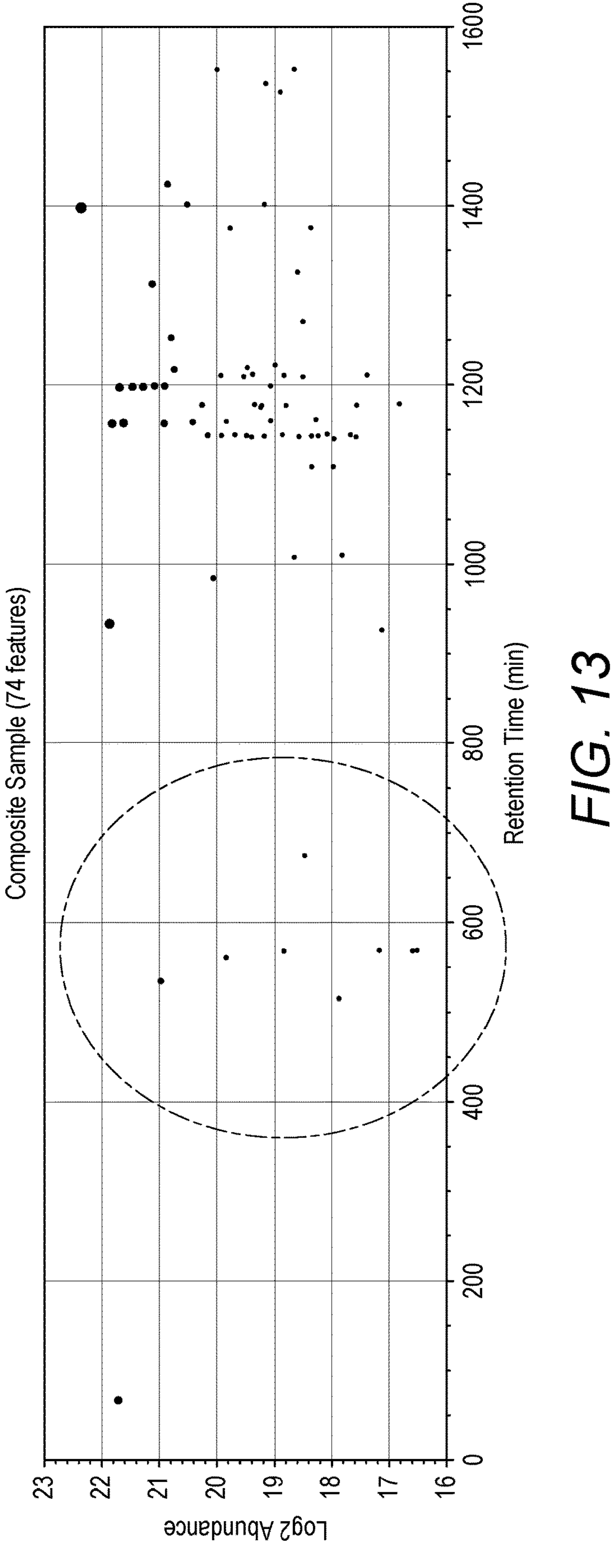
FIG. 13 shows a plot of the number of features higher in blank in the PEG area.

FIGS. 5 to 14 show the results of the comparison experiments. In particular, FIG. 13 shows that if the PEG background was interfering with signal, we would expect to see a lot more metabolite here because in this graph we are plotting any peak that is 2 folds higher i.e. considered as a very high noise. The signal seems to be higher in the same RT region, where high PEG was suspected. This indicates we can safely eliminate any gauze related background issues.

Figure 14:
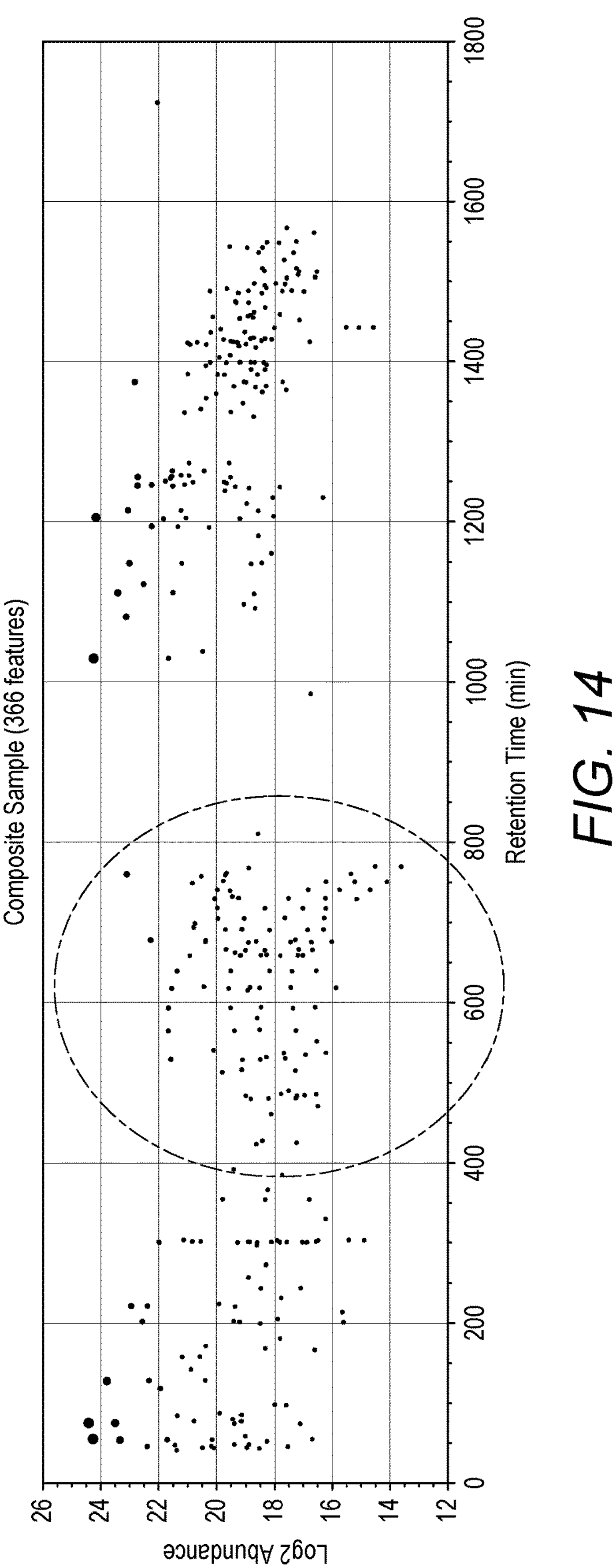
FIG. 14 shows a plot of the number of features higher in samples in the PEG area.

FIG. 14 shows Granted approximately 10 features are masked by PEG, we have about a hundred that aren't i.e. signal-to-noise ratio is much higher and any PEG-like contamination that may come off from gauze can be avoided by this extraction.

EXAMPLE 3—EXTRACTION PROTOCOL OPTIMISATION

Experiments were conducted in order to optimize the extraction protocol using different solvents.

Toluene Extraction

Toluene was established as not compatible with filters for the removal of gauze residue. Toluene cannot be removed in speedvac—especially in such high volumes. It was found to damage the seals on common speedvacs in labs.

Especially for scaling the procedure to high sample numbers: evaporation in a fume-hood would not be feasible and leaving eppendorfs (with no lid) over long periods in communal labs is not good practice. Whilst, using a heat block to speed up removal of the solvent was assessed, this did not speed up the evaporation to a reasonable speed at lower temperatures and high temperatures could be detrimental to sample integrity.

Due to these issues, the reconstitution composition was difficult to optimise, and was not consistent between samples.

FIG. 15A shows that solid residue formed during reconstitution in Toluene:Methanol (20:80). The addition of chloroform followed by centrifugation (×2 steps) allowed a clear supernatant to be obtained.

FIG. 15B shows that solid substance was formed on reconstitution in Toluene:Methanol (50:50).

Folch Extraction

It was assessed that this solvent combination was not compatible with filters to remove gauze residue. The chloroform layer for LC-MS did not reconstitute back into Water:Methanol (80:20) and formed a cloudy solution Whilst adding chloroform during reconstitution was assessed, too much volume was needed to be viable, multiplying the number of centrifugation cycles lost too much sample Methanol Extraction In this extraction protocol, 9 mL, 15 mL and 20 mL solvent extraction volumes were tested. It was established that the lower solvent yielded the highest signal and that a minimum of 9 mL was needed due to the gauze size the volume of solvent it absorbs.

Ordinarily the samples extracted in organic solvents, can be reconstituted back into organic solvents. For example, samples extracted in methanol and then dried down to form a pellet should normally reconstitute back in methanol and also ethanol, acetonitrile or isopropanol. However, we have discovered that lipids and lipid-like molecules extracted by our protocol, tend to destabilise under methanol over long period of time. In metabolomics, or LC-MS analyses, the norm is to reconstitute the extracts in various combinations (%) of water and methanol. However, this destabilised our analytes and it ended up forming solid residues shown in above photos, after a short period of time. This was reproduced even when the samples were stored at ambient temperature and on a cold tray. A mixture of organic solvents was assessed and methanol and ethanol (50:50 v/v) stabilises the reconstituted sebum. This indicates that the molecules extracted from sebum are atypical and requires a combination of organic solvents as opposed to organic-aqueous mixture or single organic solvent to stay in solution.

EXAMPLE 4—PREFERRED EXTRACTION PROTOCOLS

It was therefore established that the following extraction protocol had the best performance:

Q-Tip Extraction

1. Snap wooden stem of QTip into a 2 mL eppendorf
2. Add 1 mL MeOH
3. Vortex for 10 seconds
4. Sonicate for 10 minutes
5. Remove QTip
6. Centrifuge for 5 mins
7. Pipette 800 uL into a new eppendorf (split in half if needing two fractions)
8. Dry in speedvac concentrator for ~6 hrs
9. Store in −80 deg freezer Gauze Extraction 1) Using tweezers place gauze in 50 mL falcon tube
2) Add 9 mL methanol, shake till gauze is at bottom of tube
3) Vortex for 10 seconds
4) Sonicate for 30 minutes
5) Pipette extracted methanol from gauze tube
6) Use a syringe and filter for the extracted solvent into a new tube—recovery ~7 mL
7) Split this into 3×2 mL fractions in eppendorfs
8) Dry for ~10/12 hrs using speedvac concentrator
8) Store in −80 deg

EXAMPLE 5—PAPER SPRAY IONIZATION MASS SPECTROMETRY OF HUMAN SEBUM FOR PARKINSON'S DISEASE DIAGNOSTICS

Study Participants

For initial method development of paper spray ionization mass spectrometry (PSI-MS) using sebum, samples from healthy controls were used. After achieving a satisfactory reproducibility of the mass spectra collected from human sebum, the method was further tested using samples from participants with Parkinson's disease. The participants for this study were part of a recruitment process taking place at 28 different NHS clinics all over the UK. A subset from a larger recruitment drive was used for this work (65 PD and 52 control samples) collected from a local clinic (also involved in Parkinson's disease research).

Sample Collection

Sebum samples were non-invasively swabbed from the upper/lower back of participants with medical Q-tip swabs. Then the Q-tip swabs with the sebum sample were secured in their individual caps and transported in sealed envelopes to the central facility at the University of Manchester where they were stored at −80° C. until the date of analysis.

Method: Paper Spray Ionization Mass Spectrometry (PSI-MS)

For all PSI-MS experiments, commercially available Whatman filter papers (grade 1 and 42) were used as the paper substrates. Sebum samples were transferred from the Q-tip swabs to the paper substrates by a gentle rub. After sample transfer, the paper was cut into a triangle (5 mm at the base and 10 mm in height). Then the paper triangle was carefully clipped to a copper alligator clip using tweezers. Careful handling of the paper was important to avoid contamination. The copper clips were cleaned by sonication in acetone before use. For each sample, a new clip and tweezers were used to avoid cross-contamination across the samples. Then the clip was connected to a home-built paper spray holder which was adapted to an existing mass spectrometer for PSI-MS measurements followed by placing the holder in front of the MS inlet using an adjustable stage. The holder was adjusted in such a way that the paper tip is at a 5-7 mm distance from the MS inlet. After placing the paper triangle at a desirable position, a high voltage in the range of 2.5-3 kV was applied to it through the clip. When the paper, held at an elevated potential, was eluted with a polar solvent, a Taylor cone formation was observed at the tip of the paper which was immediately followed by observable m/z signals in the instrument software. All the mass spectra were recorded in the range of 50-2000 m/z. The main instrumental parameters for each PSI-MS experiment were set as capillary voltage 3 kV, source temperature 100° C., sampling cone 30 V and source offset 40 V. No desolvation or cone gas was used.

Use of Internal Standard

To check the reproducibility of paper spray across different samples, an internal standard was used. For these experiments, 3.5 μL of the internal standard solution was spotted on paper triangles and ambiently air dried. Dried paper triangles were used for PSI-MS measurements of sebum samples following an identical method described in the previous paragraph.

Data Processing

The data were recorded in Waters proprietary format. Total analysis time per sample was 120 scans in 2 minutes. These 120 scans were aggregated as a single, combined spectrum. The combined spectrum was recorded in a tabulated format for each sample such that each row had the m/z value measured and the absolute ion count. These data were generated for all the files in the experiment. The data were then saved in .csv format for each file individually.

Further data processing was done using the open-source statistical software R. In-house script was written to import .csv files into R as a data frame. Each m/z was binned using two steps—firstly, if the m/z was unique in a sample, it was preserved and if the m/z had already been detected in a previous sample, it was combined. The resulting data frame had all the possible m/z values detected across the entire dataset. In the next step, m/z values were rounded to the most accurate representation of instrumental measurement i.e. up to 4 decimal places in Dalton mass. Finally, consecutive m/z values were considered to be representative of the same ion if they were identical and their peak areas were summed. The resultant data were combined into a single matrix where each row showed an m/z value and the total ion count and each column represented a sample.

Data Analysis

Data reproducibility and quality were assessed using internal standard peak intensities for paper spray. Internal standard reference peaks were detected in all samples. The quality of data was determined by the coefficient of variance of internal standard peak ratios. A one-way t-test was used to determine significant differences between the means of each variable for control and PD samples. Every variable with $p<0.05$ was considered significant and was carried forward for putative identification. Putative identification was carried out by matching the m/z values with values in online databases—Human Metabolome Database (HMDB) and LipidMaps with a mass accuracy of 20 ppm.

Results and Discussion

FIG. 16 shows a schematic representation of the experimental workflow for analysing human sebum samples using the PSI-MS technique. Whatman grade 1 and 42 were used for PSI-MS analysis and both of the papers showed identical results (FIG. 17). Different solvents and solvent mixtures were tested for generating stable and reproducible spray. After a considerable number of tests, 4:1 $H_2O$/EtOH was chosen as the optimized solvent system for the best results in this particular study. The distance between the tip of the paper and the MS inlet was also optimized by trial and error. After placing the paper tip at an optimum distance from the MS inlet, it was eluted with 4.5 μL of solvent. Mass spectra were recorded for two minutes at a scan rate of 2 sec/scan. A total of 60 scans was used for further data analysis. The inset of FIG. 16 shows a representative mass spectrum collected from human sebum. Mass spectra of human sebum show the presence of three envelopes at the higher mass region (m/z 1200-1800) consisting of singly charged peaks. PSI-MS has been used to detect small molecules present in biofluids like blood, urine, etc. This study, for the first time, shows that sebum can be used as a sampling biofluid for PSI-MS and that it enables the detection of skin surface molecules with a significantly higher molecular mass of <1200 m/z. Ion mobility-mass spectrometry (IM-MS) was also employed to further evaluate these high molecular weight metabolites and specifically to resolve conformational isomers and isobaric structural isomers as has been previously reported for lower molecular weight lipids (NATURE COMMUNICATIONS|(2019) 10:985|https://doi.org/10.1038/s41467-019-08897-5). FIG. 18 shows an example of the enhanced separation and diagnostic features (both in higher and lower mass regions) that can be found from the combination of ion mobility and mass spectrometry.

Figures 18A, 18B:
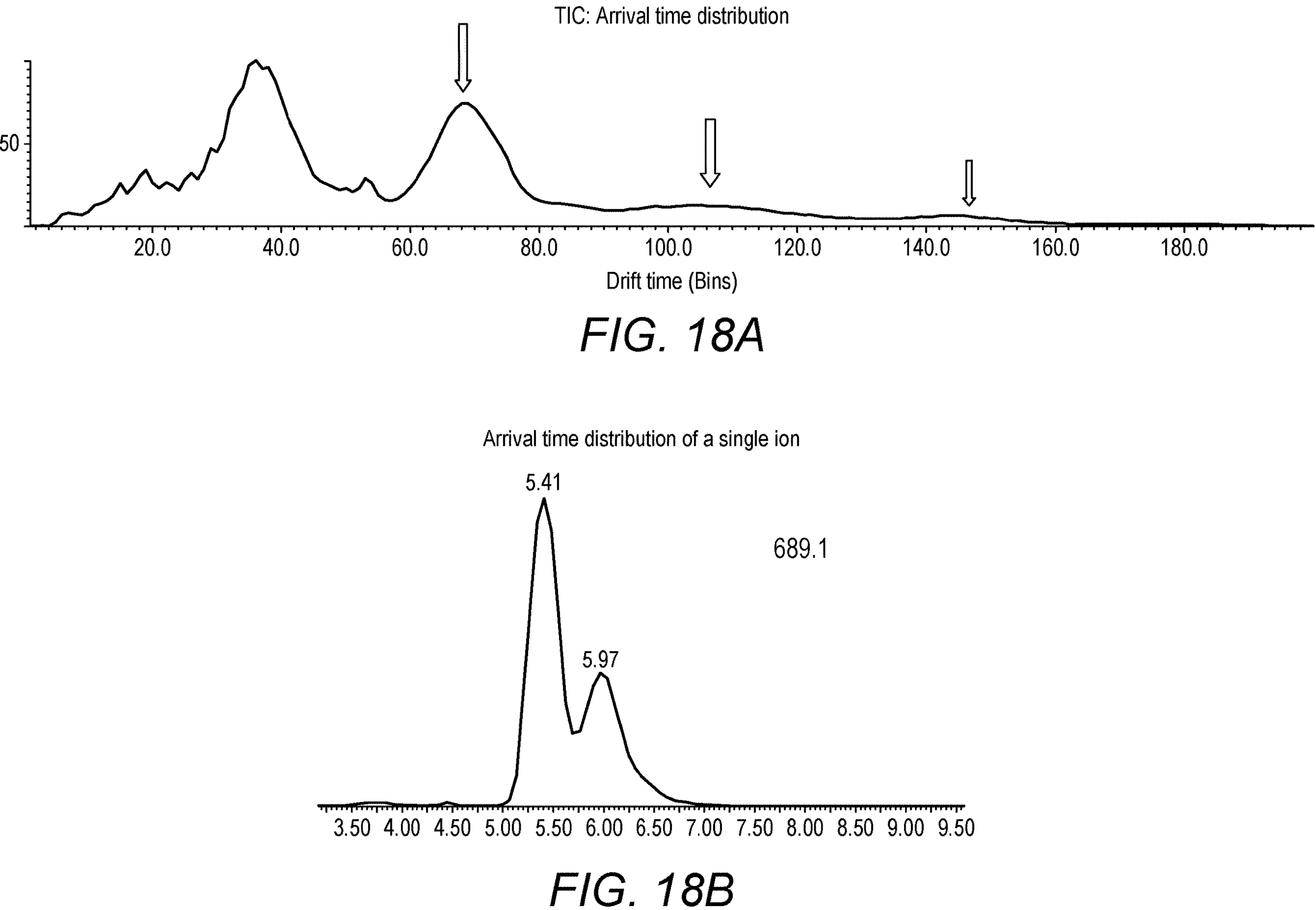
Figure 18C:
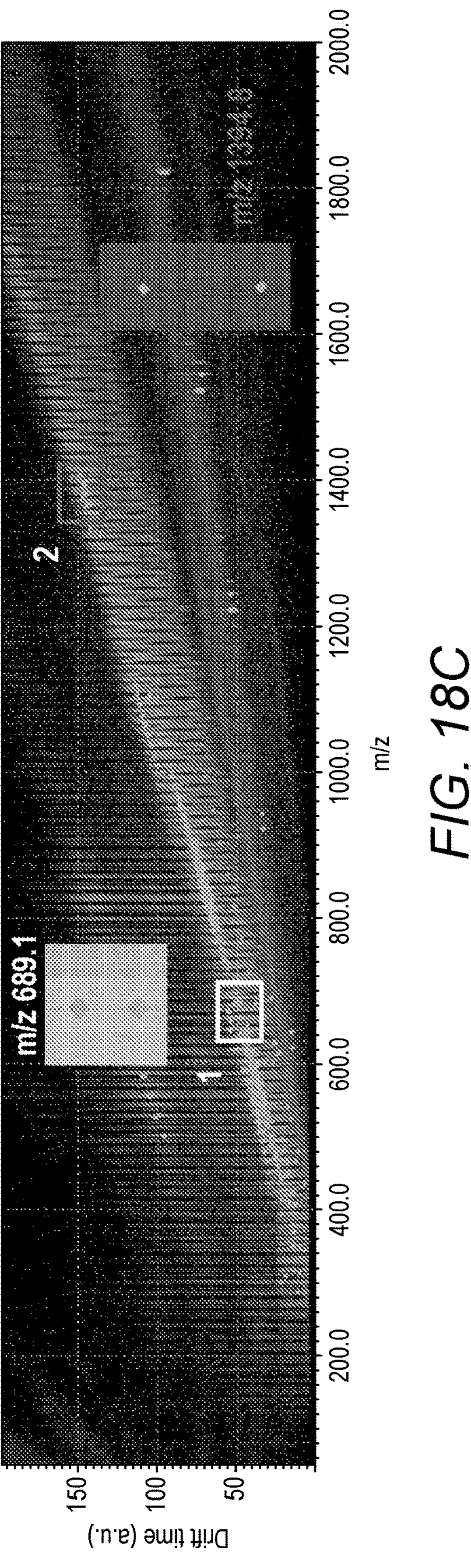

FIG. 18A shows a total ion chromatogram with respect to the arrival time distribution of different ions. The arrows indicate clear separation of the generated ions (identified as lipids) with respect to drift time. FIG. 18B shows the arrival time distribution of a single ion (m/z 689.1). The existence of two peaks on the drift time scale for a single m/z value indicates the possibility of the presence of an isomeric species. FIG. 18C shows a drift time vs m/z plot where the dots represent the m/z values. The dots (in the boxes labeled 1 and 2 respectively) in the insets show a zoomed view of m/z 689.1 (highlighted with box 1) and m/z 1394.8 (highlighted with box 2) which are separated in the drift time scale. This data shows that IM combined with PSI-MS could be used to separate gas-phase ions generated from human sebum samples.

After recording mass spectra from all of the participant samples under identical conditions, data were processed and statistical analysis was performed as outlined earlier. Table 6 shows the m/z values along with the probable molecular species of the statistically important molecules within our data. Interestingly, it was possible to identify a class of molecule known as cardiolipins (represented as CL in Table 6) which is predominant in the list of statistically important molecules.

TABLE 6

List of statistically important m/z values along with probable molecular species within our data set

| m/z | Proposed molecule | Chemical formula | Possible ion |
|---|---|---|---|
| 1668 | CL(68:0) | $C_{77}H_{150}O_{17}P_2K$ | [M + K]+ |
| 1644 | CL(74:6) | $C_{83}H_{150}O_{17}P_2K$ | [M + K]+ |
| 1632 | CL(72:4) | $C_{81}H_{150}O_{17}P_2K$ | [M + K]+ |
| 1628 | CL(76:11) | $C_{85}H_{144}O_{17}P_2$ | |
| 1622 | CL(74:8) | $C_{83}H_{146}O_{17}P_2Na$ | [M + Na]+ |
| 1620 | CL(72:5) | $C_{81}H_{148}O_{17}P_2Na_2$ | [M + 2Na − H]+ |
| 1616 | CL(70:2) | $C_{79}H_{150}O_{17}P_2K$ | [M + K]+ |
| 1604 | CL(76:9) | $C_{85}H_{148}O_{17}P_2Na$ | [M + Na]+ |
| 1598 | CL(74:6) | $C_{83}H_{150}O_{17}P_2Na_2$ | [M + 2Na − H]+ |
| 1596 | CL(74:7) | $C_{83}H_{148}O_{17}P_2Na$ | [M + Na]+ |
| 1592 | CL(72:4) | $C_{81}H_{150}O_{17}P_2Na_2$ | [M + 2Na − H]+ |
| 1580 | CL(78:12) | $C_{87}H_{146}O_{17}P_2$ | |
| 1574 | CL(76:10) | $C_{85}H_{146}O_{17}P_2$ | |
| 1572 | CL(72:7) | $C_{81}H_{144}O_{17}P_2$ | |
| 1568 | CL(70:4) | $C_{79}H_{146}O_{17}P_2Na$ | [M + Na]+ |
| 1556 | CL(68:1) | $C_{77}H_{148}O_{17}P_2Na_2$ | [M + 2Na − H]+ |
| 1550 | CL(78:10) | $C_{87}H_{150}O_{17}P_2Na_2$ | [M + 2Na − H]+ |
| 1548 | CL(78:12) | $C_{87}H_{146}O_{17}P_2Na$ | [M + Na]+ |
| 1548 | CL(76:9) | $C_{85}H_{148}O_{17}P_2Na_2$ | [M + 2Na − H]+ |
| 1532 | CL(72:6) | $C_{81}H_{146}O_{17}P_2$ | [M + H − H2O]+ |
| 1526 | CL(74:9) | $C_{83}H_{144}O_{17}P_2$ | [M + H]+ |
| 1526 | CL(72:6) | $C_{81}H_{146}O_{17}P_2Na$ | [M + Na]+ |
| 1520 | CL(70:3) | $C_{79}H_{148}O_{17}P_2Na_2$ | [M + 2Na − H]+ |
| 1511 | CL(76:8) | $C_{85}H_{150}O_{17}P_2Na_2$ | [M + 2Na − H]+ |
| 1508 | CL(72:5) | $C_{81}H_{148}O_{17}P_2Na$ | [M + Na]+ |
| 1502 | CL(70:2) | $C_{79}H_{150}O_{17}P_2Na_2$ | [M + 2Na − H]+ |
| 1502 | CL(74:8) | $C_{83}H_{146}O_{17}P_2$ | [M + H − $H_2O$]+ |
| 1500 | CL(70:3) | $C_{79}H_{148}O_{17}P_2Na$ | [M + Na]+ |

TABLE 6-continued

| m/z | Proposed molecule | Chemical formula | Possible ion |
|---|---|---|---|
| List of statistically important m/z values along with probable molecular species within our data set | | | |
| 1500 | CL(68:0) | $C_{77}H_{150}O_{17}P_2Na_2$ | [M + 2Na − H]+ |
| 1500 | CL(68:3) | $C_{77}H_{144}O_{17}P_2$ | [M + H]+ |
| 1496 | CL(66:0) | $C_{75}H_{146}O_{17}P_2Na$ | [M + Na]+ |
| 1488 | CL(78:10) | $C_{87}H_{150}O_{17}P_2K$ | [M + K]+ |
| 1478 | CL(70:5) | $C_{79}H_{144}O_{17}P_2$ | [M + H]+ |
| 1478 | CL(68:2) | $C_{77}H_{146}O_{17}P_2Na$ | [M + Na]+ |
| 1476 | CL(68:2) | $C_{77}H_{146}O_{17}P_2$ | [M + H − $H_2O$]+ |
| 1476 | CL(66:1) | $C_{75}H_{144}O_{17}P_2$ | [M + H]+ |
| 1476 | CL(70:4) | $C_{79}H_{146}O_{17}P_2$ | [M + H − $H_2O$]+ |
| 1472 | CL(80:12) | $C_{89}H_{150}O_{17}P_2Na_2$ | [M + 2Na − H]+ |
| 1466 | CL(66:0) | $C_{75}H_{146}O_{17}P_2$ | [M + H − $H_2O$]+ |
| 1464 | CL(80:12) | $C_{89}H_{150}O_{17}P_2K$ | [M + K]+ |
| 1460 | CL(20:4) | | |
| 1454 | Ganglioside GM1 (d18:0/24:0) | | |
| 1454 | Dihydro-4-mercapto-3(2H)-furanone | | |
| 1452 | 2,3-Dihydrothiophene | | |
| 1452 | Methyl 2-furoate | | |
| 1452 | Ganglioside GM1 (d18:0/25:0) | | |
| 1448 | 6-({5,7-dihydroxy-2-[4-hydroxy-3-(sulfooxy)phenyl]-4-oxo-4H-chromen-3-yl}oxy)-3,4,5-trihydroxyoxane-2-carboxylic acid | | |
| 1442 | Malic acid | | |
| 1440 | CL(84:19) | | |
| 1436 | 3-(3,4-dihydroxyphenyl)-2-(sulfooxy)propanoic acid | | |
| 1430 | CL(88:23) | | |
| 1428 | CL(68:0) | | |
| 1428 | | | |
| 1418 | CL(18:0/22:5(7Z, 10Z, 13Z, 16Z, 19Z)/20:4(5Z, 8Z, 11Z, 14Z)/22:5(4Z, 7Z, 10Z, 13Z, 16Z)) | | |
| 1416 | Trifluoroacetic acid | | |
| 1412 | CL(22:6(4Z, 7Z, 10Z, 13Z, 16Z, 19Z)/22:5(4Z, 7Z, 10Z, 13Z, 16Z)/22:6(4Z, 7Z, 10Z, 13Z, 16Z, 19Z)/22:5(4Z, 7Z, 10Z, 13Z, 16Z)) | | |
| 1404 | CL(22:6(4Z, 7Z, 10Z, 13Z, 16Z, 19Z)/20:4(5Z, 8Z, 11Z, 14Z)/22:6(4Z, 7Z, 10Z, 13Z, 16Z, 19Z)/22:5(7Z, 10Z, 13Z, 16Z, 19Z)) | | |
| 1404 | Anagrelide (15 ppm) | | |
| 1388 | Uric acid | | |
| 1388 | CL(16:0/18:1(11Z)/16:0/18:1(11Z)) | | |
| 1380 | Bissulfine | | |
| 1368 | 4-Nitrophenyl phosphate | | |
| 1364 | Fluorouracil (21 ppm) | | |
| 302 | Phenylpropiolic acid | | |
| 301 | CL(16:0/22:6(4Z, 7Z, 10Z, 13Z, 16Z, 19Z)/22:6(4Z, 7Z, 10Z, 13Z, 16Z, 19Z)/22:5(4Z, 7Z, 10Z, 13Z, 16Z)) | | |
| 288 | CL(22:5(4Z, 7Z, 10Z, 13Z, 16Z)/20:4(5Z, 8Z, 11Z, 14Z)/22:5(4Z, 7Z, 10Z, 13Z, 16Z)/20:4(5Z, 8Z, 11Z, 14Z)) | | |
| 284 | Malathion monocarboxylic acid | | |
| 257 | CL(i-13:0/i-21:0/i-17:0/i-16:0) | | |
| 256 | CL(i-13:0/i-20:0/i-18:0/18:2(9Z, 11Z)) | | |
| 243 | N-Acetylglucosaminyl-diphosphodolichol | | |
| 220 | CL(i-13:0/i-21:0/i-17:0/i-16:0) | | |
| 215 | Sinalexin | | |
| 213 | CL(i-13:0/i-20:0/18:2(9Z, 11 Z)/18:2(9Z, 11Z)) | | |
| 201 | CL(18:2(9Z, 12Z)/22:5(7Z, 10Z, 13Z, 16Z, 19Z)/22:5(7Z, 10Z, 13Z, 16Z, 19Z)/20:4(5Z, 8Z, 11Z, 14Z)) | | |
| 200 | CL(22:6(4Z, 7Z, 10Z, 13Z, 16Z, 19Z)/18:1 (9Z)/22:6(4Z, 7Z, 10Z, 13Z, 16Z, 19Z)/18:1 (9Z)) | | |
| 199 | N-Methylformamide | | |
| 185 | Dimethylthiophosphate | | |
| 173 | CL(a-13:0/18:2(9Z, 11 Z)i-22:0/1 8:2(9Z, 11Z)) | | |
| 171 | CL(a-13:0/i-22:0/18:2(9Z, 11 Z)/18:2(9Z, 11Z)) | | |
| 157 | CL(i-13:0/i-20:0/i-18:0/18:2(9Z, 11Z)) | | |
| 141 | Mechlorethamine (10 ppm) | | |
| 131 | Dihydro-4-mercapto-5-methyl-3(2H)-thiophenone | | |
| 115 | 4-Ketocyclophosphamide | | |
| 113 | 3-Oxoglutaric acid | | |
| 98 | 1-benzofuran-4-ol | | |
| 96 | 4-Mercapto-5-methyl-3(2H)-thiophenone | | |
| 90 | S-Propyl thiosulfate | | |
| 88 | Risedronate (29 ppm) | | |
| 75 | Acrylic acid | | |
| 74 | Ethyl formate | | |
| 72 | Thelephoric acid | | |
| 71 | Thiophene (10 ppm) | | |
| 67 | trans-3-Chloro-2-propene-1-ol | | |
| 66 | 2-Furancarboxaldehyde | | |
| 59 | (4-ethenyl-2,6-dihydroxy phenyl)oxidanesulfonic acid | | |

A comparative study was performed between the PD and control samples considering these molecules. It was observed that these molecules are down-regulated in PD sebum. FIG. 19 shows the comparison of m/z 1668 and 1520 (putatively identified as cardiolipins) and m/z 1452 and 1454 (putatively identified as ganglioside) between PD and control samples.

Upon a closer look at the IM-MS data, a number of species could be identified that were up-regulated in the PD samples. Table 7 shows the m/z values and respective drift times for these species.

TABLE 7

List of statistically important m/z values that are also significantly different (in PD samples vs controls) with respect to drift time.

| m/z | Drift time (ms) PD | | Control | |
|---|---|---|---|---|
| 815.6791 | 10.11 | 6.51 | 10.11 | Absent |
| 829.6871 | 10.36 | 6.58 | 10.32 | Absent |
| 843.6967 | 10.53 | 6.86 | 10.53 | Absent |
| 857.7026 | 10.66 | 6.93 | 10.66 | Absent |
| 867.7198 | 10.87 | 6.86 | 10.87 | Absent |

FIG. 20 shows m/z vs drift time plots (data was averaged over 34 PD and 30 control samples) for the above ions. The arrows indicate the ions with the same m/z values but different drift times in PD samples (absent in controls). This data shows the potential of PSI-MS combined with ion mobility for Parkinson's disease diagnostics.

EXAMPLE 6—THERMAL DESORPTION GAS CHROMATOGRAPHY MASS SPECTROMETRY (TD-GC-MS)

Instrumentation

Gauze swabs (HypaCover) were transferred into 20 mL headspace vials and pushed down using Gilson pipette tips while wearing nitrile gloves. The Gerstal MultiPurpose Sampler (MPS) was used for concentration of volatile compounds. The arm transports samples from the tray to the Dynamic Headspace (DHS) port where they are incubated and inert gas purged through the headspace to collect volatile compounds. A Tenax sorbent tube (Gerstal, Germany) is placed above the vial and the purged gas flows through, trapping the volatile analytes. The Tenax is then transported to the GC inlet where the Thermal Desorption Unit (TDU) is located. The sorbent tube is desorbed by heating and the volatile compounds enter the Cooled Injection System (CIS) which heats up quickly to allow analytes to be injected to the GC column uniformly. Our QC was a mixture of scented molecules of which 5 uL was pipetted into a headspace vial. We could not pool samples so the QC was used to check instrument stability.

Method Details

In the DHS the samples were incubated and volatile compounds concentrated. The vials were heated for 10 min at 80 degrees. This was followed by purging with 1000 mL of nitrogen gas at flow rate 70 ml/min. The Tenax sorbent tube was kept at 40 degrees. The Tenax was then transported to the TDU which was in splitless mode. The analytes were desorbed and released to the CIS at a temperature program 30° C. for 1 min then at a rate of 720° C./min to a temperature of 280° C. and held for 5 mins. The CIS was operated in solvent vent mode using a flow of 80 mL/min and a split ratio of 10. The temperature of the CIS was 10° C. for 0.01 min and ramped at 12° C./sec to 280° c. and held for 5 min.

The GC used in the analysis was an Agilent 7890A with a VF-5MS column (30 m×250 um×0.25 um) and helium as the carrier gas. Column flow was 1 ml/min and oven program was 40° C. for 1 min, 25° C./min to 180° C., 8° C./min to 240 held for 1 min, 20° C./min to 300 and held for 2.9 min. The total run time was 21 minutes. The GC was coupled to an Agilent 5975 MS operating in EI mode. The transfer line was kept at 300° C., the source at 230 and the quadrupole at 150. The mass range scanned was 30-800 m/z. Our QC was run on an altered method to optimise signal and separation while running on as short a method as possible: the DHS incubated at 80° C. for 2 minutes and purged with 250 mL gas at 50 mL/min. In the TDU the temperature program was 30° C. for 1 min then ramped at 600° C./min to 250° C. where it was held for 3 minutes. The CIS had flow of 60 mL/min and a split ratio of 20, the temperature was 10° C. for 0.1 min and increased at 10° C./sec to 240° C. and held for 2 mins. The oven program was 40° C. for 1.5 min 24° C./min to 280° C. and held for 2 min (13.5 min total). The mass range scanned was 30-550 m/z and the transfer line was held at 280° C.

Data Processing

TD-GC-MS data were converted to open source mzML format using ProteoWzard. The dataset was deconvolved using in-house script with eRah package in R, which yielded 206 features assigned to detected peaks. The deconvolved analytes were assigned putative identifications by matching fragment spectra with compound spectra using the Golm database. The resulting matrix was comprised of variables and their corresponding peak area per sample. Features that were absent in more than 5% of all samples were removed. The resulting data were normalized to total ion count and log transformed prior to statistical analysis.

Results

Using all data generated using TD-GC-MS, each m/z was treated as a separate ion species and clustering techniques were used to identify underlying similarity within groups and dissimilarity between groups. Supervised multivariate approach—principal component discriminant factor analysis was used. In this approach principal components are first calculated to reduce dimensions of the data followed by discriminant analysis of these components. This provides dimension reduction, while still maintaining variance and discriminatory power is checked using factor analysis. FIG. 21 shows, three distinct clusters of three different phenotypes that are observed. This indicates that measured metabolites/lipids using TD-GC-MS have distinct characteristic (intensity or presence/absence) in prodromal, control and PD phenotypes. These data were used to create machine learning models viz. Support Vector Machines (SVM). The aim was to determine classification accuracy of these measured m/z in determining class of a participant sebum sample. From tables, it is clear that this measurands can with 71% and 74% correct classification rate, distinguish between prodromal sample and control sample as well as prodromal and PD sample. This indicates we are able to differentiate clearly participants who have prodromal symptoms but do not have PD by a skin swab. We note, there were mainly high m/z species shown in FIGS. 22 & 23, that were distinctly different by phenotypes.

EXAMPLE 7—PAPER SPRAY IONIZATION & ION MOBILITY MASS SPECTROMETRY (PSI-IM-MS)

Study Participants

Initially, a method for paper spray ionization-ion mobility mass spectrometry (PSI-IM-MS) was developed using sebum samples from healthy controls. Ethical approval for this project (IRAS project ID 191917) was obtained by the NHS Health Research Authority (REC reference: 15/SW/0354). For the clinical study data set, sebum samples were collected from PD (15), control (14), and prodromal participants (15) were collected at a collection site in Innsbruck.

Sample Collection

Sebum samples were swabbed from the upper back of participants with medical Q-tip and gauze swabs. Then the swabs with sample were secured in its individual caps/zip lock bags (in case of gauze) and transported in sealed envelopes to the central facility at the University of Manchester, where they were stored at −80° C. until the date of analysis.

Instrument Setup

For PSI MS measurements, sebum samples were transferred from the Q-tip swabs onto the paper triangle by gentle touch followed by carefully clipping onto the copper alligator clip using tweezers. Careful handling of the paper was essential to avoid contamination. PSI MS was performed using a home built paper spray source mounted on a movable stage. After placing the paper triangle at a desirable position, a high voltage in the range of 2.5-3 kV was applied to it. Upon elution with a polar solvent at that elevated potential, spray plume of tiny charged droplets was observed at the tip of the paper which was recorded as m/z signals in the instrument software. All the mass spectra were recorded in the range of m/z 50-2000. The main instrumental parameters for each PSI MS experiments were set as capillary voltage 3 kV, source temperature 100° C., sampling cone 30 V and source offset 40 V. No desolvation or cone gas was used. Mass spectra were recorded for two minutes at a scan rate of 2 sec/scan. A total of 60 scans was used for further data analysis.

Data Processing

After recording IM MS data from all the participant samples under identical conditions, the raw data were deconvolved using Progenesis QI (Waters, Wilmslow, UK). Peak picking, alignment, and area normalization were carried out with reference to the best candidate sample, within the data set, chosen by set of parameters. Peak picking limits were set to automatic with default noise levels, to balance signal to noise ratio. Chromatographic peak width was not applied to this direct infusion data however ions before 0.1 minutes of infusion and 1.4 minutes after infusion were ignored during processing to only retain reproducible signal. Using these parameters a total of 4150 features were found. Features extracted from raw data were annotated using a mass match with the Human Metabolome Database (HMDB) and LipidMaps.

Method

Figure 22A:
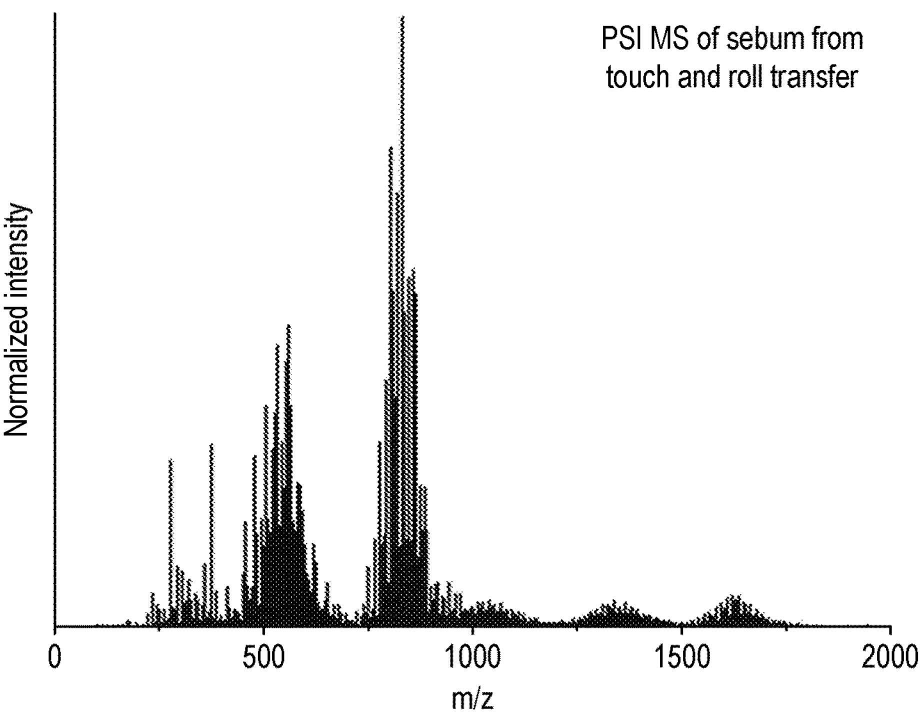
Figure 22B:
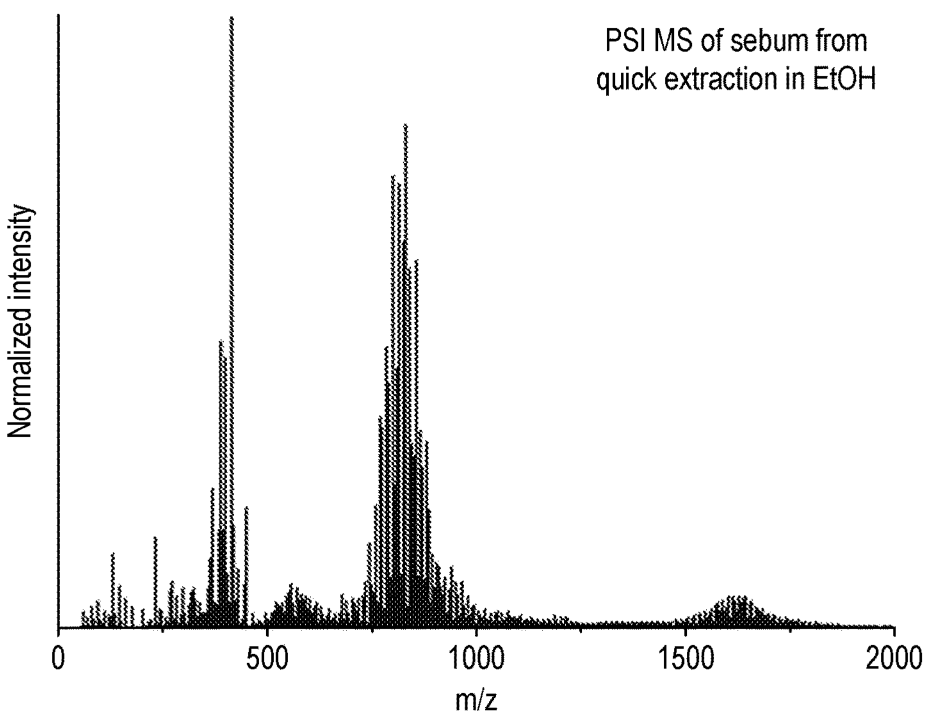

A reproducible method of measuring mass spectra of sebum samples using PSI MS was developed with an empirical approach. The crucial part of the method development was the sample transfer from the Q-tip to the paper substrate. Two methods were tested, firstly, direct transfer to the paper triangle in a 'touch and roll' approach followed by recording PSI MS from it and alternatively a rapid solvent extraction via vortex-mixing the sampled Q-tip in ethanol (800 μL) for 5 s. In the second case, PSI MS was measured from the extracted solution. FIG. 21 shows the mass spectra collected using these two approaches, which clearly indicates the presence of higher mass molecules (between m/z 1200-2000) in the touch and roll transfer mass spectrum (FIG. 22B). On the other hand, these higher-mass molecules were absent in the mass spectrum corresponding to the solvent extract (FIG. 22A). The following two reasons can be speculated for this: either the extraction time was too short to fully extract all metabolites present or due to degradation of these larger molecules to smaller fragments. Hence the touch and roll approach was chosen for all further sebum analyses using PSI MS.

Mass spectra of human sebum show the presence of three envelopes of singly charged species in the higher mass region (m/z 700-1800). These envelopes are a series of peaks differing by 14 Da. A zoomed mass spectra in the m/z region 800-1000 is shown in FIG. 23.

Ion mobility-mass spectrometry (IM MS) was employed to further evaluate these high molecular weight metabolites, and specifically to resolve conformational isomers and isobaric structural isomers as has been previously reported for lower molecular weight lipids. Interestingly, we could identify a class of molecules known as lipids is predominant in the list of statistically important (among PD, control, and prodromal cohorts ($p<0.05$)) molecules. These were 500 features out of the total of 4150 deconvolved features. While analyzing the drift time vs. m/z (DT vs. m/z) plots for the statistically important molecules a significant difference between the PD, control, and prodromal samples were observed for certain class of molecules (identified as lipids, data on the support of this is discussed in the latter part).

Figures 25A, 25B, 25C, 25D:
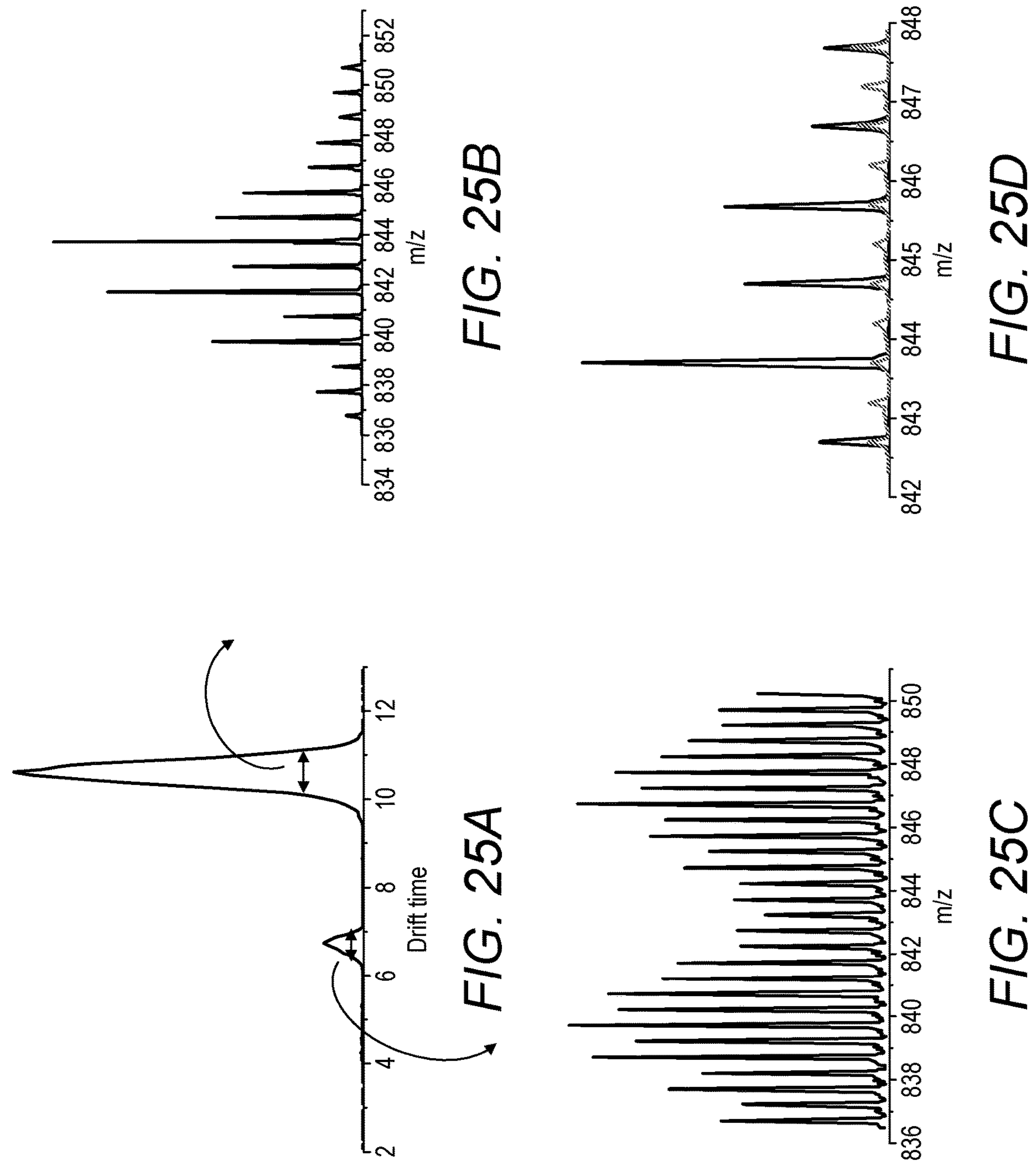

From the above analysis, a subset of statistically important features ($p<0.05$) were identified to have a drift time peak at specific m/z values that were only present in PD and prodromal samples and absent in controls. FIG. 24 shows few examples of three-dimensional DT vs. m/z plots in the m/z 700-900 region for PD (blue boxes) and control (magenta boxes), and prodromal (orange boxes) samples. The red arrows indicate a particular drift time (6.67 ms) at which certain molecular species were observed in PD and prodromal samples but which were absent in the control samples. The cluster of peaks in FIG. 24 represent isotopic distributions for a single ion. The peaks at the higher drift time (10.43 ms) represent an isotopic distribution of a singly charged monomeric species and the trace at the lower drift time (6.67 ms) in case of PD and prodromal samples corresponds to an adduct of a dimeric species with 2+ charge. As the charge state of an ion is a predominant factor in ion mobility separation, despite the shorter DT species being dimeric it travels quicker through the drift tube and appears at a lower drift time. FIG. 25 shows an extracted arrival time distribution plot along with corresponding mass spectra for the species at m/z 843.7074. A zoomed mass spectrum (FIG. 25D) is presented to prove that the doubly charged ion with a drift time of 6.67 ms is a dimeric species of the singly charged ion with 10.42 ms drift time. This compelling visual difference among the three classes signifies the potential of PSI MS combined with IM as a tool for the rapid diagnosis of Parkinson's disease.

Figure 26A:
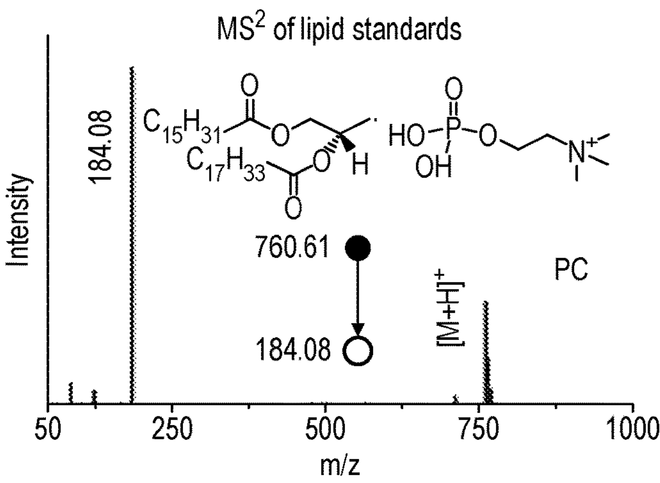
Figure 26B:
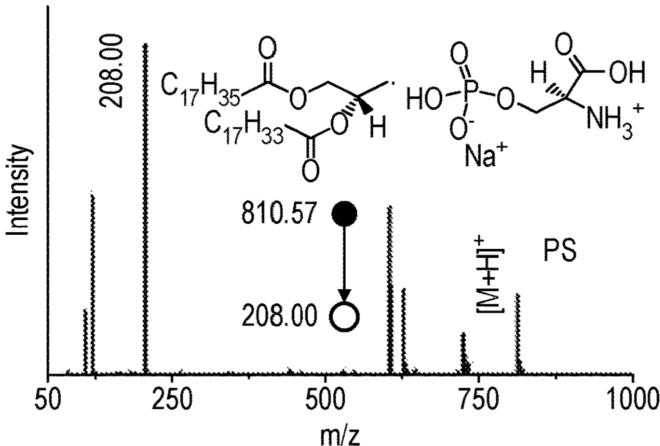
Figure 26C:
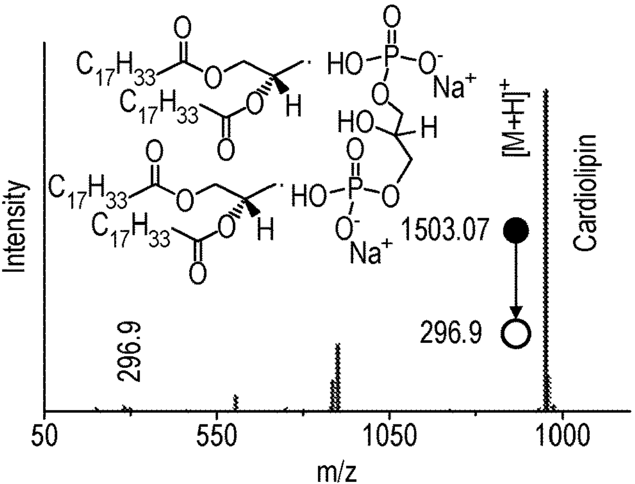

The m/z values for the statistically important features were matched against published databases to reveal putative identifications of multiple classes of lipids, predominantly belonging to the phosphatidylcholine and cardiolipin classes. A tandem mass spectrometric study was therefore performed to increase confidence in these putative annotations. For these experiments, a range of commercially available natural lipids were purchased, including: L-α-phosphatidylcholine (brain, porcine) (PC), L-α-phosphatidylserine (brain, porcine) (sodium salt) (PS), 14:1 cardiolipin, and 18:1 cardiolipin (CL). MS/MS spectra were recorded for these lipids using PSI MS. 1 mM solution of PC in $CHI_3$/MeOH, PS in $CHCl_3$, and CL in MeOH were used for tandem mass spectrometric measurements. FIG. 26A-C show $MS^2$ spectra for PC, PS, and CL, respectively. In all the cases a fragment ion was observed which corresponds to the mass of the polar head group (FIG. 26A-C highlighted in red) for the respective lipid classes. This can be considered as a fingerprint of the lipid classes for their identification using tandem mass spectrometry.

Figure 26D:
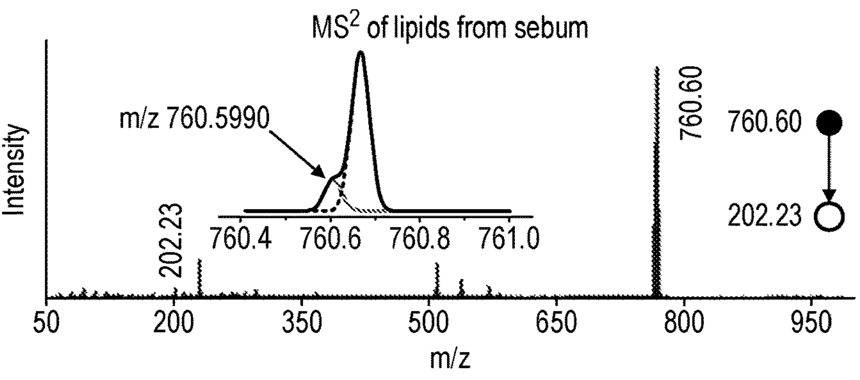
Figure 26E:
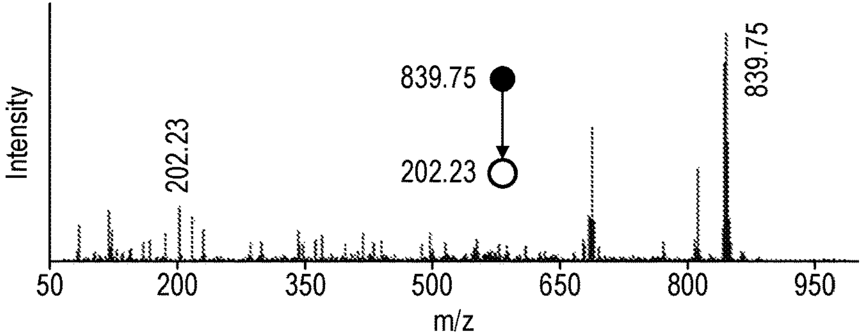
Figure 26F:
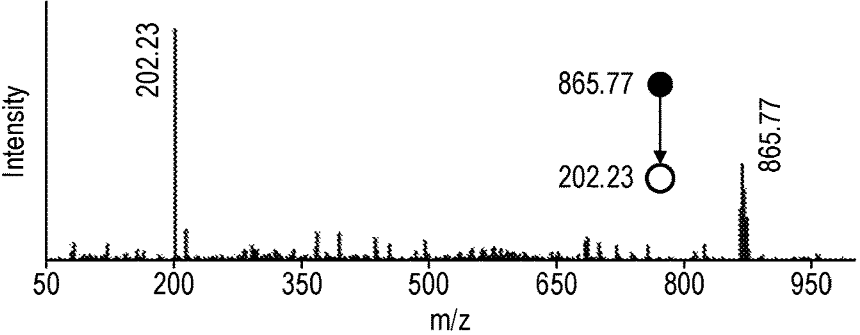
Figure 26G:
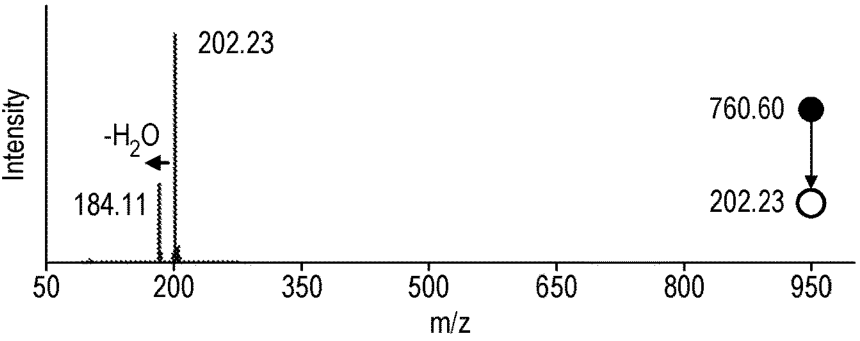

After understanding the fragmentation pattern of different lipids, $MS^2$ spectra were recorded for sebum samples selecting different ions in the m/z 700-900 region. FIG. 26D-F shows three examples of species at m/z 760.00, 839.75, and 865.77 which were isolated and subsequently fragmented using collision-induced dissociation (CID). In all of these cases, a fragment ion at m/z 202.23 was observed in the $MS^2$ spectra, which could correspond to the aqueous adduct of m/z 184.08 (the choline head group of PC). Hence, further investigation of m/z 202.23 was required to prove this speculation. As we are unable to perform an $MS^3$ experiment on a Synapt G2-Si instrument, an in-source fragmentation approach was implemented to generate further fragments of the species at m/z 202.23. In this experiment, temperature and cone voltages were raised to promote in-source fragmentation of the metabolites present in sebum (harsh conditions). It was confirmed that the species at m/z 202.23 was present under these conditions and this species was then mass isolated and fragmented using CID, this is displayed in FIG. 26G. The presence of a peak at m/z 184.11 equates to the loss of 18 Da which corresponds to the loss of the head group of PC lipids. This data proves that the fragment ion observed at m/z 202.23 is an aqueous adduct of choline head group of PC and the lipid molecules observed in the m/z 700-900 region during PSI MS of sebum belongs to phosphatidylcholine lipid class. An accurate mass measurement also supports the above statement. Before the accurate mass measurement, the instrument was calibrated using a 1 ppm mass error threshold. Inset of FIG. 26D shows a zoomed view of a peak at m/z 760.5990 which corresponds to a phosphatidylcholine molecule with chemical formula $C_{42}O_8H_{83}PN$. $MS^2$ on higher molecular mass peaks were also performed. FIG. 27 shows $MS^2$ spectra for selected ions in the m/z 1500-1700 region (another envelope of peaks with lipid-like features). The tandem mass spectra show fragment ion peaks in the range m/z 750-900 region which is consistent with the fragmentation pattern of standard CL (18:1 cardiolipin) (FIG. 26C). The only difference between the two is in the case of sebum, we see an array of fragment peaks in that region. This observation can be attributed to the fact that sebum is a complex mixture of different molecules. There is a chance that it may contain multiple CL with closely related chemical structures which contributes to the array of fragment ions observed. Although the fragment ion resembling the mass of the polar head group (m/z 296.9 in FIG. 26C) was not visible in the case of sebum, there is a high possibility that it can be present as an adduct at a different m/z value. For example, the fragment ion observed at m/z 365.29 can be [Head group of $CL+Na+K+3H_2O]^+$. Careful $MS^n$ experiments are required for better identification of the fragment ions. But, from fragment pattern of these higher-mass molecules, which matches CL standards, and the online database search report we speculate them to be CL. From the above data, it was evident that PC and CL are the important components of sebum which can be identified using PSI IM MS and they are contrasting in case of the participants having Parkinson's symptoms. Hence PSI MS combined with IM can be used as an efficient tool for the rapid diagnosis of Parkinson's disease at a very early stage.

EXAMPLE 8—LIPID IDENTIFICATION AGAINST STANDARDS

In order to classify statistically important features in the DT vs. m/z spectra, we employed accurate mass searches of available databases. This led to the putative identification of multiple classes of lipids. Collision cross section values for these lipids was calculated and compared with commercially available lipid standards to increase confidence of the annotations. Tandem mass spectrometry was used for further confirmation of the identified lipid class.

Figure 29A:
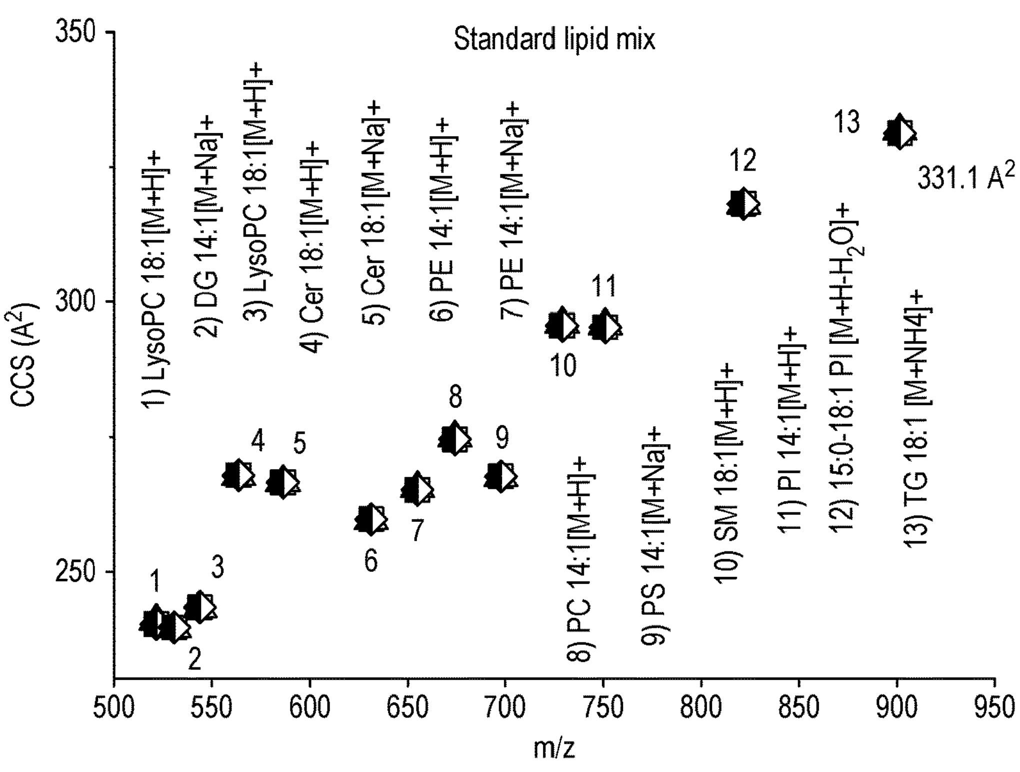
Figure 29B:
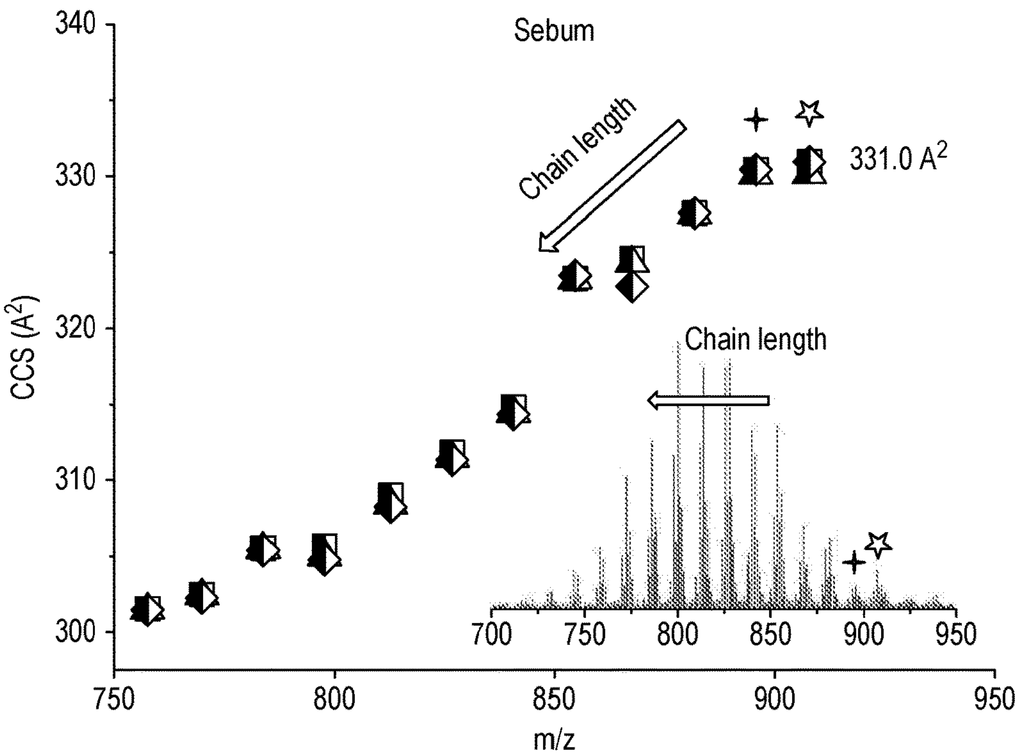
Figure 29C:
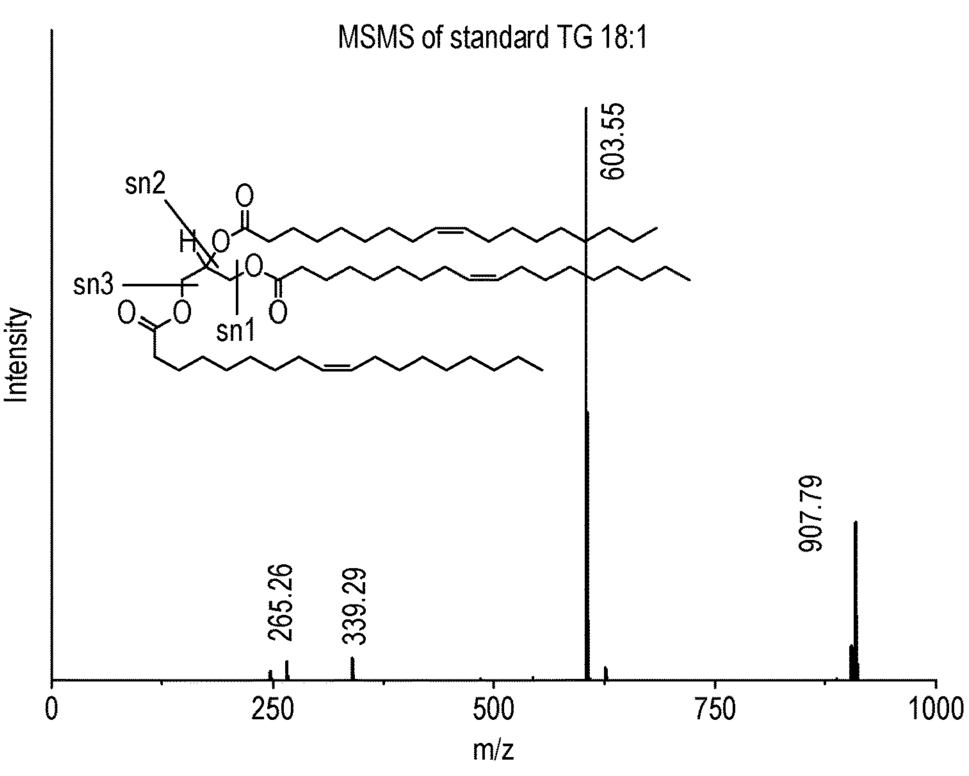
Figure 29D:
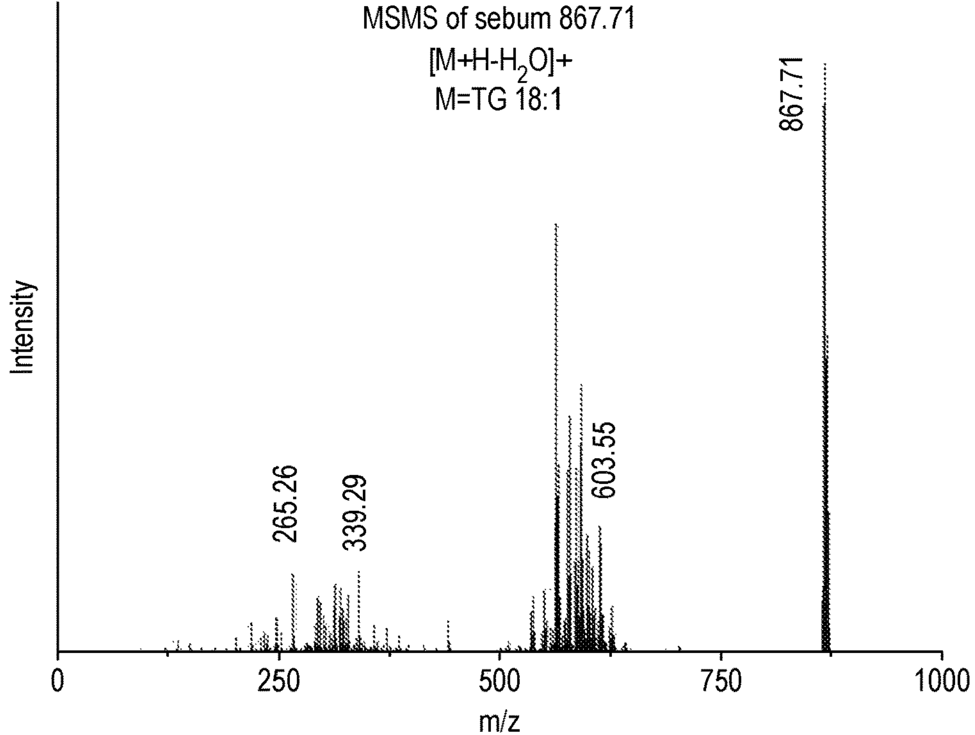

For these experiments, standard lipid mixture (Differential Ion Mobility System Suitability Synthetic Standard Mixture, and LightSPLASH™ LIPIDOMIX® Quantitative Mass Spec Primary Standard, Avanti Polar Lipids) were purchased. Desalination (using Ziptips C18) and dilution of these standards were performed prior to PSI IM MS measurement using a travelling wave instrument (Waters Cyclic IMS). Triplicate data files were acquired for each sample under identical conditions. Different classes and adducts of lipids present in the mixture were identified (1-13 in FIG. 29). The data files were processed using Driftscope to calculate the CCS values for the identified lipid components. FIG. 29A shows the CCS vs m/z plot for the standard lipid mixture. PSI IM MS of sebum was also measured under identical instrumental conditions. CCS values of the targeted peaks (identified as lipids in the database search) were calculated. FIG. 29 B shows CCS vs m/z plot for sebum. The inset in FIG. 29 B shows the targeted envelope of peaks. The linear correlation (FIG. 29 B) of the CCS values indicates the variation of chain lengths in the lipids present in sebum. The CCS value of m/z 902.51 (CCS value 331.0 $A^2$) in sebum closely match with TG class of lipid (CCS value 331.1 $A^2$, standard deviation 0.31) present in the standard (0.8% error).

Tandem mass spectrometry is one of the most important tools for structural identification of lipids and so was applied here to gain increased confidence in lipid identification alongside CCS matching. FIG. 29 C shows the MSMS spectrum of m/z 907.79 (TG 18:1 $[M+Na]^+$) measured from mixture of standard lipids. Three predominant peaks were identified as fragment ions generated due to fragmentation in sn1, sn2 and sn3 positions. It has previously been shown in the literature (https://www.lipidmaps.org), the lipid TG 18:1 can also form a precursor ion at m/z 867.78 $[M+H-H_2O]^+$. A peak at m/z 867.71 was seen in sebum samples that shows similar fragmentation to that of the TG class of lipid (FIG. 29 D). CCS values for this peak are also very close (1.8% error) to TG 18:1. Hence, we speculate that the lipids present in sebum belongs to the TG lipid class. MSMS spectra of different peaks (appearing at 14 Da apart on the lower mass range) present in sebum are shown in FIG. 30. Fragment peaks at m/z 339.29 and 265.26 Da are common in all of these spectra which indicates two of the fatty acid chains in the TG class of lipid are common and the chain length varies on the third fatty acid.

Although the CCS values for the smaller chain lipids (present in sebum) match closely with another class of lipid present in the standard (15:0-18:1 PI), the tandem mass spectrometric study confirms that the lipids present in sebum do not belong to PI class. FIG. 31 shows the MSMS spectra of 15:0-18:1 PI has a loss of 259 Da (head group of the PI lipid class) which is characteristic for PI class of lipid. The peaks present in sebum do not show this same fragmentation.

The forgoing embodiments are not intended to limit the scope of the protection afforded by the claims, but rather to describe examples of how the invention may be put into practice.

REFERENCES

1 DeMaagd, G. and A. Philip, *Parkinson's Disease and Its Management: Part 1: Disease Entity, Risk Factors, Pathophysiology, Clinical Presentation, and Diagnosis*. Pharmacy and Therapeutics, 2015. 40(8): p. 504-532.

2. Cheng, H.-C., C. M. Ulane, and R. E. Burke, *Clinical Progression in Parkinson's Disease and the Neurobiology of Axons*. Annals of neurology, 2010. 67(6): p. 715-725.

3. Morgan, J., *Joy of super smeller: sebum clues for PD diagnostics*. The Lancet Neurology. 15(2): p. 138-139.

4. Wood-Kaczmar, A., S. Gandhi, and N. Wood, *Understanding the molecular causes of Parkinson's disease*. Trends in molecular medicine, 2006. 12(11): p. 521-528.

5. Krestin, D., *The Seborrhoeic Facies as a Manifestation of Post-Encephalitic*

*Parkinsonism and Allied Disorders*. QJM: An International Journal of Medicine, 1927. os-21(81): p. 177-186.

6. Donadio, V., et al., *Skin nerve alpha-synuclein deposits: a biomarker for idiopathic Parkinson disease*. Neurology, 2014. 82(15): p. 1362-9.

7. Shirasu, M. and K. Touhara, *The scent of disease: volatile organic compounds of the human body related to disease and disorder*. The Journal of Biochemistry, 2011. 150(3): p. 257-266.

8. Pizzini, A., et al., *Analysis of volatile organic compounds in the breath of patients with stable or acute exacerbation of chronic obstructive pulmonary disease*. Journal of breath research, 2018.

9. Ishibe, A., et al., *Detection of gas components as a novel diagnostic method for colorectal cancer*. Annals of Gastroenterological Surgery, 2018.

10. Chang, J.-E., et al., *Analysis of volatile organic compounds in exhaled breath for lung cancer diagnosis using a sensor system*. Sensors and Actuators B: Chemical, 2018. 255: p. 800-807.

11. Lawal, O., et al., *Headspace volatile organic compounds from bacteria implicated in ventilator-associated pneumonia analysed by TD-GC/MS*. Journal of breath research, 2018. 12(2): p. 026002.

12. Rattray, N. J. W., et al., *Taking your breath away: metabolomics breathes life in to personalized medicine*. Trends in Biotechnology, 2014. 32(10): p. 538-548.

13. Xie, J., et al., *Analysis of changes in volatile constituents and expression of genes involved in terpenoid metabolism in oleocellosis peel*. Food chemistry, 2018. 243: p. 269-276.

14. Gatzias, I., et al., *Characterization and differentiation of sheep's milk from Greek breeds based on physicochemical parameters, fatty acid composition and volatile profile*. Journal of the Science of Food and Agriculture, 2018.

15. Gerhardt, N., et al., *Volatile Compound Fingerprinting by Headspace Gas Chromatography-Ion Mobility Spectrometry (HS-GC-IMS) for the Authenticity Assessment of Honey as Benchtop Alternative to 1H-NMR Profiling. Analytical chemistry,* 2018.

16. Liu, T., et al., *An Electronic Nose Based Beverage Identification using an Improved Fisher Discriminate Analysis Method.*

17. Abedi, G., Z. Talebpour, and F. Jamechenarboo, *The survey of analytical methods for sample preparation and analysis of fragrances in cosmetics and personal care products*. TrAC Trends in Analytical Chemistry, 2018.

18. Rosier, E., et al., *Development and validation of a new TD-GC/MS method and its applicability in the search for human and animal decomposition products. Analytical and bioanalytical chemistry,* 2014. 406(15): p. 3611-3619.

19. Sariol, H. C., et al., *Characterization of the exhaustion profile of activated carbon in industrial rum "filters" based on TGA, TD-GC/MS, colorimetry and NMR relaxometry. Materials Today Communications,* 2017. 11: p. 1-10.

20. Herrington, J. S. and C. Myers, Electronic cigarette solutions and resultant aerosol profiles. Journal of chromatography A, 2015. 1418: p. 192-199.

21. Dunn, W. B., et al., *Systems level studies of mammalian metabolomes: the roles of mass spectrometry and nuclear magnetic resonance spectroscopy. Chem Soc Rev,* 2011. 40(1): p. 387-426.

22. Goodacre, R., et al., *Proposed minimum reporting standards for data analysis in metabolomics*. Metabolomics, 2007. 3(3): p. 231-241.

23. Wikoff, W. R., et al., *Metabolomics analysis reveals large effects of gut microflora on mammalian blood metabolites*. Proceedings of the National Academy of Sciences, 2009. 106(10): p. 3698-3703.

The invention claimed is:

1. A method for treating Parkinson's disease (PD) in a subject, the method comprising:

(a) providing a sebum sample from the subject;

(b) determining the level of one or more biomarker compounds in the subject's sebum sample, wherein the one or more biomarker compounds are selected from the group consisting of cardiolipins, glycolipids and phosphatidylcholines;

(c) comparing the level of the one or more biomarker compounds in the subject's sebum sample to a control sebum level of the one or more biomarker compounds;

(d) identifying that one or more cardiolipins is reduced relative to its control level, one or more glycolipids is reduced relative to its control level, or one or more phosphatidylcholines is elevated relative to its control level, thereby detecting the presence of PD in the subject; and (e) administering a therapeutically effective amount of a neuroprotective agent to the subject.

2. The method as claimed in claim 1, wherein the PD is prodromal PD, and wherein administering the therapeutically effective amount of the neuroprotective agent treats prodromal symptoms of PD in the subject.

3. The method as claimed in claim 1, wherein the PD is early onset PD, and wherein administering the therapeutically effective amount of the neuroprotective agent treats early onset PD in the subject.

4. The method as claimed in claim 1, wherein the one or more biomarker compounds have a molecular mass of ≥about 700 Da.

5. The method as claimed in claim 1, wherein the one or more biomarker compounds comprise cardiolipins and/or phosphatidylcholines.

6. The method as claimed in claim 5, wherein the one of more biomarkers comprise phosphatidylcholines and the method comprises identifying that the level of the one or more phosphatidylcholines is elevated relative to the control level.

7. The method as claimed in claim 6, wherein one or more phosphatidylcholines is identified using mass spectrometry and has a mass-to-charge ratio of between 700 and 900 m/z.

8. The method as claimed in claim 7, wherein one or more phosphatidylcholines has a mass-to-charge ratio selected from the group consisting of 816 m/z, 830 m/z, 844 m/z, 858 m/z and 868 m/z.

9. The method as claimed in claim 1, wherein determining the level of one or more biomarker compounds in the subject's sebum sample comprises using mass spectrometry.

10. The method as claimed in claim 1, wherein determining the level of one or more biomarker compounds in the subject's sebum sample comprises using paper spray ionization-ion mobility mass spectrometry.

11. The method as claimed in claim 1, wherein providing a sebum sample comprises swabbing or scraping the back of the subject to obtain the sebum sample.

12. The method as claimed in claim 11, wherein providing a sebum sample from the subject comprises using medical gauze, absorbent paper, cotton wool or a rigid implement.

13. The method as claimed in claim 1, wherein the one of more biomarkers comprise cardiolipins and/or glycolipids and the method comprises identifying that the level of one or more cardiolipins and/or glycolipids are reduced relative to the control level.

14. The method as claimed in claim 13, wherein one or more cardiolipins and/or glycolipids is identified using mass spectrometry and has a mass-to-charge ratio of ≥1200 m/z.

15. The method as claimed in claim 14, wherein one or more cardiolipins has a mass-to-charge ratio selected from the group consisting of 1,668 m/z, 1,644 m/z, 1,632 m/z, 1,628 m/z, 1,622 m/z, 1,620 m/z, 1,616 m/z, 1,604 m/z, 1,598 m/z, 1,596 m/z, 1,592 m/z, 1,580 m/z, 1,574 m/z, 1,572 m/z, 1,568 m/z, 1,556 m/z, 1,550 m/z, 1,548 m/z, 1,532 m/z, 1,526 m/z, 1,520 m/z, 1,511 m/z, 1,508 m/z, 1,502 m/z, 1,500 m/z, 1,496 m/z, 1,488 m/z, 1,484 m/z, 1,478 m/z, 1,476 m/z, 1,472 m/z, 1,466 m/z, 1,464 m/z, 1,460 m/z, 1,430 m/z, 1,428 m/z, 1,418 m/z, 1,412 m/z, 1,404 m/z and 1,388 m/z and/or the or each glycolipid has a mass-to-charge ratio selected from the group consisting of 1,454 m/z and 1,452 m/z.

* * * * *